United States Patent
Bartels et al.

(10) Patent No.: US 10,246,468 B2
(45) Date of Patent: Apr. 2, 2019

(54) BACE1 INHIBITORS

(71) Applicant: Hoffmann-La Roche Inc., Little Falls, NJ (US)

(72) Inventors: Bjoern Bartels, Basel (CH); Cosimo Dolente, Basel (CH); Wolfgang Guba, Basel (CH); Wolfgang Haap, Basel (CH); Ulrike Obst Sander, Basel (CH); Walter Vifian, Basel (CH); Thomas Woltering, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/735,890

(22) PCT Filed: Aug. 8, 2016

(86) PCT No.: PCT/EP2016/068830
§ 371 (c)(1),
(2) Date: Dec. 12, 2017

(87) PCT Pub. No.: WO2017/025491
PCT Pub. Date: Feb. 16, 2017

(65) Prior Publication Data
US 2019/0002476 A1    Jan. 3, 2019

(30) Foreign Application Priority Data
Aug. 12, 2015 (EP) ..................... 15180767

(51) Int. Cl.
*C07D 513/04* (2006.01)
(52) U.S. Cl.
CPC .................. *C07D 513/04* (2013.01)

(58) Field of Classification Search
CPC .................................................. C07D 513/04
See application file for complete search history.

(56) References Cited

U.S. PATENT DOCUMENTS

| | | | |
|---|---|---|---|
| 9,540,392 B2 * | 1/2017 | Kettschau | C07D 495/04 |
| 9,920,072 B2 * | 3/2018 | Bartels | C07D 513/04 |
| 2016/0102105 A1 * | 4/2016 | Bartels | C07D 513/04 514/226.5 |
| 2016/0318952 A1 * | 11/2016 | Guba | C07D 513/04 |
| 2017/0334930 A1 * | 11/2017 | Bartels | C07D 513/04 |
| 2018/0194779 A1 * | 7/2018 | Bartels | A61P 25/28 |

FOREIGN PATENT DOCUMENTS

| | | |
|---|---|---|
| WO | 2013174781 A1 | 11/2013 |
| WO | 2014150331 A1 | 9/2014 |

OTHER PUBLICATIONS

M.S. Malamas et al., 53 Journal of Medicinal Chemistry, 1146-1158 (2010).*
I. Hussain et al., 100 Journal of Neurochemistry, 902-809 (2007).*
N. Marchant et al., 33 Neurobiology of Aging (2012).*
Y Huang et al., 148 Cell, 1204-1221 (2012).*
A. Corbett et al., 11 Nature Reviews Drug Discovery, 833-846 (2012).*
J.G. Sheng et al., 14 Neurobiology of the Brain, 133-145 (2003).*
The International Search Report and Written Opinion, dated Oct. 6, 2016, in the corresponding PCT Appl. No. PCT/EP2016/068830.

* cited by examiner

*Primary Examiner* — Alexander R Pagano

(57) ABSTRACT

The present invention provides a compound of formula I, having BACE1 inhibitory activity, their manufacture pharmaceutical compositions containing them and their use as therapeutically active substances. The active compounds of the present invention are useful in the therapeutic and/or prophylactic treatment of e.g. Alzheimer's disease.

19 Claims, No Drawings

BACE1 INHIBITORS

CROSS-REFERENCE TO RELATED APPLICATIONS

This application is a National Stage Application of PCT/EP2016/068830 filed Aug. 8, 2016, which claims priority from European Patent Application No. 15180767.4, filed on Aug. 12, 2015. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps.

Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36): 26326). It is thus presumed that inhibitors of BACE1 activity can be useful agents for therapeutic intervention in Alzheimer's disease (AD). Several patent applications have been filed describing BACE1 inhibitors of various structures, e.g. WO2009103626, WO2010128058, WO2011020806, WO2011029803, WO2011069934, WO2011070029, WO2011138293, WO2012019966, WO2012028563, WO2012098064, WO2012104263, WO2012107371, WO2012110459, WO2012119883, WO2012126791, WO2012136603, WO2012139993, WO2012156284, WO2012163790, WO2012168164, WO2012168175, WO2013004676, WO2013041499, WO2013110622, WO2013174781, WO2014001228, WO2014114532, WO2014150331, WO2014150340, WO2014059185 and WO2014150344.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides compounds having BACE1 inhibitory properties, their manufacture, pharmaceutical compositions containing them and their use as therapeutically active substances.

SUMMARY OF THE INVENTION

The present invention provides a compound of formula I,

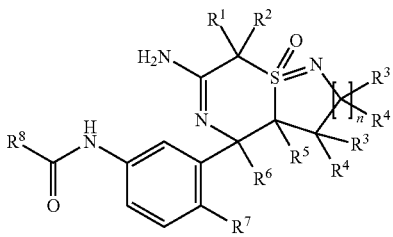

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the AP production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl" or "$C_{1-6}$-alkyl-halogen", alone or in combination with other groups, refers to $C_{1-6}$alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl (pyridyl), pyrimidinyl (pyrimidyl), pyrrolyl, quinolinyl, tetrazolyl, thiazolyl, thienyl, triazolyl, 6,7-dihydro-5H-[1]pyrindinyl and the like. Particular "heteroaryl" groups are pyridyl, pyrazinyl and imidazo[1,2-a]pyridinyl.

The term "aryl" denotes a monovalent aromatic carbocyclic mono- or bicyclic ring system comprising 6 to 10 carbon ring atoms. Examples of aryl moieties include phenyl and naphthyl. Particular "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The term "amino", alone or in combination with other groups, refers to —$NH_2$.

The terms "hydroxyl" or "hydroxyl", alone or in combination with other groups, refer to —OH.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "$C_{3-6}$-cycloalkyl" refers to a 3 to 8 membered carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Specific is cyclopropyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific are ethoxy and methoxy.

The term "halogen-$C_{1-6}$-alkoxy", alone or in combination with other groups, refers to $C_{1-6}$-alkoxy as defined herein, which is substituted by one or multiple halogens, in particular fluoro.

Particular "halogen-$C_{1-6}$-alkoxy" are fluoro-$C_{1-6}$-alkoxy. Specific "halogen-$C_{1-6}$-alkoxy" are $CHF_2$—$CF_2$—$CH_2$—O—, $CHF_2$—O— and $CF_2$—O—.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught and A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

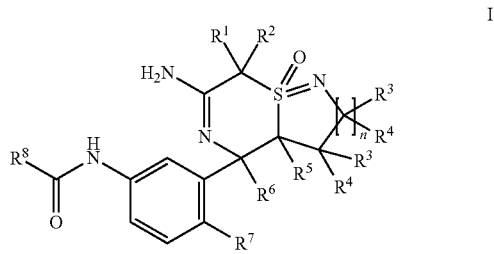

I wherein
n is 1, 2 or 3;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is each independently selected from the group consisting of
  i) hydrogen,
  ii) $C_{1-6}$-alkyl, and
  iii) halogen;
$R^4$ is each independently selected from the group consisting of
  i) hydrogen,
  ii) $C_{1-6}$-alkyl, and
  iii) halogen;

or wherein $R^3$ and $R^4$ together are —$(CH_2)_m$—, wherein m is 2, 3, 4 or 5,
$R^5$ is hydrogen.
$R^6$ is selected from the group consisting of
  i) $C_{1-6}$-alkyl, and
  ii) halogen-$C_{1-6}$-alkyl;
$R^7$ is selected from the group consisting of
  i) hydrogen, and
  ii) halogen;
$R^8$ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $COOR^9$, wherein $R^9$ is H or $C_{1-6}$-alkyl, $CONR^{10}R^{11}$, wherein $R^{10}$ is H or $C_{1-6}$-alkyl $C_{3-6}$-cycloalkyl and $R^{11}$ is H or $C_{1-6}$-alkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{1-6}$-cycloalkyl-$C_{1-6}$-alkoxy and $C_{3-6}$-cycloalkyl-$C_1$-alkoxy, wherein the cycloalkyl unit is substituted by 1 to 4 substituents individually selected from the group consisting of halogen, cyano, $C_{1-6}$-alkyl and $C_{1-6}$-alkoxy;
  iii) heteroaryl, and
  iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $COOR^9$, wherein $R^9$ is H or $C_{1-6}$-alkyl, $CONR^{10}R^{11}$, wherein $R^{10}$ is H or $C_{1-6}$-alkyl $C_{3-6}$-cycloalkyl and $R^{11}$ is H or $C_{1-6}$-alkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{1-6}$-cycloalkyl-$C_{1-6}$-alkoxy and $C_{3-6}$-cycloalkyl-$C_1$-alkoxy, wherein the cycloalkyl unit is substituted by 1 to 4 substituents individually selected from the group consisting of halogen, cyano, $C_{1-6}$-alkyl and $C_{1-6}$-alkoxy;
or pharmaceutically acceptable salts thereof.

A certain embodiment of the invention provides a compound of formula I as described herein, wherein n, $R^1$, $R^2$, $R^3$, $R^4$, $R^5$, $R^6$, $R^7$ and $R^8$ are as described in herein and when n=1, then the 5-ring has cis configuration.

A certain embodiment of the invention provides a compound of formula I as described herein, which is of formula Ia, wherein n, $R^1$, $R^2$, $R^3$, $R^4$, $R^5$, $R^6$, $R^7$ and $R^8$ are as described in herein.

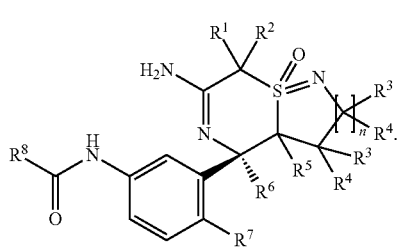

A certain embodiment of the invention provides a compound of formula I as described herein, wherein $R^1$ is methyl.

A certain embodiment of the invention provides a compound of formula I as described herein, wherein $R^2$ is methyl.

A certain embodiment of the invention provides a compound of formula I as described herein, wherein $R^3$ is hydrogen.

A certain embodiment of the invention provides a compound of formula I as described herein, wherein $R^4$ is hydrogen.

A certain embodiment of the invention provides a compound of formula I as described herein, wherein $R^5$ is hydrogen.

A certain embodiment of the invention provides a compound of formula I as described herein, wherein $R^6$ is methyl.

A certain embodiment of the invention provides a compound of formula I as described herein, wherein $R^7$ is F.

A certain embodiment of the invention provides a compound of formula I as described herein, wherein $R^8$ is heteroaryl, substituted by 1-2 substituents individually selected from cyano, halogen, halogen-$C_{1-6}$-alkoxy, halogen-$C_{1-6}$-alkyl and $C_{1-6}$-alkyl.

A certain embodiment of the invention provides a compound of formula I as described herein, wherein $R^8$ is heteroaryl which is selected from pyridinyl, pyrazinyl, pyrimidyl or 1H-pyrazolyl, each substituted by 1-2 substituents individually selected from cyano, halogen, halogen-$C_{1-6}$-alkoxy, halogen-$C_{1-6}$-alkyl and $C_{1-6}$-alkyl.

A certain embodiment of the invention provides a compound of formula I as described herein, wherein $R^8$ is heteroaryl, substituted by 1-2 substituents individually selected from cyano and $C_{1-6}$-alkyl.

A certain embodiment of the invention provides a compound of formula I as described herein, wherein $R^8$ is pyridyl, substituted by 1-2 substituents individually selected from cyano and $C_{1-6}$-alkyl.

A certain embodiment of the invention provides a compound of formula I as described herein, wherein $R^8$ is phenyl substituted by 1-2 substituents individually selected from cyano, halogen and $C_{1-6}$-alkyl.

A certain embodiment of the invention provides a compound of formula I as described herein wherein n is 1.

A certain embodiment of the invention provides a compound of formula I as described herein wherein n is 1, $R^1$ is methyl, $R^2$ is methyl, $R^3$ is H, $R^4$ is H, $R^5$ is H, $R^6$ is methyl and $R^7$ is F.

A certain embodiment of the invention provides a compound of formula I as described herein that is selected from the group consisting of
N-(3-((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide,
N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide,
N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide,
N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide,
N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide,
N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)pyrazine-2-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-cyano-2-methylbenzamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)-3-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(difluoromethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxypyrazine-2-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)pyrazine-2-carboxamide, N-(3-((3aS,4R,8R)-6-amino-4,7,7-trimethyl-8-oxido-3,3a,4,7-tetrahydro-2H-isothiazolo[1,5-a][1,A]thiazin-4-yl)-4-fluorophenyl)-5-cyanopicolinamide, N-(3-((3aS,4R,8R)-6-amino-4,7,7-trimethyl-8-oxido-3,3a,4,7-tetrahydro-2H-isothiazolo[1,5-a][1,A]thiazin-4-yl)-4-fluorophenyl)-5-fluoropicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-chloropicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-difluoropicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-2-methylpyrimidine-5-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)pyrazine-2-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dimethylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxypicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-ethoxypicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxy-3-methylpicolinamide, and N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-ethoxypyrazine-2-carboxamide, or pharmaceutically acceptable salts thereof.

A certain embodiment of the invention provides a compound of formula I as described herein that is selected from the group consisting of N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide, N-(3-((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)pyrazine-2-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-cyano-2-methylbenzamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)-3-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(difluoromethoxy)picolinamide, and N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxypyrazine-2-carboxamide, or pharmaceutically acceptable salts thereof.

A certain embodiment of the invention provides a compound of formula I as described herein that is selected from the group consisting of N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide and N-(3-

((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide,
or pharmaceutically acceptable salts thereof.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

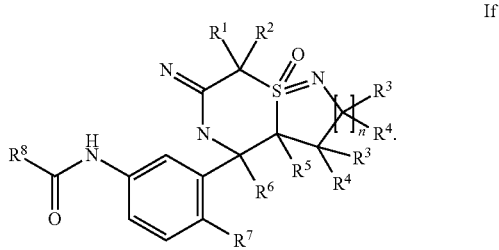

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Certain embodiments are the following specific forms:

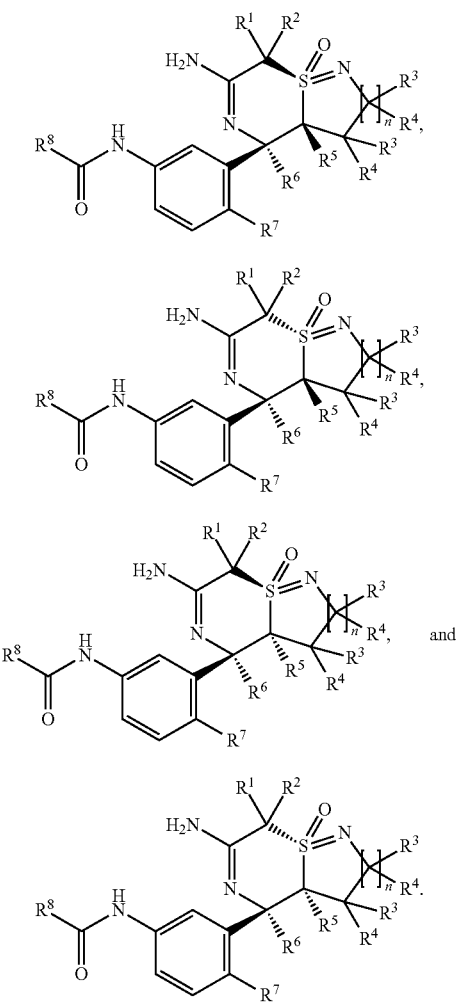

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I can be prepared through a number of synthetic routes for example as illustrated in schemes 1-14. The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be prepared through a number of synthetic routes for example as illustrated in schemes 1-14. The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

Key intermediate A6 can be prepared via the intermediates depicted in Scheme 1. Commercially available 2-(methylthio)acetonitrile (A1) can be alkylated using a base, such as e.g. sodium hydride, in the presence of an appropriate alkylating agent, e.g. alkyl iodide or alkyl bromide, in a suitable aprotic solvent, e.g. tetrahydrofuran, to give the corresponding intermediate A2. Alternatively, the alkylation agent can be an appropriate aldehyde, e. g. paraformaldehyde. The resulting hydroxy compounds can thereafter be transformed into the corresponding halogen compounds be methods known in the art, e.g. using suitable fluorinating agents, such as diethylaminosulfurtrifluoride, to obtain intermediates A2. The alkylations can be run stepwise, or, if $R^1=R^2$, in one pot using appropriate reagent excesses.

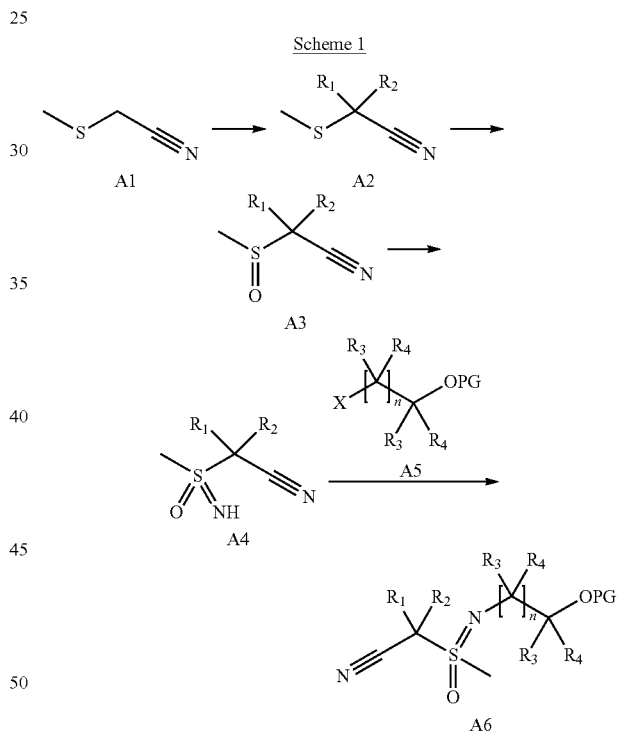

Intermediate A2 can be oxidized to the corresponding sulfoxide A3 using suitable oxidation procedures known in the art, e.g. using sodium periodate, m-chloroperbenzoic acid or oxone. The following formation of the sulfoximine moiety to obtain intermediate A4 can be achieved by methods known in the art, e.g. in two steps using, e.g. catalytic amounts of dirhodiumtetraacetate, and stoichiometric amounts of diacetoxyiodosobenzene, trifluoroacetamide and magnesium oxide, followed by hydrolysis, e.g. using potassium carbonate in lower alcohols, or, alternatively, using catalytic amounts of 4,4',4"-tri-tert-butyl-2,2':6',2"-terpyridine and silver nitrate, and stoichiometric amounts of 4-nitrobenzenesulfonamide and diacetoxyiodosobenzene, and subsequent hydrolysis using thiophenol and cesium carbonate, both steps in appropriate solvents. Alternatively, intermediate A4 can be synthesized in one step using stoichiometric amounts of sodium azide in Eaton's reagent (i.e. a solution of diphosphorouspentoxide in methanesulfonic acid). Intermediate A4 can thereafter be reacted with an appropriate alkylation reagent A5 in the presence of a suitable base, e.g. sodium hydride, potassium hydride or cesium carbonate, and optionally a catalytic amount of a quaternary ammonium salt, e.g. tetra-n-butyl ammonium bromide or tetra-n-butyl ammonium iodide, in a suitable aprotic solvent, e.g. dimethoxyethane, tetrahydrofurane or acetonitrile, to give intermediate A6. The alkylation reagent A5 is a protected halo-alcohol, in which X means a leaving group, e.g. halogen, (substituted) arene- or (substituted) alkanesulfonate, preferably bromine, iodine or tri-flouromethanesulfonate, and PG means a protecting group, e.g. tetrahydropyranyl.

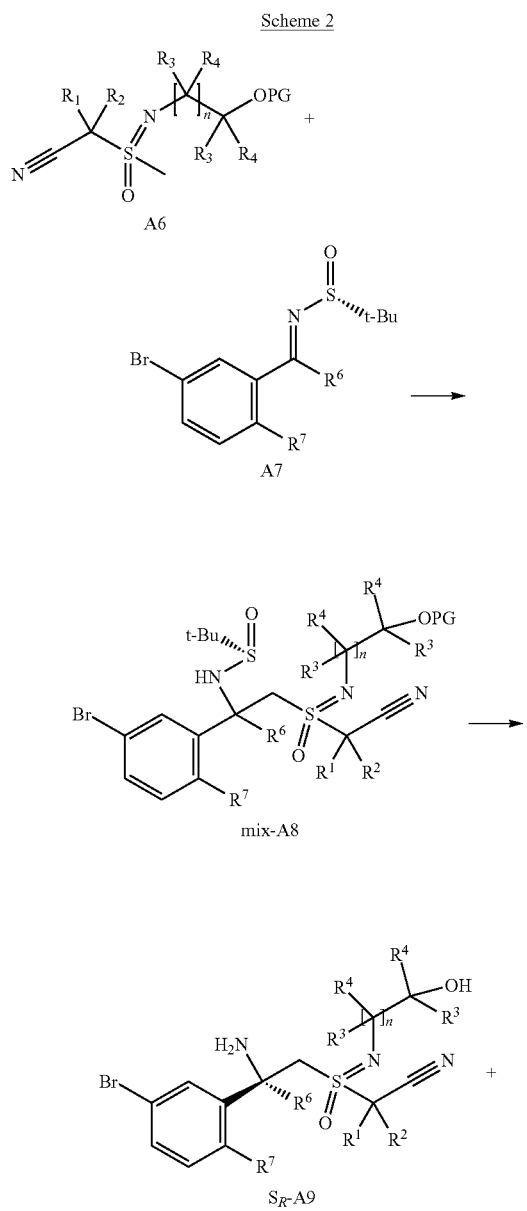

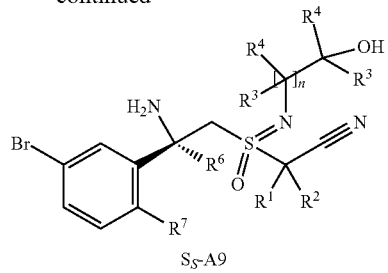

Key intermediate A6 can then be reacted with sulfoximine A7 in the presence of a strong base, e.g. alkali hexamethyldisilazide, such as lithium hexamethyldisilazide, alkali diisopropylamide, such as lithium diisopropylamide, or alkyl lithium, such as n-butyl lithium, under anhydrous conditions in a suitable aprotic solvent, e.g. tetrahydrofuran or dichloromethane, to form intermediate mix-A8 as a mixture of stereoisomers (Scheme 2). The single stereoisomers can be separated at this stage by chromatography and the route as depicted in Scheme 2 and the following schemes can be followed analogously employing the separated single isomers. Alternatively, the mixture of stereoisomers can be deprotected and the sulfoxamide moiety can be cleaved to give the corresponding aminoalcohols A9 as a mixture of enantiomerically enriched diastereomers $S_R$-A9 and $S_S$-A9. The prefix $S_X$ indicates the absolute configuration ($S_S$- for (S) and $S_R$- for (R), respectively) at the sulfur atom. In case the protecting group PG in intermediate mix-A8 is acid labile, e.g. tetrahydropyranyl, the two cleavages mentioned above can be carried out in one step under acidic conditions, e.g. using solutions of hydrogen chloride in alcohols, such as methanol or ethanol. The two enantioenriched diastereoisomers $S_R$-A9 and $S_S$-A9 can be separated by chromatography, or by other means known in the art. Alternatively, the mixture of diastereoisomers can be carried through the synthesis and the respective resulting mixtures can be separated at later stages by chromatography or by other means known in the art.

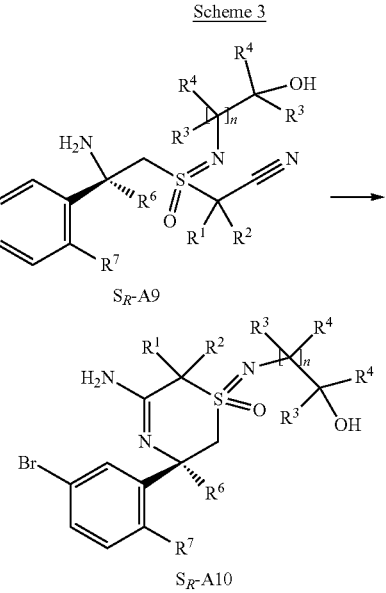

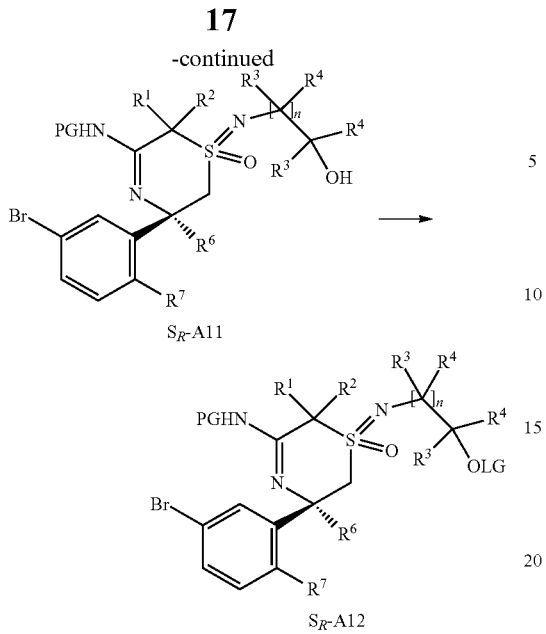

S$_R$-A11

S$_R$-A12

Subsequently, intermediate S$_R$-A9 can be cyclised to intermediate S$_R$-A10 using methods known in the art, e.g. using stoichiometric amounts of copper(I) salts, e.g. copper (I) chloride or copper(I) bromide, in suitable solvents, e.g. alcohols, such as ethanol, at elevated temperatures, such as 20° C. to 130° C., preferably at 70° C. to 90° C. (Scheme 3). Alternatively, the transformation can be achieved using stoichiometric amounts of a Lewis acid, like trimethyl aluminium, in a suitable aprotic solvent, such as toluene. The amidine function in intermediate S$_R$-A10 is then protected by an appropriate protecting group PG to give intermediate S$_R$-A11. The protecting group PG should be stable towards basic conditions and can be, e.g. tert-butoxycarbonyl (BOC). In case PG is BOC, the transformation to intermediate S$_R$-A11 can be achieved using conditions known in the art, e.g. di-tert-butyl dicarbonate in the presence of a suitable base, such as sodium hydrogencarbonate, and optionally in the presence of catalytic amounts of a suitable Lewis base, e.g. 4-(dimethylamino)-pyridine, followed by addition of a suitable nucleophile, e.g. aqueous ammonia, to eliminate the excess of di-tert-butyl dicarbonate prior to concentration of the reaction mixture. Thereafter, the hydroxy group in intermediate S$_R$-A11 is transformed into a leaving group OLG in intermediate S$_R$-A12. Suitable leaving groups include arenesulfonoyl, e.g. p-toluenesulfonoyl, alkanesulfonoyl, e.g. triflourmethanesulfonoyl, or halogen, e.g. iodine. If OLG is p-toluenesulfonoyl, the transformation to intermediate S$_R$-A12 can be achieved under standard conditions known in the art, using, e. g., p-toluenesulfonyl chloride in the presence of a suitable base, e. g. a tertiary amine, such as triethylamine or diisopropylethylamine, and, optionally, catalytic amounts of a suitable Lewis base, e. g. 4-(dimethylamino)-pyridine. If OLG is iodide, the transformation to intermediate S$_R$-A12 can be achieved under standard conditions known in the art, using, e. g., tetraalkylammonium iodide, such as tetra-n-butylammonium iodide, in the presence of a suitable phosphine, e. g. triphenylphosphine, and a suitable activator, such as 2,3-dichloro-5,6-dicyano-1,4-benzoquinone (DDQ), in an aprotic solvent, e.g. dichloromethane.

In analogy to the chemistry described above and in Scheme 3 for the transformation of intermediate S$_R$-A9 into intermediate S$_R$-A12, intermediate S$_S$-A9 can be transformed into intermediate S$_S$-A12 (Scheme 4).

Scheme 4

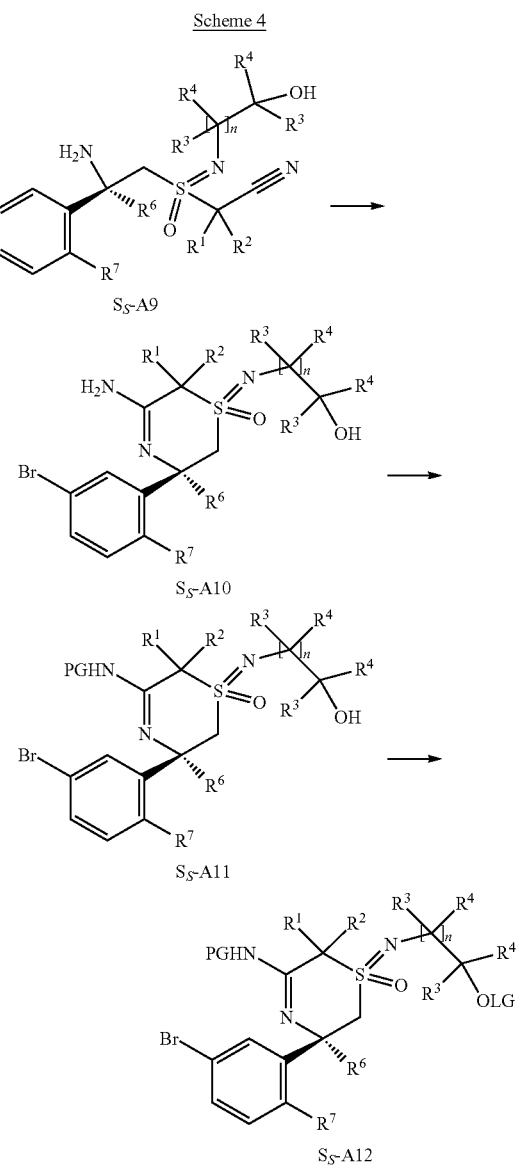

S$_S$-A9

S$_S$-A10

S$_S$-A11

S$_S$-A12

The following cyclisation step starting from intermediate S$_R$-A12 gives rise to two diastereoisomers S$_R$-A13 and S$_R$-A14 (Scheme 5). The two diastereoisomers can either be separated by means of chromatography or other means known in the art, or the mixture can be reacted in the following steps and the reaction products separated at later stages by means of chromatography, or other means known in the art. Alternatively, the mixture of diastereoisomers S$_R$-A13 and S$_R$-A14 can be reacted in the following steps exploiting reactivity differences. Likewise, if one of the two diastereoisomers S$_R$-A13 or S$_R$-A14 has a higher reactivity in the following step, this difference can be used to separate the two diastereoisomers by chromatographic means. The transformation can be achieved using a strong base, such as, e. g., lithium hexamethyldisilazide or lithium diisopropylamide, under anhydrous conditions in an aprotic solvent, e. g. tetrahydrofuran, at temperatures of −80° C. to 0° C. In certain cases, one of the two possible diastereoisomers is strongly favoured, due to steric or thermodynamic reasons.

Scheme 5

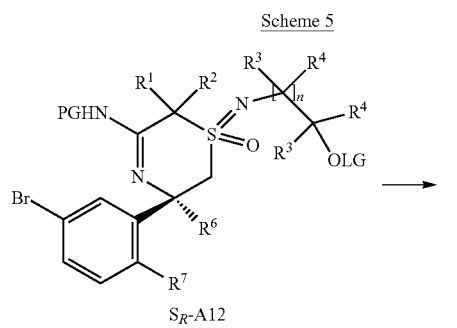

S$_R$-A12

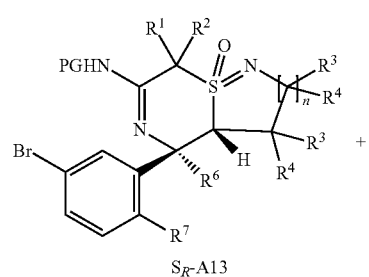

S$_R$-A13

+

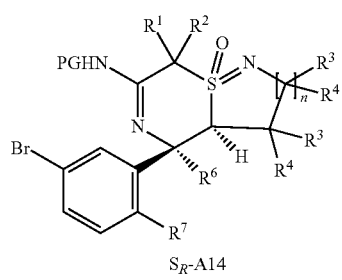

S$_R$-A14

In analogy to the chemistry described above and in Scheme 5 for the transformation of intermediate S$_R$-A12 into intermediates S$_R$-A13 and S$_R$-A14, intermediate S$_S$-A12 can be transformed into intermediates S$_S$-A13 and S$_S$-A14 (Scheme 6).

Scheme 6

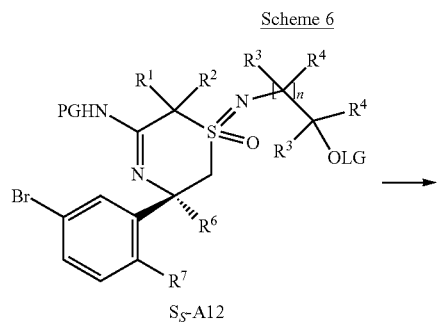

S$_S$-A12

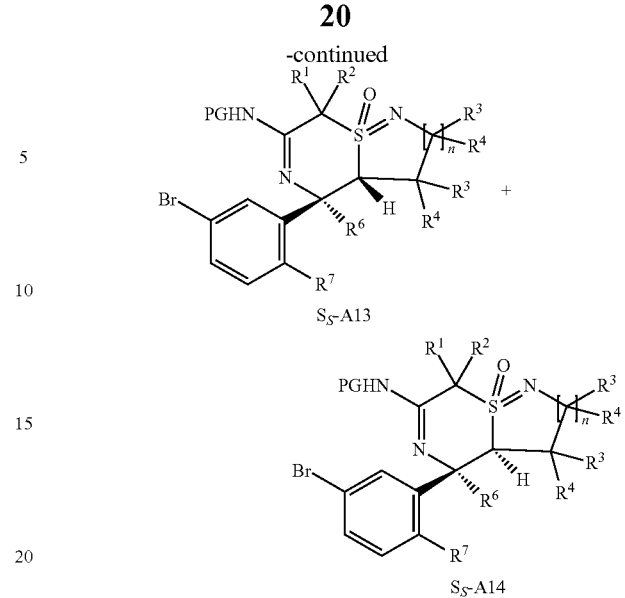

S$_S$-A13

+

S$_S$-A14

Next, intermediate S$_R$-A13 is transformed into intermediate S$_R$-A15 involving a two step procedure. First, the bromobenzene moiety in intermediate S$_R$-A13 is transformed into the corresponding azidobenzene using an excess of sodium azide, catalytic or stoichiometric amounts of a suitable copper(I) salt, such as copper(I) iodide, and a suitable diamino ligand, such as trans-N,N'-dimethylcyclohexane-1,2-diamine, and substoichiometric amounts of sodium ascorbate, in appropriate polar solvents, such as dioxane and water, at elevated temperatures, e.g. 60° C. to 80° C. Usually, a minor amount of aminobenzene intermediate S$_R$-A15 is already formed under the outlined reaction conditions. In order to drive the aminobenzene formation to completion, the resulting mixture of azido- and aminobenzene intermediates can be reacted with a triaryl- or trialkylphosphine, e.g. trimethylphosphine, in a suitable solvent, e.g. tetrahydrofuran.

Scheme 7

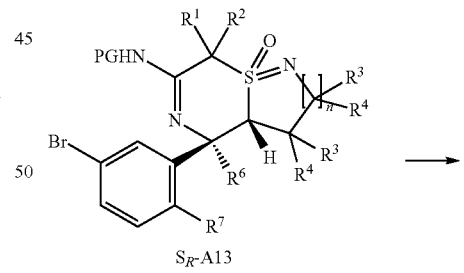

S$_R$-A13

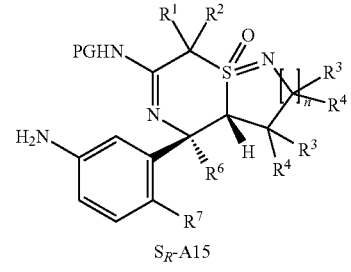

S$_R$-A15

In analogy to the chemistry described above and in Scheme 7 for the transformation of intermediate S$_R$-A13 into intermediate S$_R$-A15, intermediate S$_S$-A13 can be transformed into intermediate S$_S$-A15 (Scheme 8).

Scheme 8

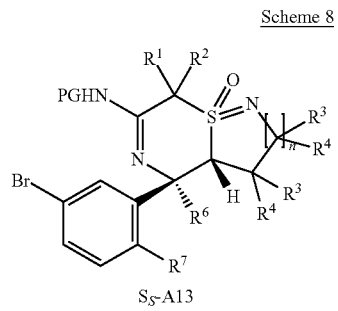

S$_S$-A13

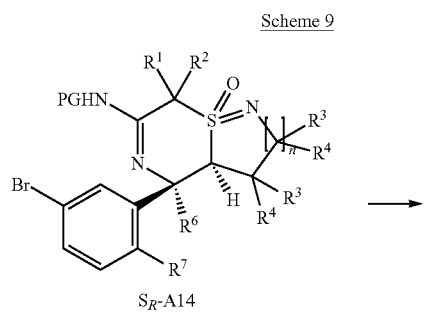

S$_S$-A15

In analogy to the chemistry described above and in Scheme 7 for the transformation of intermediate S$_R$-A13 into intermediate S$_R$-A15, intermediate S$_R$-A14 can be transformed into intermediate S$_R$-A16 (Scheme 9).

Scheme 9

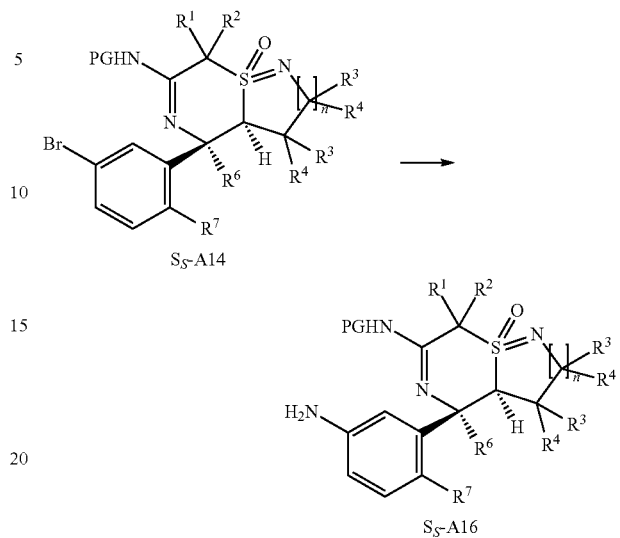

S$_R$-A14

S$_R$-A16

In analogy to the chemistry described above and in Scheme 7 for the transformation of intermediate S$_R$-A13 into intermediate S$_R$-A15, intermediate S$_S$-A14 can be transformed into intermediate S$_S$-A16 (Scheme 10).

Scheme 10

S$_S$-A14

S$_S$-A16

Thereafter, intermediate S$_R$-A15 is acylated to form intermediate S$_R$-A17 by suitable amide bond forming methods known in the art using appropriate acids R$^8$COOH, wherein R$^8$ is as defined above (Scheme 11). These methods include, as example, the reaction of intermediate S$_R$-A16 with acid R$^8$COOH in the presence of stoichiometric amounts of 1-chloro-N,N,2-trimethyl-propenylamine and a suitable base, e. g. a tertiary amine, such as diisopropylethylamine, in an aprotic solvent, e. g. dichloromethane, at temperatures of −10° C. to 30° C. Alternatively, acid R$^8$COOH can be transformed into the corresponding acid chloride R$^8$COCl using methods known in the art, e. g. using oxalyl chloride or thionyl chloride in aprotic solvents, such as dichloromethane or toluene. The isolated acid chloride R$^8$COCl can then be reacted with intermediate S$_R$-A15 in the presence of a suitable base, e.g. a tertiary amine, such as diisopropylethylamine, in an aprotic solvent, e. g. dichloromethane, at temperatures of −10° C. to 30° C. to form intermediate S$_R$-A17. Finally, intermediate S$_R$-A17 is deprotected by methods known in the art to give access to final compounds S$_R$-A18. If PG is BOC, the deprotection is achieved by stirring intermediate S$_R$-A17 in the presence of an excess of a strong acid, such as triflouroacetic acid or hydrogen chloride either in a suitable solvent, such as dichloromethane or tetrahydrofuran or without a solvent under neat conditions, if feasible. Subsequently, the enantiomerically enriched products of formula S$_R$-A18 are purified to their enantiopure form by chromatography using suitable chiral stationary phases.

Scheme 11

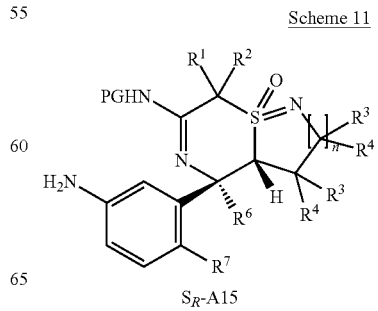

S$_R$-A15

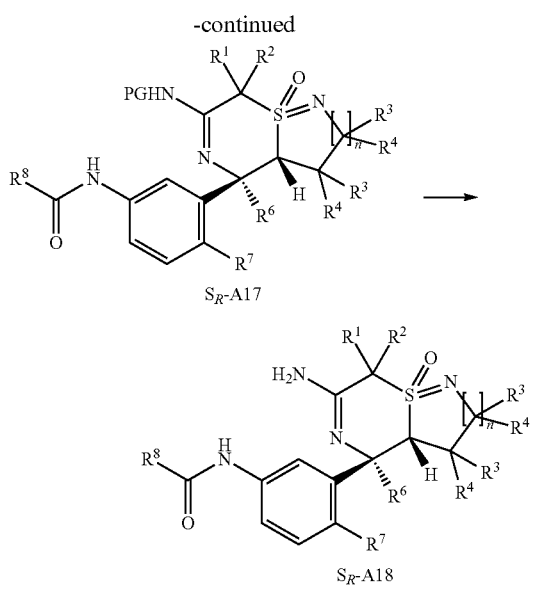

S<sub>R</sub>-A17

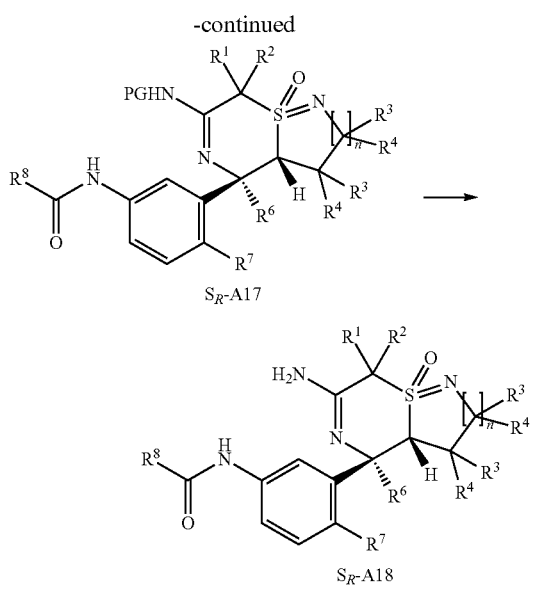

S<sub>R</sub>-A18

In analogy to the chemistry described above and in Scheme 11 for the transformation of intermediate S<sub>R</sub>-A15 into enantiopurified final compound S<sub>R</sub>-A18, intermediate S<sub>S</sub>-A15 can be transformed into enantiopurified final compound S<sub>S</sub>-A18 (Scheme 12).

Scheme 12

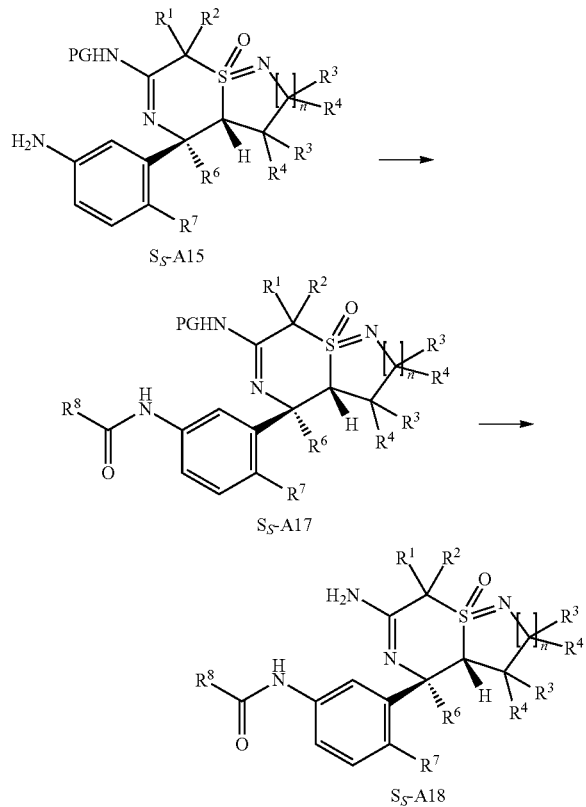

In analogy to the chemistry described above and in Scheme 11 for the transformation of intermediate S<sub>R</sub>-A15 into enantiopurified final compound S<sub>R</sub>-A18, intermediate S<sub>R</sub>-A16 can be transformed into enantiopurified final compound S<sub>R</sub>-A20 (Scheme 13).

Scheme 13

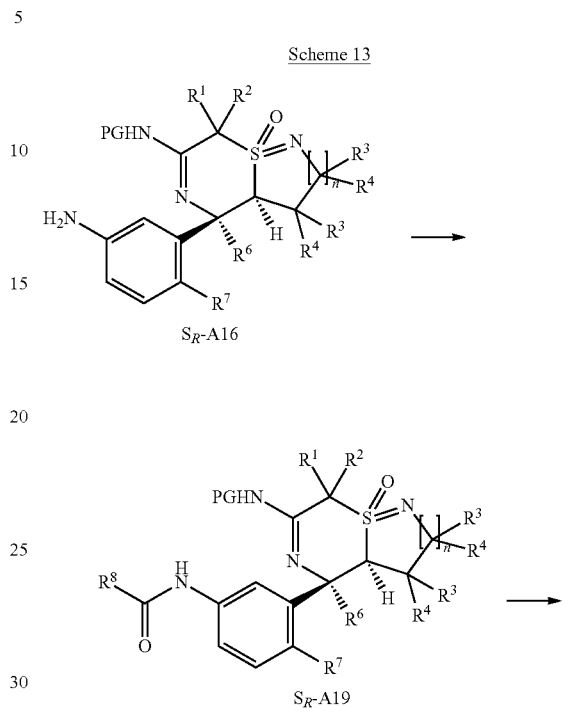

In analogy to the chemistry described above and in Scheme 11 for the transformation of intermediate S<sub>R</sub>-A15 into enantiopurified final compound S<sub>R</sub>-A18, intermediate S<sub>S</sub>-A16 can be transformed into enantiopurified final compound S<sub>S</sub>-A20 (Scheme 14).

Scheme 14

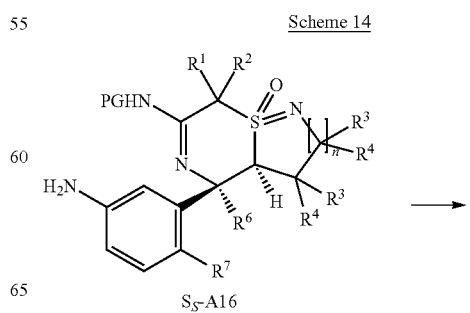

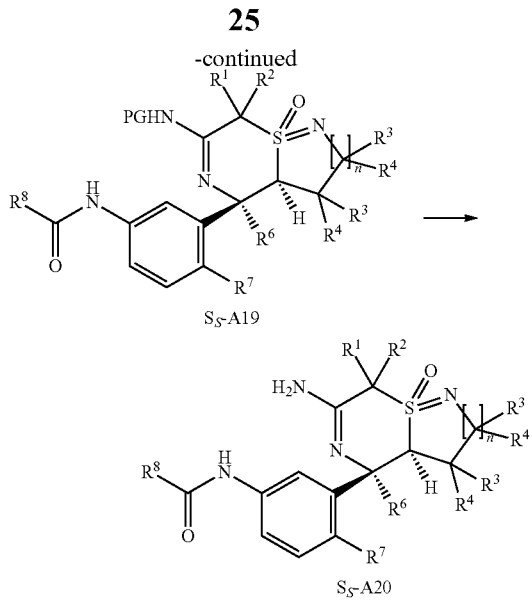

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2 μl of a 10× AlphaLISA Anti-hABAcceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader.

Levels of Aβ 40 in the culture supernatants were calculated as percentage of maximum signal (cells treated with 1% DMSO without inhibitor). The $IC_{50}$ values were calculated using the Excel XLfit software.

Lowering of Aβ40 in Brain of Wild-Type Mice:
Animals and Housing Conditions.

Animals were maintained in a 12/12 h light/dark cycle, with lights starting at 6 a.m., and experiments were conducted during the light phase. Animal housing and experimental procedures were in line with ethical and legal guidelines and were authorized by local veterinary authorities.

Experiment. Female $C_{57}Bl/6J$ mice were treated with a dose of 30 mg/kg of the compounds, 3-4 animals per treatment group. The test compound was dissolved in 5% EtOH, 10% Solutol, and was applied per os at 10 mL/kg. After 4 h, the animals were sacrificed and brain and plasma were collected. The brain was cut into halves and immediately frozen on dry ice. Brain was used for measurement of Aβ40 and plasma was used for determination of compound exposure. The method for Aβ40 determination in brain lysates followed the known procedure (Lanz, T. A.; Schachter, J. B. Demonstration of a common artifact in immunosorbent assays of brain extracts: development of a solidphase extraction protocol to enable measurement of amyloid-β from wild-type rodent brain. J. Neurosci. Methods 2006, 157, 71-81.). Brain tissue was homogenized in 2% DEA buffer in a Roche MagnaLyser (20", 4000 rpm) and subsequently centrifuged for 1 h at 100000 g. DEA was reduced to 0.2% in 50 mM NaCl and one-half of the DEA lysate was passed over an Oasis Solid phase extraction plate (Waters; cat. no. 186000679), which had been activated with MeOH and equilibrated in dH2O (1 mL each). After washes in 10% and 30% MeOH (1 mL each), the Aβ-peptides were eluted in 0.8 mL of 2% $NH_4OH$ in 90% MeOH. The eluate was dried over a N2 flow, and the dried sample was reconstituted in 30 μL of AlphaLISA assay buffer. Aβ40 was determined by an AlphaLISA assay (Perkin-Elmer). In a white 96-well, half area microplate (Perkin-Elmer cat. no. 6005561), 20 μL of the reconstituted sample were mixed with 5 μL of biotinylated BAP-24 (specific for C-terminus of Aβ40) (Brockhaus, M.; Grunberg, J.; Rohrig, S.; Loetscher, H.; Wittenburg, N.; Baumeister, R.; Jacobsen, H.; Haass, C. Caspasemediated cleavage is not required for the activity of presenilins in amyloidogenesis and NOTCH signaling. NeuroReport 1998, 9, 1481-1486.) stock=4.4 mg/mL, f.c.5.5 μg/mL), and 5 μL 252Q6 acceptor beads (252Q6 antibody, Invitrogen AMB0062) had been previously conjugated with AlphaLISA Acceptor beads (Perkin-Elmer cat. no. 6772002); final dilution 1:500). The mix was incubated for 1 h at RT in the dark. Then 20 μL of Streptavin-coated Donor Beads (Perkin-Elmer cat. no. 6760002, final dilution 1:125) were added and this final mix was incubated in the dark for another 30 min at RT before RFU was measured in an AlphaScreen Reader (Perkin-Elmer Envision 2104). The value obtained for Aβ40 in the treated animals was related to the value in the vehicle group and is given in %. Alternatively a commercial ELISA was used for Aβ40 determination (Wako ELISA: ("Human/Rat β Amyloid (40) ELISA kit Wako II"; cat nr. 294-64701) following the manufacture's instruction. Also here the Aβ-lowering efficacy was calculated as percentage of the vehicle group.

TABLE 1

Pharmacological data

| Ex. | Structure | BACE1 cell act. Aβ40 IC50 [nM] | Aβ40 (wt mice, brain) [%] | Name |
|---|---|---|---|---|
| 1AB | 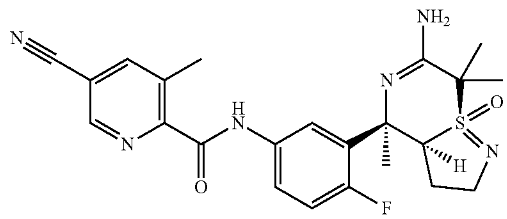 | 0.09 | 14 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-cyano-3-methylpicolinamide |
| 1BA | 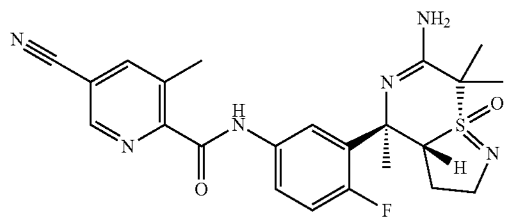 | 3.6 | 73 | N-(3-((3aR,4R,8S)-6-amino-4,7,7-trimethyl-8-oxido-3,3a,4,7-tetrahydro-2H-isothiazolo[1,5-1][1,4]thiazin-4-yl)-4-fluorophenyl)-5-cyano-3-methylpicolinamide |
| 2AB | 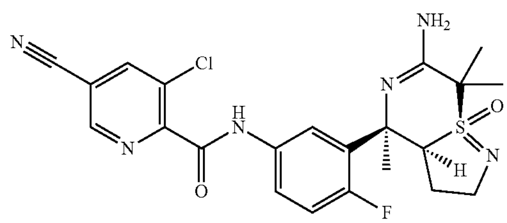 | 1.0 | 80 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3-chloro-5-cyanopicolinamide |
| 3AB | 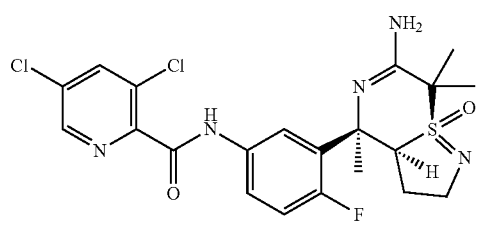 | 1.0 | 49 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3,5-dichloropicolinamide |
| 4AB | 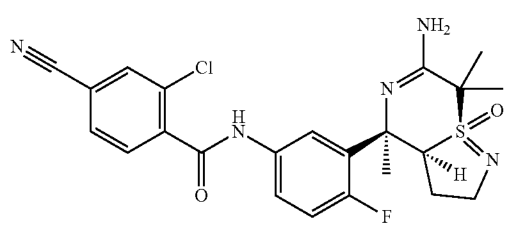 | 13.1 | 102 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-2-chloro-4-cyanobenzamide |
| 5AB | 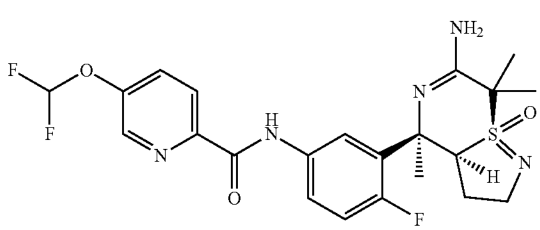 | 0.6 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(difluoromethoxy)picolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 6AB | 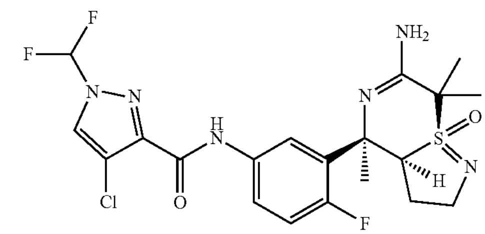 | 1.1 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-4-chloro-1-(difluoromethyl)-1H-pyrazole-3-carboxamide |
| 7AB | 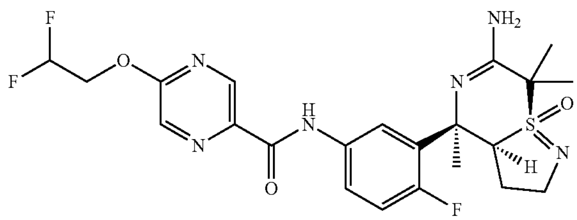 | 0.4 | 42 | N-(3((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(2,2-difluoroethoxy)pyrazine-2-carboxamide |
| 8AB | 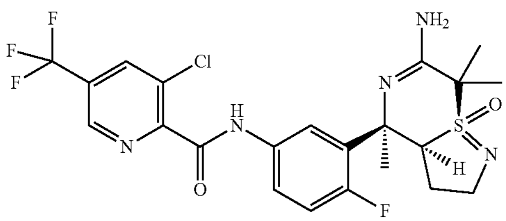 | 0.3 | | N-(3((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3-chloro-5-(trifluoromethyl)picolinamide |
| 9AB | 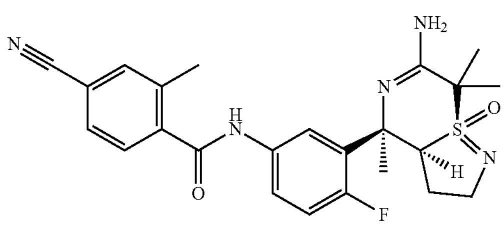 | 12.3 | | N-(3((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-4-cyano-2-methylbenzamide |
| 10AB | 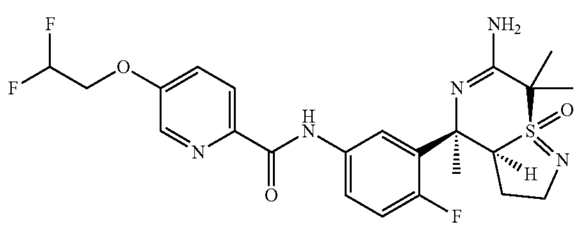 | 2.2 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(2,2-difluoroethoxy)picolinamide |
| 11AB | 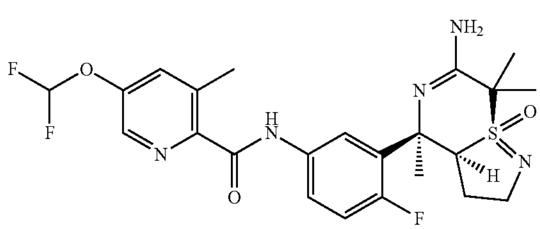 | 0.2 | | N-(3((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(difluoromethoxy)-3-methylpicolinamide |

TABLE 1-continued

Pharmacological data

| Ex. | Structure | BACE1 cell act. Aβ40 IC$^{50}$ [nM] | Aβ40 (wt mice, brain) [%] | Name |
|---|---|---|---|---|
| 12AB | 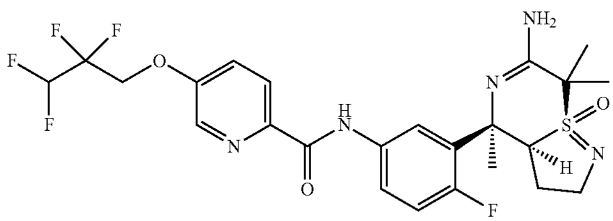 | 1.4 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(2,2,3,3-tetrafluoropropoxy)picolinamide |
| 13AB | 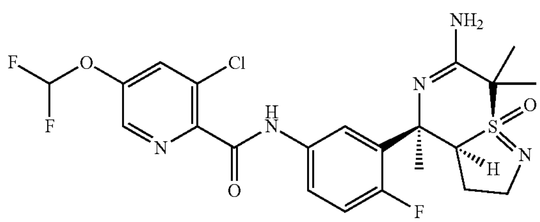 | 0.3 | 39 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3-chloro-5-(difluoromethoxy)picolinamide |
| 14AB | 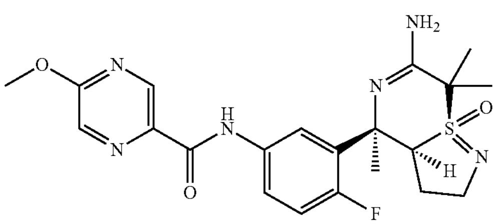 | 0.5 | 3 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-methoxypyrazine-2-carboxamide |
| 15AB | 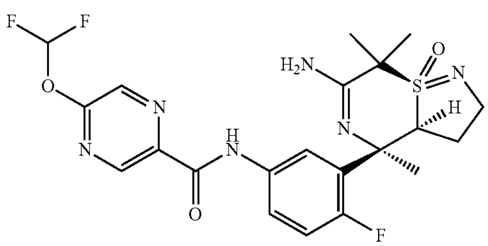 | 0.2 | 20 | N-(3-((3aS,4R,8R)-6-amino-4,7,7-trimethyl-8-oxido-3,3a,4,7-tetrahydro-2H-isothiazolo[1,5-1][1,4]thiazin-4-1)-4-fluorophenyl)-5-(difluoromethoxy)pyrazine-2-carboxamide |
| 16AB | 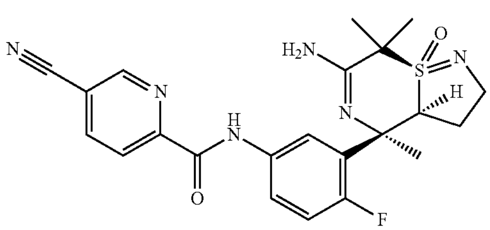 | 1,4 | 0.2 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-cyanopicolinamide |
| 17AB | 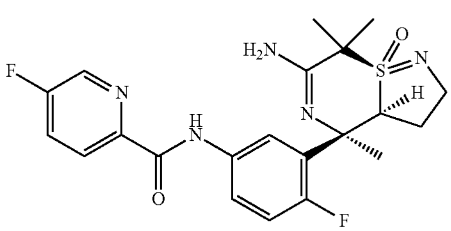 | 0.3 | 40 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-fluoropicolinamide |

TABLE 1-continued

Pharmacological data

| Ex. | Structure | BACE1 cell act. Aβ40 IC$^{50}$ [nM] | Aβ40 (wt mice, brain) [%] | Name |
|---|---|---|---|---|
| 18AB | 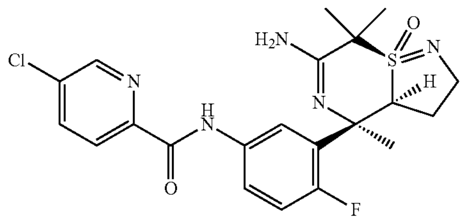 | 0.2 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-chloropicolinamide |
| 19AB | 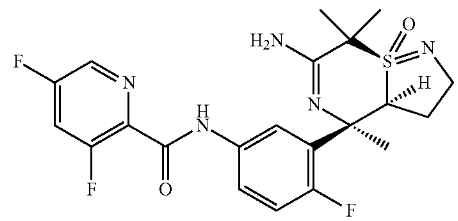 | 1.3 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3,5-difluoropicolinamide |
| 20AB | 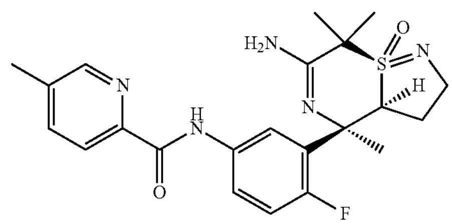 | 0.4 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-methylpicolinamide |
| 21AB | 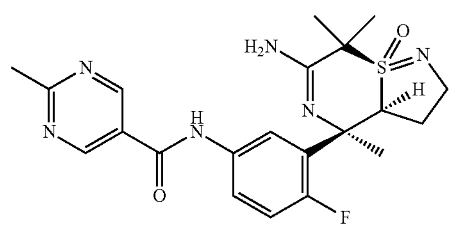 | 914 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-2-methylpyrimidine-5-carboxamide |
| 22AB | 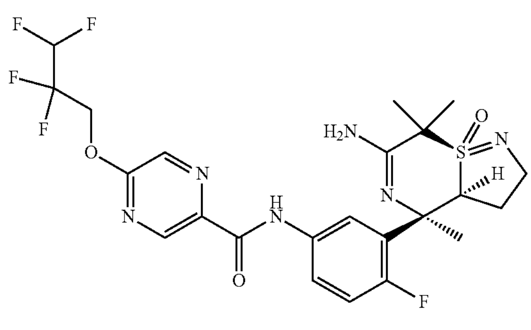 | 0.2 | 51 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-(2,2,3,3-tetrafluoropropoxy)pyrazine-2-carboxamide |
| 23AB | 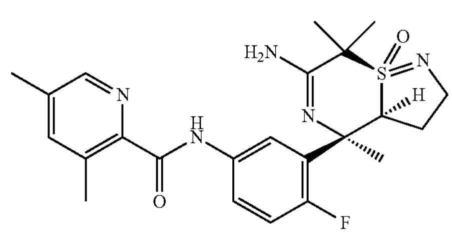 | 0.2 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-3,5-dimethylpicolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 24AB | 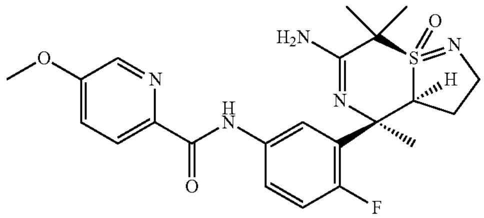 | 0.7 | | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-methoxypicolinamide |
| 25AB | 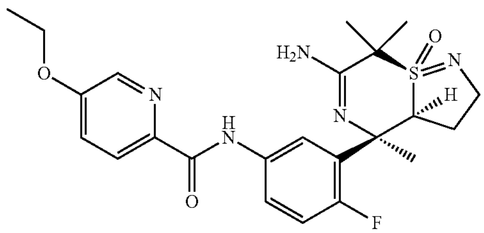 | 0.5 | 40 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-ethoxypicolinamide |
| 26AB | 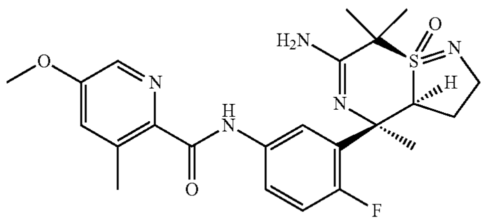 | 0.6 | 11 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-methoxy-3-methylpicolinamide |
| 27AB | 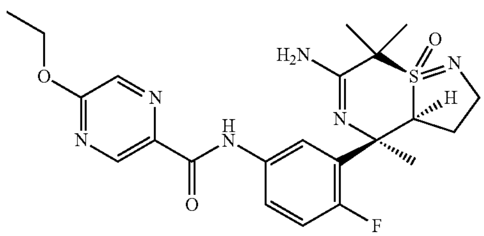 | 0.4 | 9 | N-(3-((3aS,4R,8R)-6-amino-4,7,7-trimethyl-8-oxido-3,3a,4,7-tetrahydro-2H-isothiazolo[1,5-1][1,4]thiazin-4-yl)-4-fluorophenyl)-5-ethoxypyrazine-2-carboxamide |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like.

Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool;

the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

Analytical Methods

Gas chromatograms (GC) were recorded using an Agilent 6850 Series II single channel GC system. Column: Agilent HP-1, 30 m×0.32 mm×0.25 µm film, SN USC174642H, PN 190917-413E; Carrier gas: Helium in constant flow mode, pressure 25 psi; nominal initial flow 7.8 mL/min, injection volume 1 µL; Inlet: Split (ratio 20:1); Detector: Temperature 300° C., hydrogen flow 30 mL/min, air flow 400 mL/min.

Oven Temperature Program:

| Time [min] | Start-Temp. [° C.] | Rate [° C./min] | End-Temperature [° C.] |
|---|---|---|---|
| 0.0 | 40 | 5.0 | 80 |
| 8.0 | 80 | 20.0 | 250 |
| 16.5 | -end of method- | | |

HPLC (method LCMS_fglm)

Column: Agilent Zorbax Eclipse Plus $C_{18}$, Rapid Resolution HT, 2.1×30 mm, 1.8 µm, Part. no. 959731-902

Solvent A: Water 0.01% Formic Acid; Solvent B: acetonitrile (MeCN)

Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

HPLC (method LCMS_gradient)

Column: Agilent Zorbax Eclipse Plus $C_{18}$, Rapid Resolution HT, 2.1×30 mm, 1.8 µm, Part. no. 959731-902

Solvent A: Water 0.01% Formic Acid; Solvent B: MeCN

Gradients:

| Time [min] | Flow Rate [ml/min] | % A | % B |
|---|---|---|---|
| Initial | 1.0 | 97 | 3 |
| 0.2 | 1.0 | 97 | 3 |
| 5.2 | 1.0 | 3 | 97 |
| 6.0 | 1.0 | 3 | 97 |
| 6.2 | 1.0 | 97 | 3 |

HPLC (method 7626L05)

Column: Agilent Poroshell 120 EC-C18, 4.6×50 mm, 2.7 µm, Part. no. 699975-902

Solvent A: MeCN; Solvent B: water/MeCN 95:5 v/v; Solvent C: solution of 1 g tetra n-butylammonium hydrogensulfate in 1 L of water/MeCN 1:4 v/v.

Gradients:

| Time [min] | Flow Rate [ml/min] | % A | % B | % C |
|---|---|---|---|---|
| Initial | 1.0 | 10 | 85 | 5 |
| 1.0 | 1.0 | 10 | 85 | 5 |
| 7.0 | 1.0 | 85 | 10 | 5 |
| 12.0 | 1.0 | 85 | 10 | 5 |
| 13.0 | 1.0 | 10 | 85 | 5 |

Abbreviations

The following abbreviations were used in the experimental part: THF, tetrahydrofurane; MTBE, methyl-tert-butylether; DMF, dimethylformamide; TLC, thin layer chromatography.

Intermediates

Synthesis of Int-5: 2-Methyl-2-(S-methylsulfonimidoyl)propanenitrile

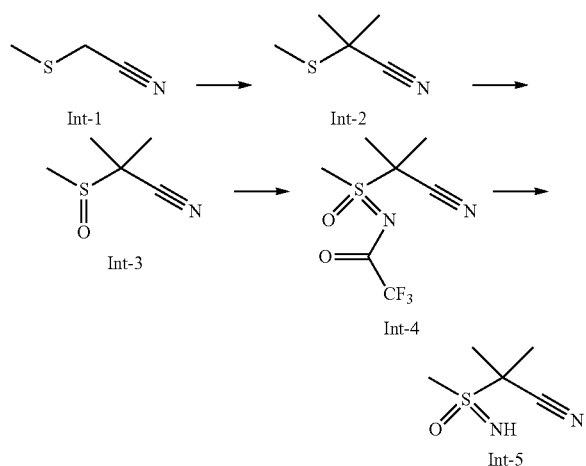

Step 1: 2-Methyl-2-methylsulfanyl-propanenitrile (Int-2)

Sodium hydride (24.0 g, 60% suspension in mineral oil, 600 mmol) was washed with n-heptane (3×100 mL) and suspended in THF (300 mL) at 0-5° C. A solution of 2-(methylthio)acetonitrile (Int-1, 20 g, 230 mmol) in THF (100 mL) was added and the resulting suspension was stirred for 15 min at 0-5° C. (ice bath). Then, a solution of methyl iodide (90.8 g, 40.0 mL, 640 mmol) in THF was added over 15 min. The mixture was allowed to warm and stirred for 3 h at room temperature. After that, the reaction mixture was poured carefully onto water (200 mL) and extracted with MTBE (1×500 mL, 3×150 mL). The combined extracts were washed with saturated aqueous sodium hydrogencarbonate solution (100 mL) and brine (100 mL), dried (sodium sulfate) and concentrated in vacuo to afford, after drying in vacuo (10 mbar, 40° C., 45 min), the title compound as a yellow oil (23.4 g, 89%), that was used in the next step without further purification. GC (method 7626G01) $t_R$=2.5 min. $^1$H NMR (CDCl$_3$, 400 MHz): δ 1.65 (s, 6H), 2.32 (s, 3H).

Step 2: 2-Methyl-2-methylsulfinyl-propanenitrile (Int-3)

2-Methyl-2-(methylthio)propanenitrile (Int-2, 23 g, 200 mmol) was dissolved in 1,4-dioxane (115 mL) and water (345 mL) was added. The emulsion was cooled to 0-5° C. (ice bath) and sodium periodate (44.8 g, 210 mmol) was added with water (115 mL). The resulting white suspension was warmed to room temperature and stirred vigorously for 16 h. Then, the mixture was filtered, the residue washed with ethyl acetate (400 mL). After phase separation of the filtrate, the aqueous phase was saturated with sodium chloride, extracted with ethyl acetate (5×200 mL). The combined extracts were washed with brine (100 mL), dried (sodium sulfate) and concentrated in vacuo to afford, after drying (50° C., 5 mbar), the title compound as yellow oil (25 g). The crude product was purified by column chromatography (silica gel, 100 g, eluting with ethyl acetate/n-heptane, gradient 50:50 to 0:100) to give the title compound as yellow oil (23.3 g, 89%). $^1$H NMR (CDCl$_3$, 400 MHz): δ 1.59 (s, 3H), 1.68 (s, 3H), 2.74 (s, 3H).

Step 3: 2-Methyl-2-(S-methylsulfon(trifluoracetylimidoyl))propanenitrile (Int-4)

2-Methyl-2-(methylsulfinyl)propanenitrile (Int-3, 9.8 g, 74.7 mmol) was dissolved in dichloromethane (390 mL) at 0-5° C. (ice bath) and 2,2,2-trifluoroacetamide (17.0 g, 151 mmol), magnesium oxide (12.7 g, 307 mmol) and rhodium (II) acetate dimer (850 mg, 1.92 mmol) were added subsequently. Finally, a solution of iodobenzene diacetate (36.3 g, 113 mmol) in dichloromethane (98.0 mL) was added and the mixture was stirred for 1 h at 0-5° C., followed by 6 h at room temperature. Then, a second portion of rhodium(II) acetate dimer (850 mg, 1.92 mmol) was added and the suspension stirred for additional 95 h at room temperature. The reaction mixture was filtered, the residue was washed with dichloromethane (100 mL) and the combined filtrate was concentrated in vacuo to afford a dark oil as crude product. After column chromatography (silica gel, 100 g, eluting with ethyl acetate/n-heptane, gradient 10:90 to 50:50) and drying in vacuo (50° C., 5 mbar) the title compound was isolated as a light yellow oil, that solidified upon standing (13.74 g, 76%). HPLC (method LCMS_fglm) $t_R$=0.97 min. $^1$H NMR (CDCl$_3$, 400 MHz): δ 1.91 (s, 3H), 1.91 (s, 3H), 3.65 (s, 3H). MS (ES−) m/z 241.1 [M−H].

Step 4: 2-Methyl-2-(S-methylsulfonimidoyl)propanenitrile (Int-5)

2-Methyl-2-(S-methylsulfon(trifluoracetylimidoyl))propanenitrile (Int-4, 9.90 g, 40.9 mmol) was dissolved in methanol (100 mL) at 0-5° C. (ice bath). Potassium carbonate (28.2 g, 204 mmol) was added with methanol (20 mL) and the resulting suspension was stirred at room temperature for 0.5 h. The reaction mixture was diluted with MTBE (250 mL) and silica gel (25 g) was added, the mixture was stirred for 15 min. After that, it was filtered over a plug of silica gel (35 g), the residue was washed with MTBE/methanol 2:1 (v/v, 250 mL). The combined filtrate was concentrated in vacuo to give a yellow oil. This material was again dissolved in ethyl acetate (200 mL) and filtered over a plug of silica gel (40 g), the residue was washed with ethyl acetate (200 mL). The combined filtrate was again concentrated in vacuo to afford the crude product as a yellow oil (5.98 g). The crude was purified by column chromatography (silica gel, 100 g, eluting with ethyl acetate/n-heptane, gradient 50:50 to 100:0) to yield, after drying in vacuo (50° C., 5 mbar), the title compound as a light yellow solid (4.54 g, 76%). GC (method 7626001) $t_R$=9.7 min. $^1$H NMR (CDCl$_3$, 400 MHz): δ 1.75 (s, 3H), 1.76 (s, 3H), 2.79 (br s, 1H), 3.15 (s, 3H).

Synthesis of Int-7: (R,E)-N-(1-(5-Bromo-2-fluoro-phenyl)ethylidene)-2-methylpropane-2-sulfinamide

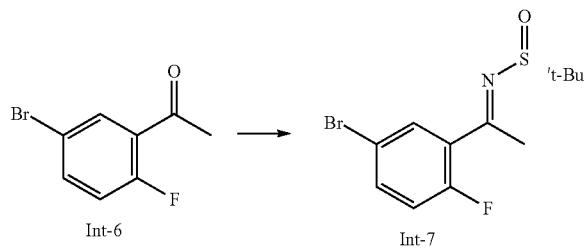

To a mixture of 1-(5-bromo-2-fluorophenyl)ethanone (22.5 g, 102 mmol) and (R)-2-methylpropane-2-sulfinamide (13.2 g, 107 mmol) in tetrahydrofuran (300 mL) was added titanium (IV) ethoxide (53.5 g, 49.6 mL, 235 mmol). The reaction mixture was heated for 17 h at 65° C. After that, the mixture was cooled to 40-45° C. and an aqueous solution of Rochelle salt (630 g/L, 200 mL) was added, the mixture was stirred for 1 h at 40-45° C. It was diluted with TBME (300 mL). After phase separation, the milky aqueous layer was extracted with TBME (2×200 mL), the combined organics were washed with an aqueous solution of sodium hydrogencarbonate (5% m/m, 250 mL) and brine (250 mL), dried over anhydrous sodium sulfate, filtrated and concentrated in vacuo. The crude was purified by column chromatography (silica gel, 330 g, eluting with ethyl acetate/n-heptane, gradient 5:95 to 45:55) to yield, after drying in vacuo (40° C., 5 mbar), the title compound (28.2 g, 86% yield) as a light brown solid. $^{1}$H NMR (CDCl$_{3}$, 300 MHz): δ 1.33 (s, 9H), 2.76 (d, J=3.4 Hz, 3H), 7.02 (dd, J=8.9, 10.7 Hz, 1H), 7.49-7.47 (m, 1H), 7.77 (dd, J=2.2, 6.3 Hz, 1H). MS (ES+) m/z 320.1 & 322.1 [M+H, Br].

Synthesis of Int-9: 2-Methyl-2-[S-methyl-N-(2-tetrahydropyran-2-yloxyethyl)sulfon-imidoyl]propanenitrile

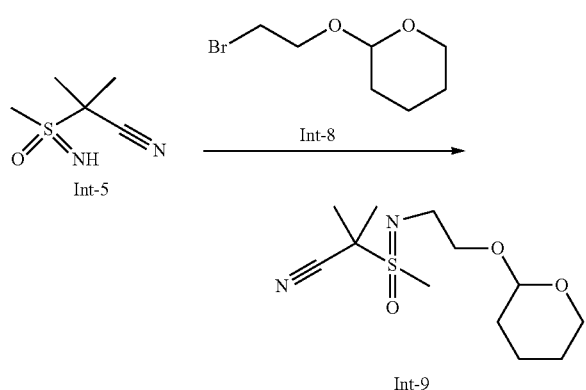

A suspension of potassium hydride (30% suspension in mineral oil, 54.7 g, 410.4 mmol) in DME (200.0 mL) was cooled to 0-5° C. (ice bath). Then a solution of 2-methyl-2-(methylsulfonimidoyl)propanenitrile (Int-5, 30.0 g, 205.2 mmol) in DME (100.0 mL) was added dropwise to the mixture. After that, the mixture was allowed to warm to 23° C. and stirred for 3 h. Then tetra-n-butylammonium bromide (3.3 g, 10.26 mmol) and 2-(2-bromoethoxy)tetrahydropyran (Int-8, 85.8 g, 410.4 mmol) in DME (100.0 mL) was added to the reaction mixture. The mixture was stirred at 23° C. for 16 h. After complete consumption of starting material had been detected by tlc, the mixture was poured into a saturated aqueous solution of sodium hydrogencarbonate (500 mL) and diluted with ethyl acetate (300 mL). After phase separation, the aqueous phase was extracted with ethyl acetate (2×200 mL), the combined organic extracts were dried over sodium sulfate, filtered and concentrated to give a crude product which was purified by column chromatography (silica gel, eluting with ethyl acetate/petroleum ether 50:50) to give the title compound as yellow oil (45.0 g, 80% yield). $^{1}$H NMR (CDCl$_{3}$, 400 MHz): δ 1.46-1.61 (m, 4H), 1.67-1.86 (m, 2H), 1.76 (s, 6H), 3.09 & 3.10 (2s, 3H, diast.), 3.31-3.54 (m, 4H), 3.77-3.91 (m, 2H), 4.60-4.64 (m, 1H).

Synthesis of Int-11A and Int-11B: 2-((R,2R)-2-Amino-2-(5-bromo-2-fluorophenyl)-N-(2-hydroxyethyl)propylsulfonimidoyl)-2-methylpropanenitrile (Int-11A) and 2-((S,2R)-2-amino-2-(5-bromo-2-fluorophenyl)-N-(2-hydroxyethyl)propylsulfonimidoyl)-2-methylpropanenitrile (Int-11B)

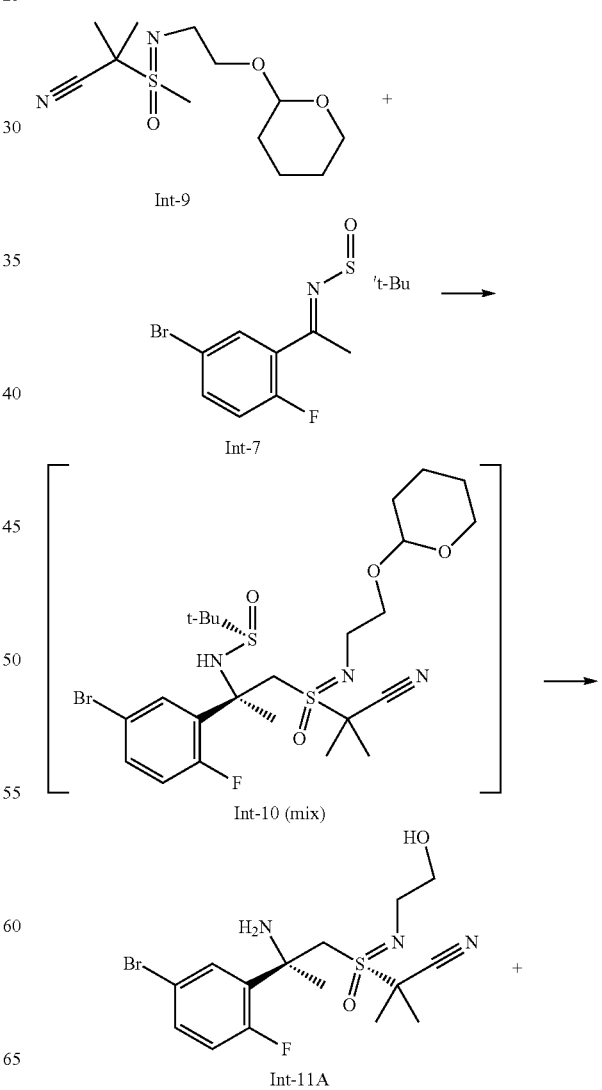

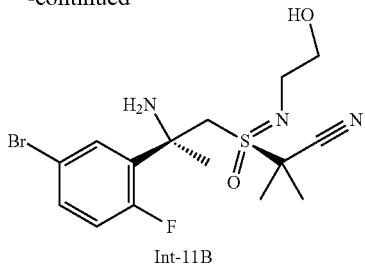

Int-11B

Step 1: (R)—N-((2R)-2-(5-Bromo-2-fluorophenyl)-1-(2-cyano-N-(2-((tetrahydro-2H-pyran-2-yl)oxy)ethyl)propan-2-ylsulfonimidoyl)propan-2-yl)-2-methylpropane-2-sulfinamide (Int-10 (mix))

To a solution of 2-methyl-2-[S-methyl-N-(2-tetrahydro-pyran-2-yloxyethyl)sulfon-imidoyl]propanenitrile (Int-9, 1.41 g, 5.14 mmol) in dichloromethane (20.0 mL) was added a solution of lithium hexamethyldisilazide in THF/ethylbenzene (1.0 M, 5.14 mL, 5.14 mmol) at −75° C. over 10 min, the mixture was stirred at −75° C. for 1 h. Then a solution of (R,E)-N-(1-(5-bromo-2-fluorophenyl)ethylidene)-2-methylpropane-2-sulfinamide (Int-7, 1.35 g, 4.22 mmol) in dichloromethane (8.0 mL) was added to the reaction mixture over 15 min. The resulting dark brown solution was stirred at −75° C. for 2 h. Then, the reaction mixture was quenched by addition of an aqueous saturated solution of ammonium chloride (50 mL), it was allowed to warm to 0° C. After phase separation, the aqueous phase was extracted with dichloromethane (2×50 mL), the combined organic layers were dried over sodium sulfate. After filtration, the filtrate was concentrated to give a crude product. The crude was purified by column chromatography (silica gel, 120 g, eluting with ethyl acetate/n-heptane, gradient 20:80 to 70:30) to yield, after drying in vacuo (40° C., 5 mbar), the title compound (1.75 g, 70% yield) as a light yellow, sticky foam and as a mixture of diastereoisomers. MS (ES+) m/z 510.3 & 512.3 [M+H−THP].

Step 2: 2-((R,2R)-2-Amino-2-(5-bromo-2-fluorophenyl)-N-(2-hydroxyethyl)propylsulfonimidoyl)-2-methylpropanenitrile (Int-11A) and 2-((S,2R)-2-amino-2-(5-bromo-2-fluorophenyl)-N-(2-hydroxyethyl)propylsulfonimidoyl)-2-methylpropanenitrile (Int-11B)

To a solution of (R)—N-((2R)-2-(5-Bromo-2-fluorophenyl)-1-(2-cyano-N-(2-((tetrahydro-2H-pyran-2-yl)oxy)ethyl)propan-2-ylsulfonimidoyl)propan-2-yl)-2-methylpropane-2-sulfinamide (Int-10 (mix), 1.75 g, 2.94 mmol) in ethanol (10 mL) was added a solution of hydrogen chloride in methanol/methyl acetate (ca. 20% m/m, 21.7 mL, 122 mmol), that had been prepared before by careful addition of acetyl chloride (9.59 g, 8.68 mL, 122 mmol) to methanol (13 mL) at −15-0° C. (ice/sodium chloride/ethanol bath), at 0° C. The reaction mixture was stirred for 30 min at 0° C. After that, the reaction mixture was poured into an aqueous solution of sodium carbonate (10% m/m, 125 mL), the pH was verified to be ca. 11. The mixture was extracted with ethyl acetate (2×60 mL). The combined organic layers were washed with brine (1×60 mL), dried over sodium sulfate, filtered and concentrated in vacuo. The crude was purified by column chromatography (silica gel, 80 g, eluting with 2 M ammonia in methanol/dichloromethane, gradient 2:98 to 5:95) to yield, after drying in vacuo (40° C., 5 mbar), the title compounds Int-11B (first eluting, 605 mg, 50%, colorless, viscous oil) and Int-11A (second eluting, 420 mg, 35%, colorless viscous oil) as separated diastereoisomers. The combined yield was 85%.

Int-11A: HPLC (method LCMS_gradient) $t_R$=0.97 min. $^1$H NMR (CDCl$_3$, 300 MHz): δ 1.67 (s, 3H), 1.68 (s, 3H), 1.70 (s, 3H), 2.42 (br s, 3H), 3.16-3.36 (m, 2H), 3.51-3.58 (m, 2H), 3.73 (d, J=13.5 Hz, 1H), 3.98 (d, J=13.5 Hz, 1H), 6.96 (dd, J=8.6, 11.8 Hz, 1H), 7.41 (ddd, J=2.4, 4.2, 8.6 Hz, 1H), 7.80 (dd, J=2.4, 7.3 Hz, 1H). MS (ES+) m/z 406.1 & 408.1 [M+H].

Int-11B: HPLC (method LCMS_gradient) $t_R$=0.89 min. $^1$H NMR (CDCl$_3$, 300 MHz): δ 1.67 (s, 3H), 1.70 (2s, 6H), 2.28 (br s, 3H), 2.99-3.09 (m, 1H), 3.13-3.22 (m, 2H), 3.29-3.38 (m, 1H), 3.59 (d, J=13.5 Hz, 1H), 4.11 (dd, J=1.2, 13.5 Hz, 1H), 6.96 (dd, J=8.5, 11.7 Hz, 1H), 7.42 (ddd, J=2.4, 4.2, 8.5 Hz, 1H), 7.81 (dd, J=2.4, 7.3 Hz, 1H). MS (ES+) m/z 406.1 & 408.1 [M+H].

Synthesis of Int-13A: tert-Butyl ((1R,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate

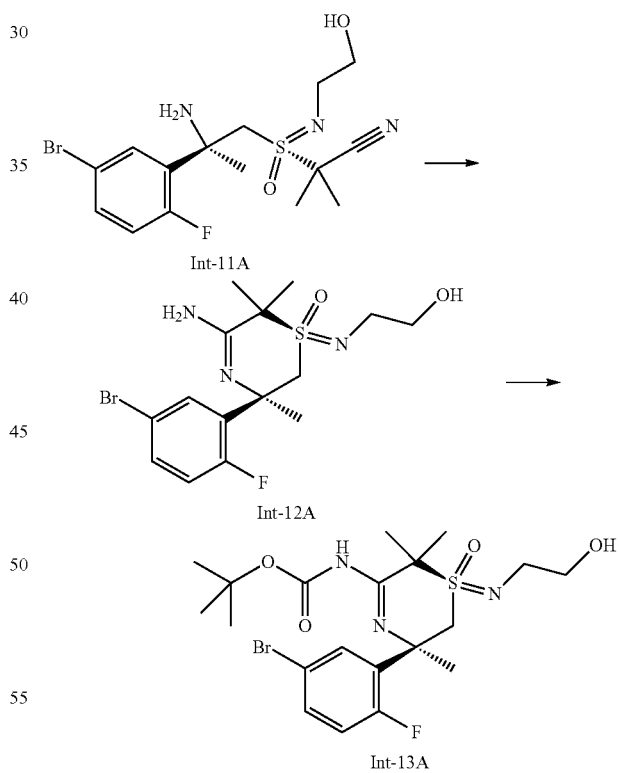

Step 1: (1R,3R)-5-Amino-3-(5-bromo-2-fluorophenyl)-1-((2-hydroxyethyl)imino)-3,6,6-trimethyl-3,6-dihydro-2H-1,4-thiazine 1-oxide (Int-12A)

To a solution of 2-((R,2R)-2-amino-2-(5-bromo-2-fluorophenyl)-N-(2-hydroxyethyl)-propylsulfonimidoyl)-2-methylpropanenitrile (Int-11A, 420 mg, 1.03 mmol) in ethanol (10 mL) was added copper(I) bromide (171 mg, 1.19 mmol). The mixture was stirred at 78° C. for 2 h. Then, the reaction mixture was allowed to cool to room temperature, poured into a mixture of water (80 mL) and ethyl acetate (80 mL). Aqueous ammonia (25% m/m, 5 mL) was added and the resulting mixture was stirred for 10 min. After phase separation, the aqueous layer was extracted with ethyl acetate (1×80 mL). The combined organics were dried over sodium sulfate, filtered and concentrated in vacuo to give the crude product as a sticky foam which was used in the next step without further purification (420 mg).

Step 2: tert-Butyl ((1R,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate (Int-13A)

To a suspension of (1R,3R)-5-amino-3-(5-bromo-2-fluorophenyl)-1-((2-hydroxyethyl)imino)-3,6,6-trimethyl-3,6-dihydro-2H-1,4-thiazine 1-oxide (Int-12A, crude from preceeding step, 420 mg, 1.03 mmol) in tetrahydrofuran (10 mL) and water (2.5 mL), solid sodium hydrogencarbonate (117 mg, 1.4 mmol), followed by Boc-anhydride (282 mg, 1.29 mmol) were added. The mixture was stirred at 22° C. for 17 h. The reaction mixture was diluted with an aqueous sodium carbonate solution (10% m/m, 30 mL) and extracted with ethyl acetate (2×50 mL). The combined extracts were washed with brine (1×50 mL), dried over sodium sulfate, filtered and concentrated in vacuo. The crude was purified by column chromatography (silica gel, 24 g, eluting with ethyl acetate/n-heptane, gradient 35:65 to 75:25) to yield, after drying in vacuo (40° C., 5 mbar), the title compound (300 mg, 57% yield over two steps) as colorless, viscous oil. HPLC (method LCMS_fglm) $t_R$=1.26 min. MS (ES+) m/z 506.3 & 508.3 [M+H].

Synthesis of Int-16AB: tert-Butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate

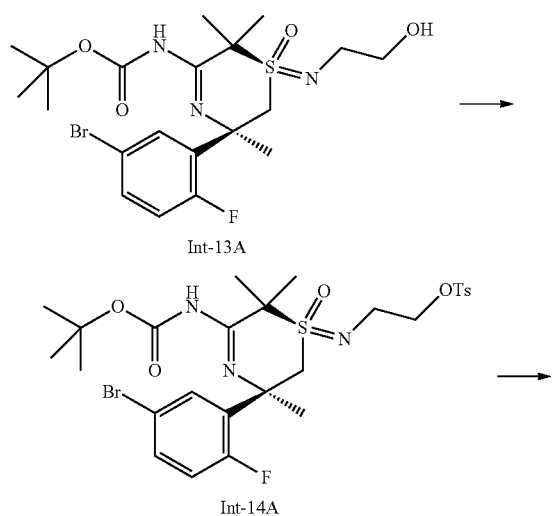

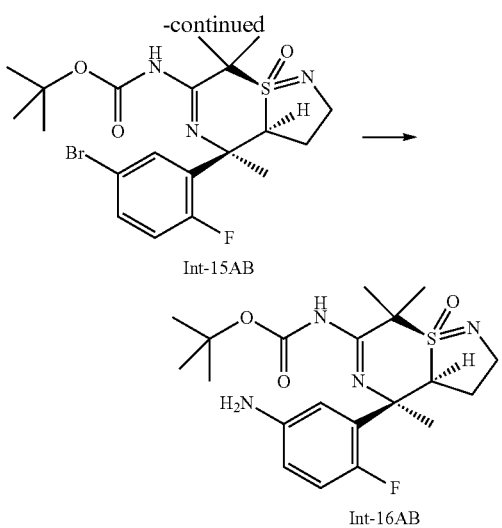

Step 1: 2-(((1R,3R)-3-(5-Bromo-2-fluorophenyl)-5-((tert-butoxycarbonyl)amino)-3,6,6-trimethyl-1-oxido-3,6-dihydro-2H-1,4-thiazin-1-ylidene)amino) ethyl 4-methylbenzenesulfonate (Int-14A)

tert-Butyl ((1R,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate (Int-13A, 407 mg, 804 μmol) was dissolved in dichloromethane (10 mL) and the solution was cooled to 0-5° C. (ice bath). Triethylamine (163 mg, 224 μL, 1.61 mmol) and 4-(dimethylamino)-pyridine (4.9 mg, 40 μmol) were added at 0° C., followed by tosyl chloride (184 mg, 964 μmol). The resulting colorless solution was stirred at room temperature for 16 h. After that, the mixture was concentrated in vacuo to give the crude product. The crude was purified by column chromatography (silica gel, 24 g, eluting with ethyl acetate/n-heptane, gradient 10:90 to 65:35) to yield, after drying in vacuo (40° C., 5 mbar), the title compound as a white foam (400 mg, 72% yield). HPLC (method LCMS_gradient) $t_R$=3.7 min. $^1$H NMR (CDCl$_3$, 300 MHz): δ 1.53 (s, 3H), 1.57 (s, 9H), 1.72 (s, 3H), 1.84 (s, 3H), 2.37-2.47 (m, 1H), 2.45 (s, 3H), 2.95-3.05 (m, 1H), 3.57-3.70 (m, 1H), 3.66 (d, J=15.3 Hz, 1H), 3.72-3.81 (m, 1H), 3.93 (d, J=15.3 Hz, 1H), 7.01 (dd, J=8.6, 11.8 Hz, 1H), 7.30-7.38 (m, 3H), 7.40-7.46 (m, 1H), 7.75 (d, J=8.3 Hz, 2H), 10.89 (s, 1H). MS (ES+) m/z 660.4 & 662.4 [M+H].

Step 2: tert-Butyl ((3aS,4R,8R)-4-(5-bromo-2-fluorophenyl)-4,7,7-trimethyl-8-oxido-3,3a,4,7-tetrahydro-2H-isothiazolo[1,5-a][1,4]thiazin-6-yl)carbamate (Int-15AB)

To a solution of 2-(((1R,3R)-3-(5-bromo-2-fluorophenyl)-5-((tert-butoxycarbonyl)amino)-3,6,6-trimethyl-1-oxido-3,6-dihydro-2H-1,4-thiazin-1-ylidene)amino)ethyl 4-methylbenzenesulfonate (Int-14A, 360 mg, 545 μmol) in dry THF (6 mL) a solution of lithium hexamethyldisilazide in THF/ethylbenzene (1 M, 1.63 mL, 1.63 mmol) was added dropwise at −75° C. over 10 min. Then, the yellow solution was allowed to warm to −20° C. (ice/ethanol/sodium chloride bath) and stirred for 1 h. After that, the reaction was quenched by addition of an aqueous saturated ammonium chloride solution (10 mL) and water (30 mL), and extracted with ethyl acetate (2×50 mL). The combined extracts were washed with brine (50 mL), dried over sodium sulfate and concentrated in vacuo to give the crude product. The crude was purified by column chromatography (silica gel, 12 g, eluting with ethyl acetate/n-heptane, gradient 25:75 to 100:0) to yield, after drying in vacuo (40° C., 5 mbar), the title compound (140 mg, 51% yield) as a brownish foam. HPLC (method LCMS_gradient) $t_R$=2.9 min. MS (ES+) m/z 488.3 & 490.3 [M+H].

Step 3: tert-Butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16AB)

tert-Butyl ((3aS,4R,8R)-4-(5-bromo-2-fluorophenyl)-4,7,7-trimethyl-8-oxido-3,3a,4,7-tetrahydro-2H-isothiazolo[1,5-a][1,4]thiazin-6-yl)carbamate (Int-14AB, 137 mg, 280 µmol) was dissolved in ethanol (2.4 mL) and water (1 mL) and sodium azide (146 mg, 2.24 mmol), copper(I) iodide (21.4 mg, 112 µmol), sodium ascorbate (22.2 mg, 112 µmol), and trans-N,N'-dimethyl-1,2-cyclohexanediamine (31.9 mg, 224 µmol) were added. The green mixture was stirred for 45 min at 70° C. Then, the reaction mixture was cooled to room temperature and additional sodium azide (146 mg, 2.24 mmol), copper(I) iodide (21.4 mg, 112 µmol), sodium ascorbate (22.2 mg, 112 µmol), and trans-N,N'-dimethyl-1,2-cyclohexanediamine (31.9 mg, 224 µmol) were added. The mixture was stirred for 1 h at 70° C. After that, all starting material was consumed. The reaction mixture was diluted with water (40 mL) and aqueous sodium carbonate solution (10% m/m, 10 mL) and extracted with ethyl acetate (2×50 mL). The combined organic layers were washed with brine (1×30 mL), dried over sodium sulfate, filtered and concentrated to give the crude product. The crude was dissolved in THF (6 mL) and water (2 mL), a solution of trimethylphosphine in THF (1 M, 280 µL, 280 µmol) was added and the mixture was stirred for 45 min at room temperature. Then, the mixture was diluted with water (30 mL), and dichloromethane (50 mL). After phase separation, the aqueous layer was extracted with dichloromethane (2×50 mL), the combined organics were dried over sodium sulfate, filtered and concentrated in vacuo. The crude was purified by column chromatography (silica gel, 12 g, eluting with ethyl acetate/n-heptane, gradient 45:55 to 100:0, followed by ethyl acetate/methanol 19:1) to yield, after drying in vacuo (40° C., 5 mbar), the title compound (80 mg, 65% yield) as a light yellow solid. HPLC (method LCMS_gradient) $t_R$=1.95 min. $^1$H NMR (CDCl$_3$, 300 MHz): δ 1.56 (s, 9H), 1.71-1.81 (m, 1H), 1.74 (s, 3H), 1.86 (s, 3H), 2.09-2.22 (m, 1H), 2.10 (s, 3H), 3.42-3.51 (m, 1H), 3.65-3.79 (m, 1H), 4.05-4.15 (m, 1H), 6.58-6.66 (m, 1H), 6.78-6.87 (m, 1H), 6.92 (dd, J=8.7, 12.1 Hz, 1H), 11.39 (s, 1H). MS (ES+) m/z 425.3 [M+H].

Synthesis of Int-16ABp: Enantiopure tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate

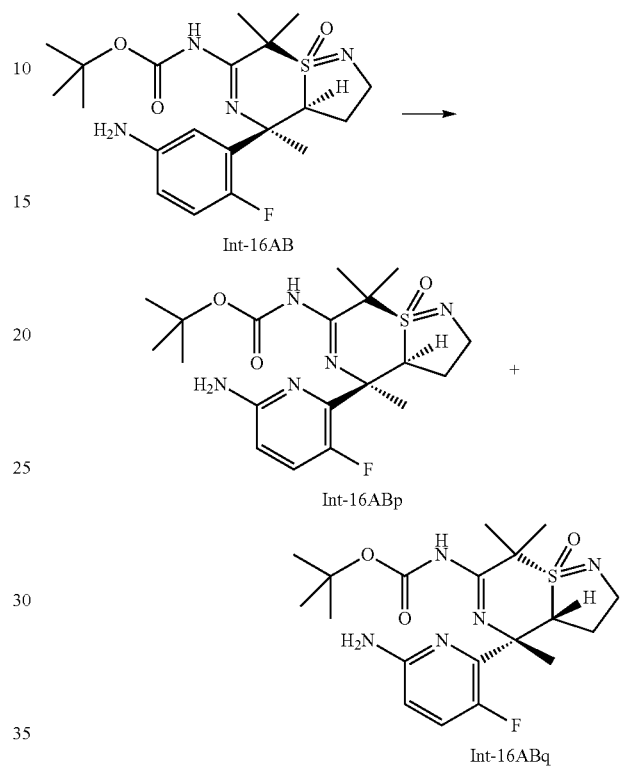

Enantiomeric purification of tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16AB, 1.30 g, 3.06 mmol, e.r. 94:6) was performed by chiral preparative HPLC (Reprosil Chiral NR, 250*4.6 mm*5 µm, isocratic, n-heptane/(ethanol+0.01% ammonium acetate) 80/20, flow 1.0 mL/min) to yield the desired (−)-rotating first eluting enantiomer as an off-white solid (Int-16ABp, 1.00 g, 77%, e.r. >99.5:0.5).

Synthesis of Int-13B: tert-Butyl ((1S,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate

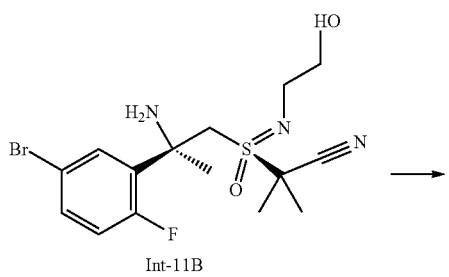

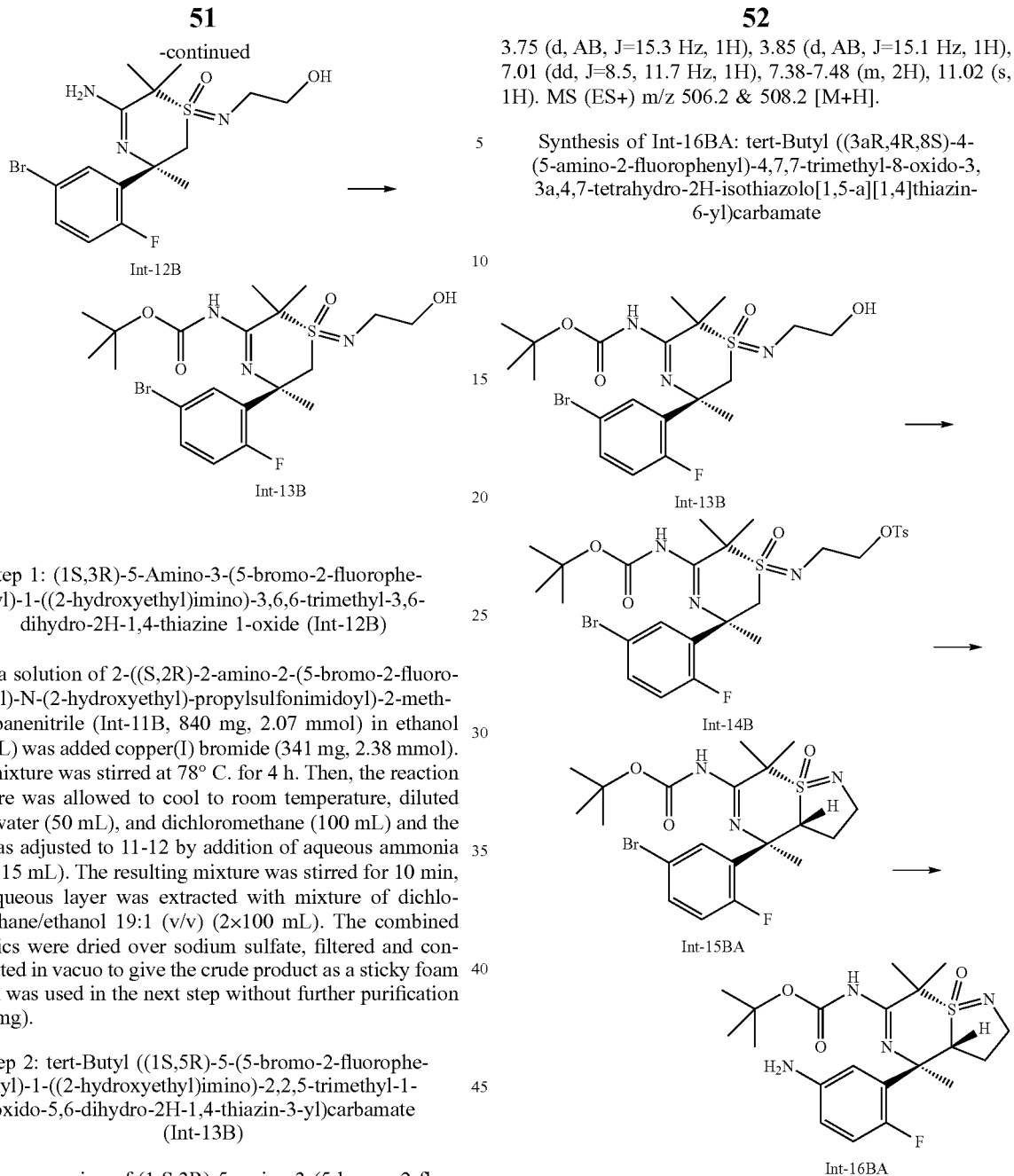

Step 1: (1S,3R)-5-Amino-3-(5-bromo-2-fluorophenyl)-1-((2-hydroxyethyl)imino)-3,6,6-trimethyl-3,6-dihydro-2H-1,4-thiazine 1-oxide (Int-12B)

To a solution of 2-((S,2R)-2-amino-2-(5-bromo-2-fluorophenyl)-N-(2-hydroxyethyl)-propylsulfonimidoyl)-2-methylpropanenitrile (Int-11B, 840 mg, 2.07 mmol) in ethanol (12 mL) was added copper(I) bromide (341 mg, 2.38 mmol). The mixture was stirred at 78° C. for 4 h. Then, the reaction mixture was allowed to cool to room temperature, diluted with water (50 mL), and dichloromethane (100 mL) and the pH was adjusted to 11-12 by addition of aqueous ammonia (2 M, 15 mL). The resulting mixture was stirred for 10 min, the aqueous layer was extracted with mixture of dichloromethane/ethanol 19:1 (v/v) (2×100 mL). The combined organics were dried over sodium sulfate, filtered and concentrated in vacuo to give the crude product as a sticky foam which was used in the next step without further purification (850 mg).

Step 2: tert-Butyl ((1S,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate (Int-13B)

To a suspension of (1 S,3R)-5-amino-3-(5-bromo-2-fluorophenyl)-1-((2-hydroxyethyl)imino)-3,6,6-trimethyl-3,6-dihydro-2H-1,4-thiazine 1-oxide (Int-12B, crude from preceeding step, 850 mg, 2.07 mmol) in tetrahydrofuran (25 mL) and water (5 mL), solid sodium hydrogencarbonate (234 mg, 2.79 mmol), followed by Boc-anhydride (564 mg, 2.58 mmol) were added. The mixture was stirred at 22° C. for 17 h. The reaction mixture was diluted with an aqueous sodium hydrogencarbonate solution (5% m/m, 50 mL) and extracted with ethyl acetate (2×80 mL). The combined extracts were dried over sodium sulfate, filtered and concentrated in vacuo. The crude was purified by column chromatography (silica gel, 40 g, eluting with ethyl acetate/n-heptane, gradient 40:60 to 100:0) to yield, after drying in vacuo (40° C., 5 mbar), the title compound (545 mg, 52% yield over two steps) as a waxy solid. HPLC (method LCMS_gradient) $t_R$=2.7 min. $^1$H NMR (CDCl$_3$, 300 MHz): δ 1.57 (s, 9H), 1.67 (s, 3H), 1.76 (s, 3H), 1.87 (s, 3H), 2.34 (t, J=6.3 Hz, 1H), 3.29-3.34 (m, 2H), 3.62-3.69 (m, 2H), 3.75 (d, AB, J=15.3 Hz, 1H), 3.85 (d, AB, J=15.1 Hz, 1H), 7.01 (dd, J=8.5, 11.7 Hz, 1H), 7.38-7.48 (m, 2H), 11.02 (s, 1H). MS (ES+) m/z 506.2 & 508.2 [M+H].

Synthesis of Int-16BA: tert-Butyl ((3aR,4R,8S)-4-(5-amino-2-fluorophenyl)-4,7,7-trimethyl-8-oxido-3,3a,4,7-tetrahydro-2H-isothiazolo[1,5-a][1,4]thiazin-6-yl)carbamate Step 1: 2-(((1S,3R)-3-(5-Bromo-2-fluorophenyl)-5-((tert-butoxycarbonyl)amino)-3,6,6-trimethyl-1-oxido-3,6-dihydro-2H-1,4-thiazin-1-ylidene)amino) ethyl 4-methylbenzenesulfonate (Int-14B)

tert-Butyl ((1 S,5R)-5-(5-bromo-2-fluorophenyl)-1-((2-hydroxyethyl)imino)-2,2,5-trimethyl-1-oxido-5,6-dihydro-2H-1,4-thiazin-3-yl)carbamate (Int-13B, 500 mg, 987 μmol) was dissolved in dichloromethane (10 mL) and the solution was cooled to 0-5° C. (ice bath). Triethylamine (200 mg, 275 μL, 1.97 mmol) and 4-(dimethylamino)-pyridine (6.0 mg, 49 μmol) were added at 0° C., followed by tosyl chloride (226 mg, 1.18 mmol). The resulting colorless solution was stirred at room temperature for 16 h. After that, the mixture was concentrated in vacuo to give the crude product. The crude was purified by column chromatography (silica gel, 40 g, eluting with ethyl acetate/n-heptane, gradient 10:90 to 60:40) to yield, after drying in vacuo (40° C., 5 mbar), the title compound (495 mg, 76% yield) as a white foam. HPLC (method LCMS_gradient) $t_R$=3.7 min. $^1$H NMR (CDCl$_3$, 300 MHz): δ 1.57 (s, 9H), 1.60 (s, 3H), 1.67 (s, 3H), 1.84 (s, 3H), 2.46 (s, 3H), 3.28-3.45 (m, 2H), 3.64 (d, J=15.3 Hz, 1H), 3.81 (d, J=15.1 Hz, 1H), 4.07 (t, J=6.0 Hz, 2H), 7.00 (dd, J=8.5, 11.7 Hz, 1H), 7.32-7.47 (m, 2H), 7.35 (d, J=8.1 Hz, 2H), 7.79 (d, J=8.3 Hz, 2H), 11.00 (s, 1H). MS (ES+) m/z 660.3 & 662.3 [M+H].

Step 2: tert-Butyl ((3aR,4R,8S)-4-(5-bromo-2-fluorophenyl)-4,7,7-trimethyl-8-oxido-3,3a,4,7-tetrahydro-2H-isothiazolo[1,5-a][1,4]thiazin-6-yl)carbamate (Int-15BA)

To a solution of 2-(((1 S,3R)-3-(5-bromo-2-fluorophenyl)-5-((tert-butoxycarbonyl)amino)-3,6,6-trimethyl-1-oxido-3,6-dihydro-2H-1,4-thiazin-1-ylidene)amino)ethyl 4-methylbenzenesulfonate (Int-14B, 490 mg, 742 µmol) in dry THF (10 mL) a solution of lithium hexamethyldisilazide (LHMDS) in THF (1 M, 2.23 mL, 2.23 mmol) was added dropwise at –75° C. over 5 min. Then, the yellow solution was allowed to warm to –15° C. (ice/ethanol/sodium chloride bath) and stirred for 1 h. After that, the reaction mixture was poured into an aqueous saturated ammonium chloride solution (40 mL) and extracted with ethyl acetate (2×50 mL). The combined extracts were washed with brine (50 mL), dried over sodium sulfate and concentrated in vacuo to give the crude product. The crude was purified by column chromatography (silica gel, 12 g, eluting with ethyl acetate/n-heptane, gradient 30:70 to 100:0) to yield, after drying in vacuo (40° C., 5 mbar), the title compound (312 mg, 85% yield) as an off-white solid. HPLC (method LCMS_gradient) $t_R$=2.7 min. $^1$H NMR (CDCl$_3$, 300 MHz): δ 1.12 (s, 3H), 1.56 (s, 9H), 1.73 (s, 3H), 1.75 (s, 3H), 2.12-2.28 (m, 1H), 2.56-2.67 (m, 1H), 3.68-3.86 (m, 2H), 4.38-4.47 (m, 1H), 7.05 (dd, J=8.7, 11.9 Hz, 1H), 7.49 (ddd, J=2.4, 4.2, 8.7 Hz, 1H), 7.59 (dd, J=2.4, 7.3 Hz, 1H), 11.02 (s, 1H). MS (ES+) m/z 488.2 & 490.2 [M+H].

Step 3: tert-Butyl ((3aR,4R,8S)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16BA)

tert-Butyl ((3aR,4R,8S)-4-(5-bromo-2-fluorophenyl)-4,7,7-trimethyl-8-oxido-3,3a,4,7-tetrahydro-2H-isothiazolo[1,5-a][1,4]thiazin-6-yl)carbamate (Int-15BA, 255 mg, 522 µmol) was suspended in ethanol (4.5 mL) and water (2 mL) and sodium azide (272 mg, 4.18 mmol), copper(I) iodide (39.8 mg, 209 µmol), sodium ascorbate (41.4 mg, 209 µmol), and trans-N,N'-dimethyl-1,2-cyclohexanediamine (59.4 mg, 418 µmol) were added. The dark blue mixture was stirred for 45 min at 70° C. Then, the reaction mixture was cooled to room temperature and additional sodium azide (272 mg, 4.18 mmol), copper(I) iodide (39.8 mg, 209 µmol), sodium ascorbate (41.4 mg, 209 µmol), and trans-N,N'-dimethyl-1,2-cyclohexanediamine (59.4 mg, 418 µmol) were added. The mixture was stirred for 1 h at 70° C. After that, all starting material was consumed. The reaction mixture was diluted with water (60 mL) and aqueous sodium carbonate solution (10% m/m, 30 mL) and extracted with ethyl acetate (2×80 mL). The combined organic layers were washed with brine (1×50 mL), dried over sodium sulfate, filtered and concentrated to give the crude product (302 mg). The crude was dissolved in THF (6 mL) and water (2 mL), a solution of trimethylphosphine in THF (1 M, 574 µL, 574 µmol) was added and the mixture was stirred for 1 h at room temperature. Then, the mixture was diluted with water (60 mL), and dichloromethane (80 mL). After phase separation, the aqueous layer was extracted with dichloromethane (3×60 mL), the combined organics were dried over sodium sulfate, filtered and concentrated in vacuo. The crude was purified by column chromatography (silica gel, 12 g, eluting with ethyl acetate/n-heptane, gradient 45:55 to 100:0, followed by ethyl acetate/methanol 19:1) to yield, after drying in vacuo (40° C., 5 mbar), the title compound (202 mg, 90% yield) as a light yellow foam. HPLC (method LCMS_gradient) $t_R$=2.0 min. $^1$H NMR (CDCl$_3$, 300 MHz): δ $^1$H NMR (CDCl$_3$, 300 MHz): δ 1.12 (s, 3H), 1.55 (s, 9H), 1.71 (s, 3H), 1.74 (s, 3H), 2.10-2.26 (m, 1H), 2.54-2.64 (m, 1H), 3.66 (br s, 2H), 3.67-3.84 (m, 2H), 4.43 (ddd, J=1.7, 6.6, 10.5 Hz, 1H), 6.61 (ddd, J=2.8, 3.6, 8.6 Hz, 1H), 6.76 (dd, J=2.8, 6.9 Hz, 1H), 6.92 (dd, J=8.7, 12.1 Hz, 1H), 10.95 (s, 1H). MS (ES+) m/z 425.3 [M+H].

Examples

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide (1AB)

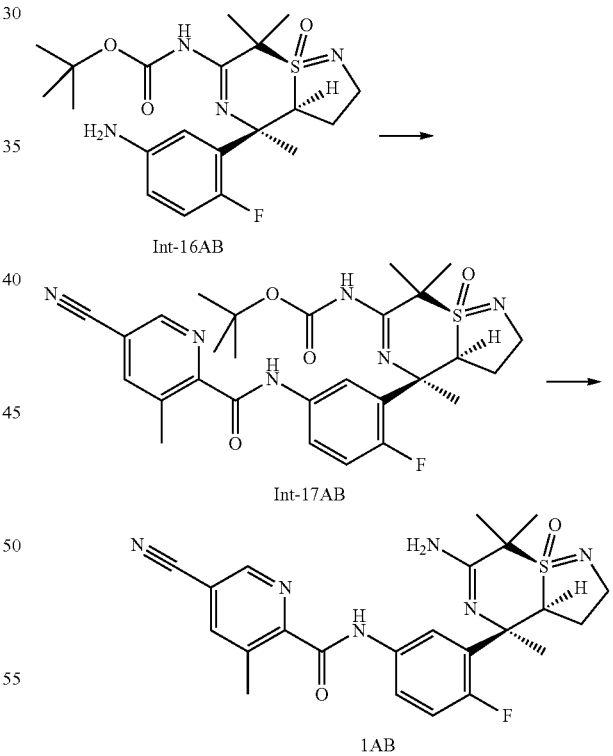

Step 1: tert-Butyl ((3aS,4R,8R)-4-(5-(5-cyano-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-17AB)

5-Cyano-3-methylpicolinic acid (49.3 mg, 304 µmol) was suspended in dichloromethane (5 mL), the suspension was cooled to 0-5° C. (ice bath) and oxalyl chloride (54.3 mg, 37.5 µL, 428 µmol) as well as dimethylformamide (0.308 M in toluene, 29 µL, 9 µmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 5-cyano-3-methylpicolinoyl chloride as red oil (54.8 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16AB, 76 mg, 179 µmol) was dissolved in dichloromethane (5 mL), the solution cooled to 10° C. and N,N-diisopropylethylamine (31 mg, 42 µL, 242 µmol) was added, followed by a solution of 5-cyano-3-methylpicolinoyl chloride (vide supra, 40.4 mg, 223 µmol) in dichloromethane (7.5 mL). The reaction mixture was stirred for 15 min at room temperature. Then, methanol (3 mL) was added, the mixture was stirred for 10 min at room temperature and concentrated in vacuo. The crude was purified by column chromatography (silica gel, 12 g, eluting with ethyl acetate/n-heptane, gradient 25:75 to 100:0) to yield, after drying in vacuo (40° C., 5 mbar), the title compound as a light brown foam (96 mg, 94%). HPLC (method LCMS_fglm) $t_R$=1.29 min. MS (ES+) m/z 569.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide (1AB)

tert-Butyl ((3aS,4R,8R)-4-(5-(5-cyano-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-17AB, 96 mg, 169 µmol) was dissolved in dichloromethane (5 mL) and trifluoroacetic acid (408 mg, 276 µL, 3.58 mmol) was added. The solution was stirred for 17 h at room temperature. After that, the mixture was concentrated in vacuo, the residue was redissolved in methanol (5 mL), aqueous ammonia (25% m/m, 200 µL) was added, stirred for 5 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a light brown solid (54 mg, 68% yield) as a mixture of enantiomers (e.r. 96:4 in favour of title compound), that can be separated by chiral preparative HPLC (Reprosil Chiral NR, 250*4.6 mm*5 µm, isocratic, n-heptane/(ethanol+ 0.01% ammonium acetate) 60/40, flow 1.0 mL/min). HPLC (method LCMS_gradient) $t_R$=1.27 min. ¹H NMR (CDCl₃, 300 MHz): δ 1.49-1.68 (m, 1H), 1.77 (s, 3H), 1.88 (s, 3H), 1.92-2.03 (m, 1H), 1.93 (s, 3H), 2.88 (s, 3H), 3.41 (dd, J=7.2, 10.4 Hz, 1H), 3.64 (ddd, J=4.9, 10.6, 10.6 Hz, 1H), 4.25 (ddd, J=1.2, 7.1, 12.3 Hz, 1H), 4.66 (br s, 2H), 7.08 (dd, J=8.7, 11.7 Hz, 1H), 7.88-7.98 (m, 2H), 8.18 (dd, J=2.8, 7.1 Hz, 1H), 8.73 (d, J=2.0 Hz, 1H), 10.05 (s, 1H). MS (ES+) m/z 469.4 [M+H].

N-(3-((3aR,4R,8S)-6-Amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpcolinamide (1BA)

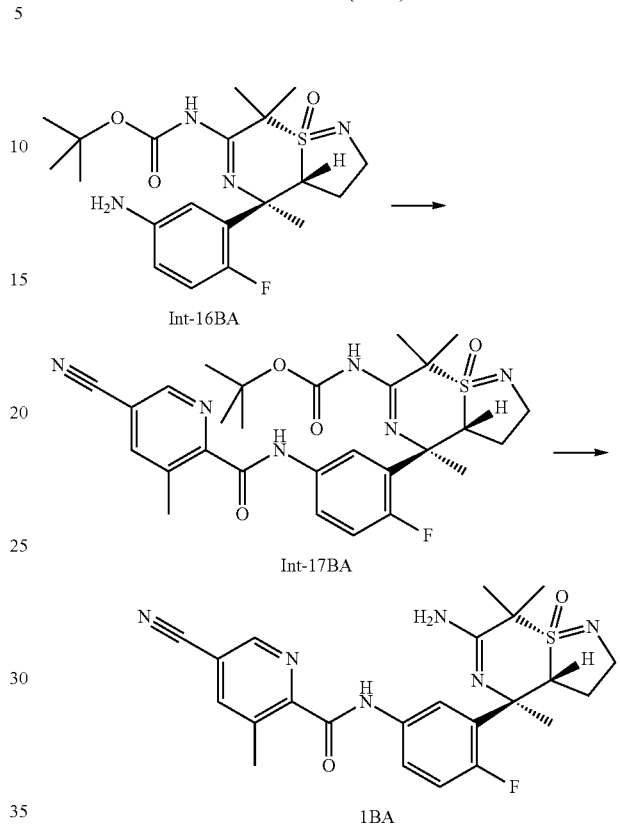

Step 1: tert-Butyl ((3aR,4R,8S)-4-(5-(5-cyano-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-17BA)

5-Cyano-3-methylpicolinic acid (64.9 mg, 400 µmol) was suspended in dichloromethane (5 mL), the suspension was cooled to 0-5° C. (ice bath) and oxalyl chloride (71.5 mg, 49.3 µL, 563 µmol) as well as dimethylformamide (0.308 M in toluene, 38 µL, 11 µmol) were added. The mixture was stirred for 90 min at room temperature. Then, it was concentrated in vacuo (40° C., 5 mbar) and dried azeotropically by two cycles of addition of toluene (3 mL) followed by concentration in vacuo to afford 5-cyano-3-methylpicolinoyl chloride as red oil (72.2 mg, quant.). After that, tert-butyl ((3aR,4R,8S)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16BA, 100 mg, 236 µmol) was dissolved in dichloromethane (5 mL), the solution cooled to 10° C. and N,N-diisopropylethylamine (41 mg, 55 µL, 318 µmol) was added, followed by a solution of 5-cyano-3-methylpicolinoyl chloride (vide supra, 53 mg, 295 µmol) in dichloromethane (7 mL). The reaction mixture was stirred for 15 min at 10-15° C. Then, methanol (3 mL) was added, the mixture was stirred for 1 h at room temperature and concentrated in vacuo. The crude was purified by column chromatography (silica gel, 12 g, eluting with ethyl acetate/ n-heptane, gradient 25:75 to 100:0) to yield, after drying in vacuo (40° C., 5 mbar), the title compound as a light brown viscous oil (121 mg, 90%). HPLC (method LCMS_fglm) $t_R$=1.27 min. MS (ES+) m/z 569.4 [M+H].

Step 2: N-(3-((3aR,4R,8S)-6-Amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide (1BA)

tert-Butyl ((3aR,4R,8S)-4-(5-(5-cyano-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-17BA, 121 mg, 213 µmol) was dissolved in dichloromethane (8 mL) and trifluoroacetic acid (537 mg, 363 µL, 4.71 mmol) was added. The solution was stirred for 17 h at room temperature. After that, the mixture was concentrated in vacuo, the residue was redissolved in methanol (5 mL), aqueous ammonia (25% m/m, 250 µL) was added, stirred for 5 min at room temperature, and concentrated in vacuo. The crude was purified by column chromatography (silica gel, 24 g, eluting with 2 M ammonia in methanol/dichloromethane, gradient 2:98 to 8:92) to yield, after drying in vacuo (40° C., 5 mbar), the title compound as a light brown solid (78 mg, 70% yield) as single enantiomer (after screen of chiral HPLC columns Reprosil Chiral NR, Chiralpak AD). HPLC (method LCMS_gradient) $t_R$=1.13 min. $^1$H NMR (CDCl$_3$, 300 MHz): δ 1.15 (s, 3H), 1.67 (s, 3H), 1.71 (s, 3H), 2.19-2.37 (m, 1H), 2.56-2.67 (m, 1H), 2.86 (s, 3H), 3.60-3.70 (m, 1H), 3.79 (ddd, J=4.8, 10.2, 10.2 Hz, 1H), 4.43-4.52 (m, 1H), 7.13 (dd, J=8.9, 11.9 Hz, 1H), 7.70 (dd, J=2.6, 7.1 Hz, 1H), 7.84 (ddd, J=2.6, 4.0, 8.9 Hz, 1H), 7.93-7.97 (m, 1H), 8.72 (dd, J=0.6, 2.0 Hz, 1H), 9.98 (s, 1H). MS (ES+) m/z 469.3 [M+H].

N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide (2AB)

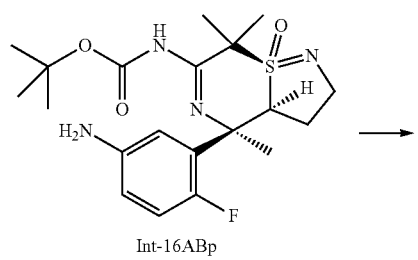

Int-16ABp

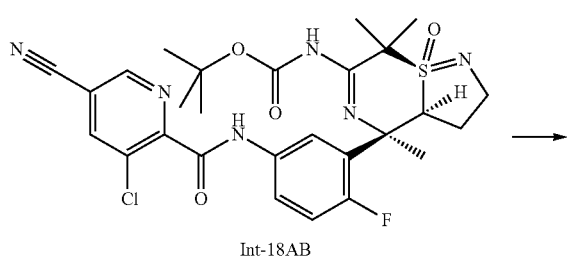

Int-18AB

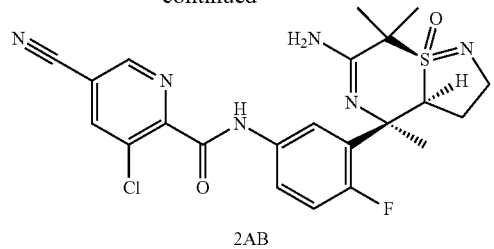

2AB

Step 1: tert-Butyl ((3aS,4R,8R)-4-(5-(3-chloro-5-cyanopicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-18AB)

5-Cyano-3-chloropicolinic acid (43.9 mg, 240 µmol) was suspended in dichloromethane (5 mL), the suspension was cooled to 0-5° C. (ice bath) and oxalyl chloride (42.7 mg, 29.4 µL, 336 µmol) as well as dimethylformamide (0.308 M in toluene, 39 µL, 12 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-cyano-3-chloropicolinoyl chloride as brown oil (48 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 60 mg, 141 µmol) was dissolved in dichloromethane (5 mL), the solution cooled to 10° C. and N,N-diisopropylethylamine (31.1 mg, 42 µL, 242 µmol) was added, followed by a solution of 5-cyano-3-chloropicolinoyl chloride (vide supra, 38.4 mg, 192 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 30:70 to 100:0) to yield, after drying in vacuo (40° C., 5 mbar), the title compound as a brown solid (77 mg, 93%). HPLC (method LCMS_fglm) $t_R$=1.22 min. MS (ES+) m/z 589.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide (2AB)

tert-Butyl ((3aS,4R,8R)-4-(5-(3-chloro-5-cyanopicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-18AB, 77 mg, 130 µmol) was dissolved in dichloromethane (5 mL) and trifluoroacetic acid (403 mg, 272 µL, 3.53 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 24 g, eluting with 2 M ammonia in methanol/dichloromethane, gradient 2:98 to 8:92) to yield, after drying in vacuo (40° C., 5 mbar), the title compound as a light yellow solid (50 mg, 78% yield). HPLC (method LCMS_gradient) $t_R$=1.14 min. $^1$H NMR (CDCl$_3$, 300 MHz): δ 1.46-1.64 (m, 1H), 1.77 (s, 3H), 1.88 (s, 3H), 1.92-2.03 (m, 1H), 1.92 (s, 3H), 3.41 (dd, J=7.3, 10.5 Hz, 1H), 3.63 (ddd, J=5.0, 10.7, 10.7 Hz, 1H), 4.24 (ddd, J=1.3, 7.1, 12.3 Hz, 1H), 4.67 (br s, 2H), 7.09 (dd, J=8.7, 11.7 Hz, 1H), 7.94 (ddd, J=3.0, 4.1, 8.8 Hz, 1H), 8.16-8.20 (m, 1H), 8.19 (d, J=1.8 Hz, 1H), 8.79 (d, J=1.8 Hz, 1H), 9.74 (s, 1H). MS (ES+) m/z 489.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide (3AB)

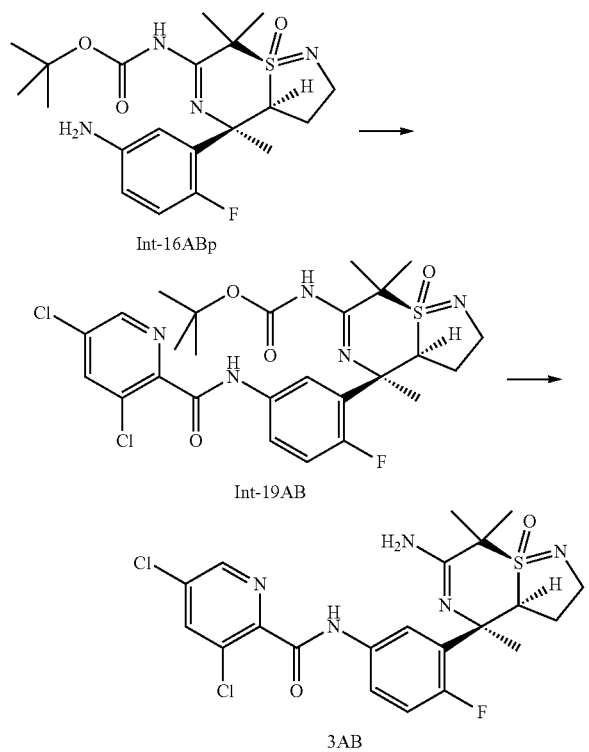

Step 1: tert-Butyl ((3aS,4R,8R)-4-(5-(3,5-dichloropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-19AB)

3,5-Dichloropicolinic acid (61.5 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 48 µL, 15 µmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 3,5-dichloropicolinoyl chloride as yellow oil (67 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (41.4 mg, 56 µL, 320 µmol) was added, followed by a solution of 3,5-dichloropicolinoyl chloride (vide supra, 54 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 30:70 to 100:0) to yield, after drying in vacuo (40° C., 5 mbar), the title compound as a light brown solid (103 mg, 92%). HPLC (method LCMS_fglm) $t_R$=1.34 min. MS (ES+) m/z 598.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide (3AB)

tert-Butyl ((3aS,4R,8R)-4-(5-(3,5-dichloropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-19AB, 103 mg, 172 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 24 g, eluting with 2 M ammonia in methanol/dichloromethane, gradient 2:98 to 6:94) to yield, after drying in vacuo (40° C., 5 mbar), the title compound as an off-white powder (36 mg, 41% yield). HPLC (method LCMS_gradient) $t_R$=1.27 min. $^1$H NMR (CDCl$_3$, 300 MHz): δ 1.47-1.67 (m, 1H), 1.77 (s, 3H), 1.88 (s, 3H), 1.91-2.03 (m, 1H), 1.92 (s, 3H), 3.41 (dd, J=7.2, 10.6 Hz, 1H), 3.64 (ddd, J=5.0, 10.7, 10.7 Hz, 1H), 4.24 (ddd, J=1.3, 7.1, 12.3 Hz, 1H), 4.65 (br s, 2H), 7.07 (dd, J=8.9, 11.7 Hz, 1H), 7.91-7.97 (m, 1H), 7.92 (d, J=2.0 Hz, 1H), 8.16 (dd, J=2.8, 7.1 Hz, 1H), 8.49 (d, J=2.0 Hz, 1H), 9.76 (s, 1H). MS (ES+) m/z 498.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide (4AB)

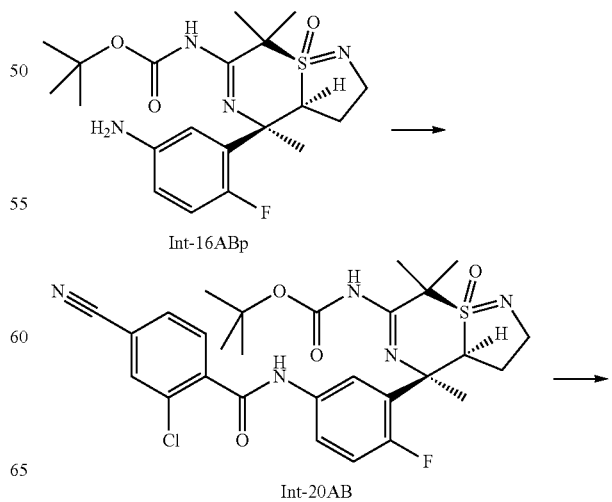

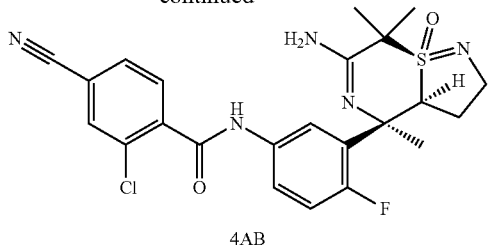

4AB

Step 1: tert-Butyl ((3aS,4R,8R)-4-(5-(2-chloro-4-cyanobenzamido)-2-fluorophenyl)-4,7,7-trimethyl-8-oxido-3,3a,4,7-tetrahydro-2H-isothiazolo[1,5-a][1,4]thiazin-6-yl)carbamate (Int-20AB)

2-Chloro-4-cyanobenzoic acid (58.2 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 48 μL, 15 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 2-chloro-4-cyanobenzoyl chloride as yellow oil (64 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (41.4 mg, 56 μL, 320 μmol) was added, followed by a solution of 2-chloro-4-cyanobenzoyl chloride (vide supra, 51 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a light yellow solid (96 mg, 87%). HPLC (method LCMS_fglm) $t_R$=1.22 min. MS (ES+) m/z 588.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide (4AB)

tert-Butyl ((3aS,4R,8R)-4-(5-(2-chloro-4-cyanobenzamido)-2-fluorophenyl)-4,7,7-trimethyl-8-oxido-3,3a,4,7-tetrahydro-2H-isothiazolo[1,5-a][1,4]thiazin-6-yl)carbamate (Int-20AB, 96 mg, 163 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 24 g, eluting with 2 M ammonia in methanol/dichloromethane, gradient 2:98 to 8:92) to yield, after drying in vacuo (40° C., 5 mbar), the title compound as an off-white powder (48 mg, 60% yield). HPLC (method LCMS_gradient) $t_R$=1.12 min. $^1$H NMR (CDCl$_3$, 300 MHz): δ 1.43-1.60 (m, 1H), 1.73 (s, 3H), 1.85 (s, 3H), 1.89 (s, 3H), 1.92-2.02 (m, 1H), 3.39 (dd, J=7.6, 10.4 Hz, 1H), 3.60 (ddd, J=5.0, 10.7, 10.7 Hz, 1H), 4.17-4.26 (m, 1H), 4.69 (br s, 2H), 7.09 (dd, J=8.8, 11.5 Hz, 1H), 7.68 (dd, J=1.4, 8.1 Hz, 1H), 7.76-7.86 (m, 3H), 8.14 (s, 1H), 8.17 (dd, J=2.8, 7.1 Hz, 1H). MS (ES+) m/z 488.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)picolinamide (5AB)

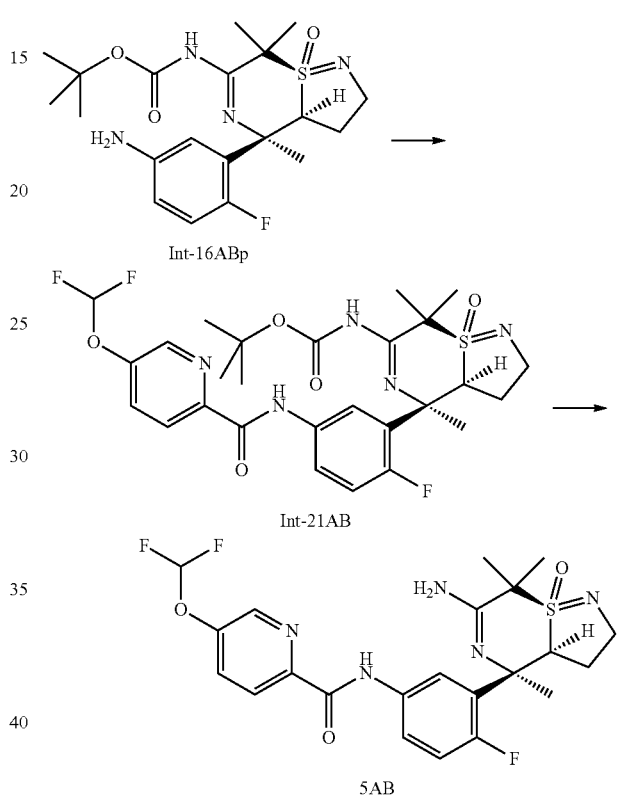

Step 1: tert-Butyl ((3aS,4R,8R)-4-(5-(5-(difluoromethoxy)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-21AB)

5-(Difluoromethoxy)picolinic acid (60.6 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 3 h at room temperature. Then, it was concentrated in vacuo (40° C., 5 mbar) and dried azeotropically by two cycles of addition of toluene (3 mL) followed by concentration in vacuo to afford 5-(difluoromethoxy)picolinoyl chloride as green oil (66 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-(difluoromethoxy)picolinoyl chloride (vide supra, 52.8 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a light yellow solid (102 mg, 91%). HPLC (method LCMS_fglm) $t_R$=1.32 min. MS (ES+) m/z 596.5 [M+H].

Step 2: N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)picolinamide (5AB)

tert-Butyl ((3aS,4R,8R)-4-(5-(5-(difluoromethoxy)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-21AB, 102 mg, 171 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as an off-white powder (82 mg, 96% yield). HPLC (method LCMS_gradient) $t_R$=1.35 min. $^1$H NMR (CDCl$_3$, 300 MHz): δ 1.47-1.71 (m, 1 H), 1.77 (s, 3H), 1.88 (s, 3H), 1.90-2.04 (m, 1H), 1.93 (s, 3H), 3.42 (dd, J=7.7, 10.5 Hz, 1H), 3.64 (ddd, J=4.9, 10.6, 10.6 Hz, 1H), 4.19-4.29 (m, 1H), 4.66 (br s, 2H), 6.66 (t, J=71.9 Hz, 1H), 7.08 (dd, J=8.7, 11.7 Hz, 1H), 7.68 (dd, J=2.5, 8.6 Hz, 1H), 7.91-7.98 (m, 1H), 8.22 (dd, J=2.8, 7.1 Hz, 1H), 8.34 (d, J=8.7 Hz, 1H), 8.48 (d, J=2.2 Hz, 1H), 9.86 (s, 1H). MS (ES+) m/z 496.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide (6AB)

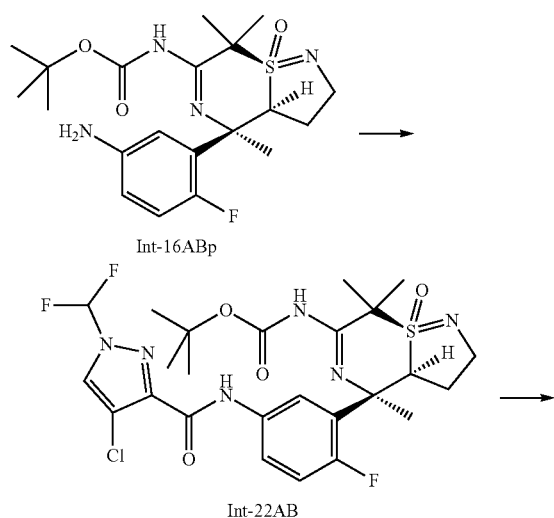

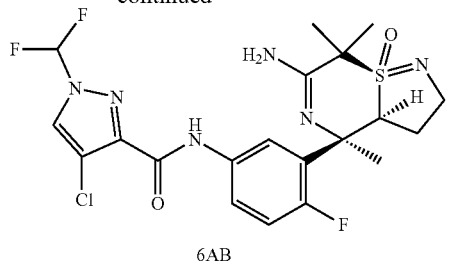

Step 1: tert-Butyl ((3aS,4R,8R)-4-(5-(4-chloro-1-(difluoromethyl)-1H-pyrazole-3-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-22AB)

4-Chloro-1-(diflouromethyl)-1H-pyrazole-3-carboxylic acid (63 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 4-chloro-1-(diflouromethyl)-1H-pyrazole-3-carbonyl chloride as yellow oil (69 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 4-chloro-1-(diflouromethyl)-1H-pyrazole-3-carbonyl chloride (vide supra, 55 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a white solid (77 mg, 68%). HPLC (method LCMS_fglm) $t_R$=1.26 min. MS (ES+) m/z 603.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide (6AB)

tert-Butyl ((3aS,4R,8R)-4-(5-(4-chloro-1-(difluoromethyl)-1H-pyrazole-3-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-22AB, 77 mg, 128 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 8:92) to yield, after drying in vacuo (40° C., 5 mbar), the title compound as a white powder (64 mg, quant.). HPLC (method LCMS_gradient) $t_R$=1.14 min. $^1$H NMR (CDCl$_3$, 300 MHz): δ 1.47-1.65 (m, 1H), 1.76 (s, 3H), 1.88 (s, 3H), 1.90-2.02 (m, 1H), 1.91 (s, 3H), 3.41 (dd, J=7.7, 10.3 Hz, 1H), 3.63 (ddd, J=4.9, 10.6, 10.6 Hz, 1H), 4.18-4.28 (m, 1H), 4.65 (br s, 2H), 7.06 (dd, J=8.9, 11.7 Hz, 1H), 7.16 (t, J=59.9 Hz, 1H), 7.80-7.87 (m, 1H), 7.94 (s, 1H), 8.15 (dd, J=2.7, 7.0 Hz, 1H), 8.58 (s, 1H). MS (ES+) m/z 503.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)pyrazine-2-carboxamide (7AB)

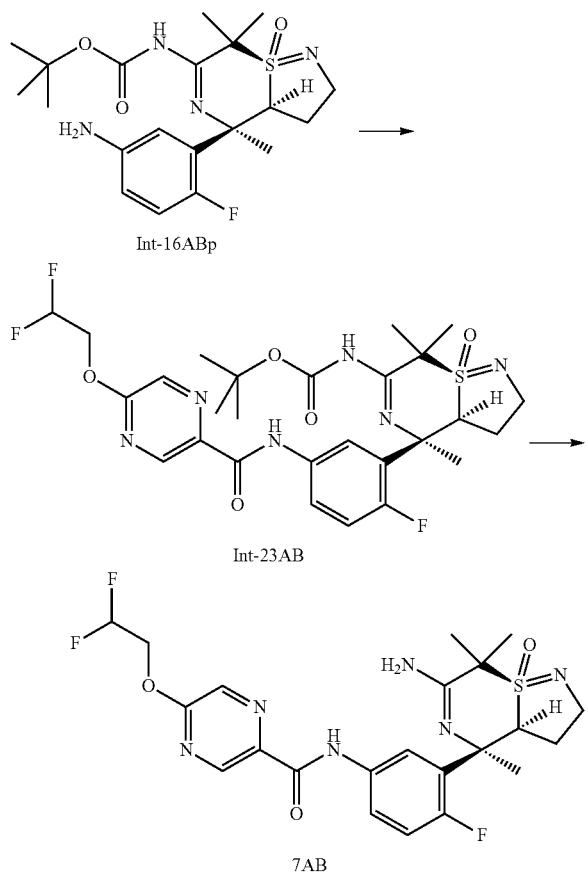

Step 1: tert-Butyl ((3aS,4R,8R)-4-(5-(5-(2,2-difluoroethoxy)pyrazine-2-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-23AB)

5-(2,2-Difluoroethoxy)pyrazine-2-carboxylic acid (65.4 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-(2,2-difluoroethoxy)pyrazine-2-carbonyl chloride as yellow oil (71 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (41.4 mg, 56 μL, 320 μmol) was added, followed by a solution of 5-(2,2-difluoroethoxy)pyrazine-2-carbonyl chloride (vide supra, 56.8 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a colorless viscous oil (118 mg, 86% purity by HPLC, 88% yield). HPLC (method LCMS_fglm) $t_R$=1.31 min. MS (ES+) m/z 611.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)pyrazine-2-carboxamide (7AB)

tert-Butyl ((3aS,4R,8R)-4-(5-(5-(2,2-difluoroethoxy)pyrazine-2-carboxamido)-2-fluorophenyl)-4,7,7-trimethyl-8-oxido-3,3a,4,7-tetrahydro-2H-isothiazolo[1,5-a][1,4]thiazin-6-yl)-carbamate (Int-23AB, 118 mg, 86% purity, 166 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 24 g, eluting with 2 M ammonia in methanol/dichloromethane, gradient 2:98 to 8:92) to yield, after drying in vacuo (40° C., 5 mbar), the title compound as an off-white powder (61 mg, 72% yield). HPLC (method LCMS_gradient) $t_R$=1.35 min. $^1$H NMR (CDCl$_3$, 300 MHz): δ 1.47-1.65 (m, 1H), 1.77 (s, 3H), 1.88 (s, 3H), 1.92 (s, 3H), 1.93-2.03 (m, 1H), 3.42 (dd, J=7.3, 10.3 Hz, 1H), 3.64 (ddd, J=5.0, 10.6, 10.6 Hz, 1H), 4.19-4.29 (m, 1H), 4.66 (br s, 2H), 4.67 (dt, J=4.0, 13.5 Hz, 2H), 6.17 (tt, J=4.0, 54.9 Hz, 1H), 7.08 (dd, J=8.9, 11.7 Hz, 1H), 7.89-7.96 (m, 1H), 8.21 (dd, J=2.8, 7.1 Hz, 1H), 8.28 (d, J=1.4 Hz, 1H), 9.03 (d, J=1.2 Hz, 1H), 9.51 (s, 1H). MS (ES+) m/z 511.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl)picolinamide (8AB)

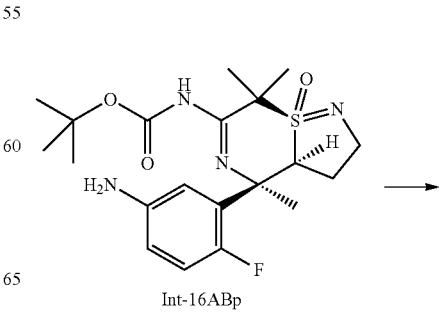

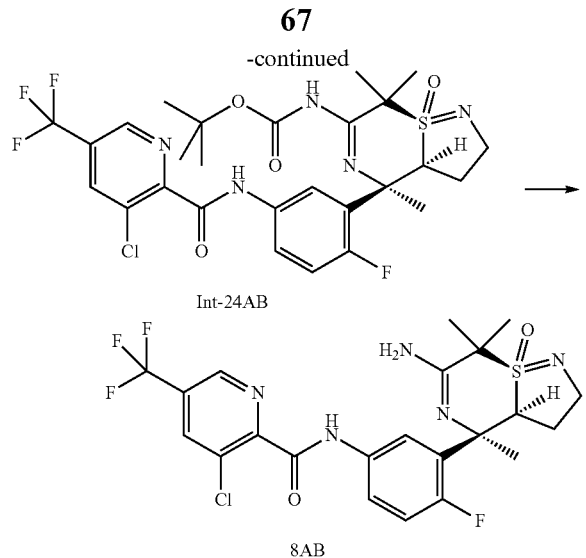

Int-24AB

8AB

Step 1: tert-Butyl ((3aS,4R,8R)-4-(5-(3-chloro-5-(trifluoromethyl)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-24AB)

3-Chloro-5-(trifluoromethyl)picolinic acid (72.3 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 3-chloro-5-(trifluoromethyl)picolinoyl chloride as yellow oil (78 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 3-chloro-5-(trifluoromethyl)picolinoyl chloride (vide supra, 62 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 25:75 to 100:0) to yield, after drying in vacuo (40° C., 5 mbar), the title compound as an off-white solid (100 mg, 84% yield). HPLC (method LCMS_fglm) $t_R$=1.35 min. MS (ES+) m/z 632.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl)picolinamide (8AB)

tert-Butyl ((3aS,4R,8R)-4-(5-(3-chloro-5-(trifluoromethyl)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-24AB, 100 mg, 158 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 24 g, eluting with 2 M ammonia in methanol/dichloromethane, gradient 2:98 to 6:94) to yield, after drying in vacuo (40° C., 5 mbar), the title compound as an off-white powder (69 mg, 81% yield). HPLC (method LCMS_gradient) $t_R$=1.40 min. $^1$H NMR (CDCl$_3$, 300 MHz): δ 1.45-1.67 (m, 1H), 1.77 (s, 3H), 1.88 (s, 3H), 1.91-2.03 (m, 1H), 1.92 (s, 3H), 3.41 (dd, J=7.4, 10.4 Hz, 1H), 3.63 (ddd, J=5.0, 10.6, 10.6 Hz, 1H), 4.24 (ddd, J=1.2, 7.2, 12.3 Hz, 1H), 4.64 (br s, 2H), 7.08 (dd, J=8.7, 11.7 Hz, 1H), 7.98 (ddd, J=2.9, 4.1, 8.7 Hz, 1H), 8.13 (dd, J=2.8, 7.1 Hz, 1H), 8.24 (d, J=2.2 Hz, 1H), 8.75 (d, J=2.2 Hz, 1H), 9.70 (s, 1H). MS (ES+) m/z 532.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-4-cyano-2-methylbenzamide (9AB)

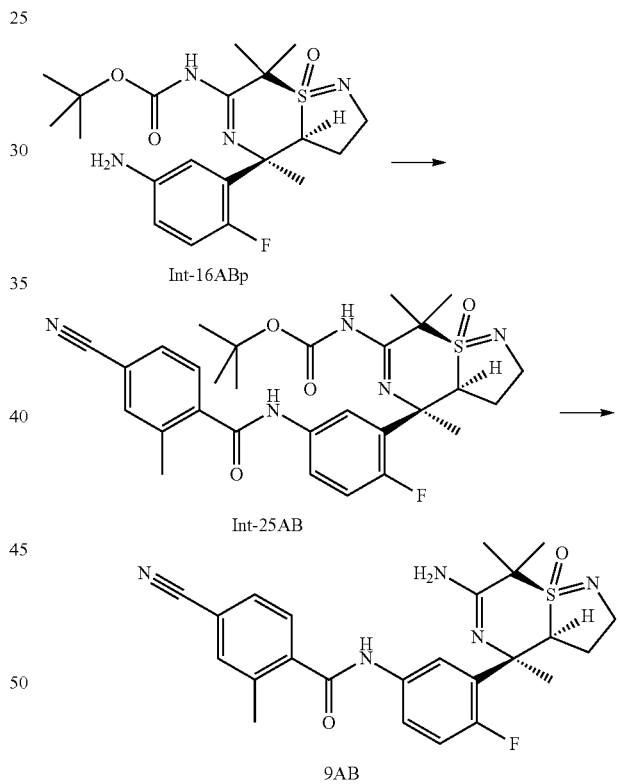

Int-16ABp

Int-25AB

9AB

Step 1: tert-Butyl ((3aS,4R,8R)-4-(5-(4-cyano-2-methylbenzamido)-2-fluorophenyl)-4,7,7-trimethyl-8-oxido-3,3a,4,7-tetrahydro-2H-isothiazolo[1,5-a][1,4]thiazin-6-yl)carbamate (Int-25AB)

4-Cyano-2-methylbenzoic acid (51.6 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 3 h at room temperature. Then, it was concentrated in vacuo (40° C., 5 mbar) and dried azeotropically by two cycles of addition of toluene (3 mL) followed by concentration in vacuo to afford 4-cyano-2-methylbenzoyl chloride as colorless oil (57 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 4-cyano-2-methylbenzoyl chloride (vide supra, 46 mg, 256 μmol) in dichloromethane (4 mL). The reaction mixture was stirred for 25 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 40:60 to 100:0) to yield, after drying in vacuo (40° C., 5 mbar), the title compound as a colorless oil (107 mg, 71% purity (HPLC), 71% yield). HPLC (method LCMS_fglm) $t_R$=1.22 min. MS (ES+) m/z 568.4 [M+H].

Step 2: N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-cyano-2-methyl-benzamide (9AB)

tert-Butyl ((3aS,4R,8R)-4-(5-(4-cyano-2-methylbenzamido)-2-fluorophenyl)-4,7,7-trimethyl-8-oxido-3,3a,4,7-tetrahydro-2H-isothiazolo[1,5-a][1,4]thiazin-6-yl)carbamate (Int-25AB, 107 mg, 71% purity, 134 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 24 g, eluting with 2 M ammonia in methanol/dichloromethane, gradient 2:98 to 6:94) to yield, after drying in vacuo (40° C., 5 mbar), the title compound as a white powder (48 mg, 77% yield). HPLC (method LCMS_gradient) $t_R$=1.18 min. $^1$H NMR (CDCl$_3$, 300 MHz): δ 1.42-1.60 (m, 1H), 1.73 (s, 3H), 1.85 (s, 3H), 1.89 (s, 3H), 1.90-2.04 (m, 1H), 2.54 (s, 3H), 3.39 (dd, J=7.5, 10.5 Hz, 1H), 3.61 (ddd, J=4.8, 10.6, 10.6 Hz, 1H), 4.22 (dd, J=7.4, 12.2 Hz, 1H), 4.64 (br s, 2H), 7.08 (dd, J=8.9, 11.5 Hz, 1H), 7.58 (s, 3H), 7.77 (s, 1H), 7.80-7.88 (m, 1H), 8.08-8.15 (m, 1H). MS (ES+) m/z 468.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide (10AB)

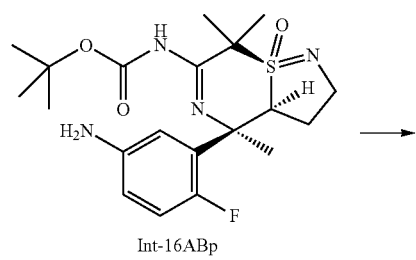

Int-16ABp

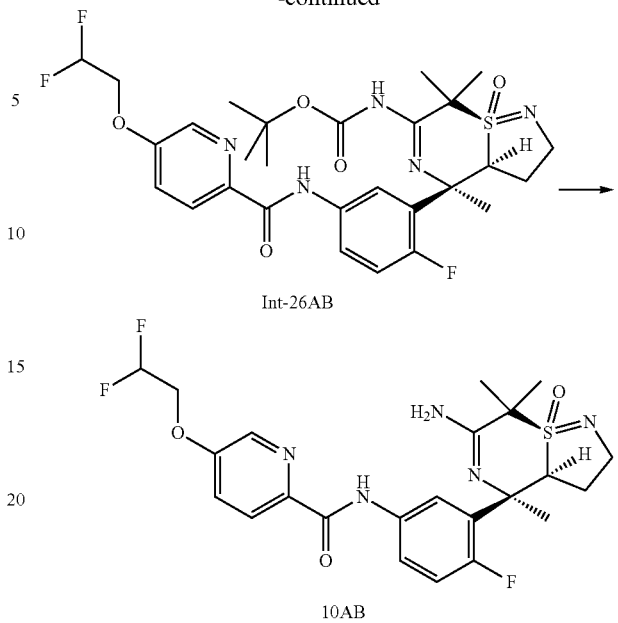

Int-26AB

10AB

Step 1: tert-Butyl ((3aS,4R,8R)-4-(5-(5-(2,2-difluoroethoxy)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-26AB)

5-(2,2-Difluoroethoxy)picolinic acid (65.1 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 5-(2,2-difluoroethoxy)picolinoyl chloride as yellow oil (70 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-(2,2-difluoroethoxy)picolinoyl chloride (vide supra, 56.5 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 40:60 to 100:0) to yield, after drying in vacuo (40° C., 5 mbar), the title compound as a colorless viscous oil (113 mg, 86% purity by HPLC, 84% yield). HPLC (method LCMS_fglm) $t_R$=1.29 min. MS (ES+) m/z 610.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide (10AB)

tert-Butyl ((3aS,4R,8R)-4-(5-(5-(2,2-difluoroethoxy)picolinamido)-2-fluorophenyl)-4,7,7-trimethyl-8-oxido-3,3a, 4,7-tetrahydro-2H-isothiazolo[1,5-a][1,4]thiazin-6-yl)carbamate (Int-26AB, 113 mg, 86% purity, 159 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a white powder (71 mg, 88% yield). HPLC (method LCMS_gradient) $t_R$=1.34 min. $^1$H NMR (CDCl$_3$, 300 MHz): δ 1.51-1.66 (m, 1H), 1.77 (s, 3H), 1.88 (s, 3H), 1.92-2.03 (m, 1H), 1.93 (s, 3H), 3.41 (dd, J=7.7, 10.1 Hz, 1H), 3.64 (ddd, J=4.8, 10.5, 10.5 Hz, 1H), 4.24 (dd, J=7.9, 12.1 Hz, 1H), 4.33 (dt, J=4.0, 12.8 Hz, 2H), 4.68 (br s, 2H), 6.16 (tt, J=3.8, 54.7 Hz, 1H), 7.07 (dd, J=8.9, 11.7 Hz, 1H), 7.39 (dd, J=2.7, 8.8 Hz, 1H), 7.90-7.99 (m, 1H), 8.21 (dd, J=2.8, 7.1 Hz, 1H), 8.28 (d, J=8.7 Hz, 1H), 8.33 (d, J=2.8 Hz, 1H), 9.83 (s, 1H). MS (ES+) m/z 510.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)-3-methylpicolinamide (11AB)

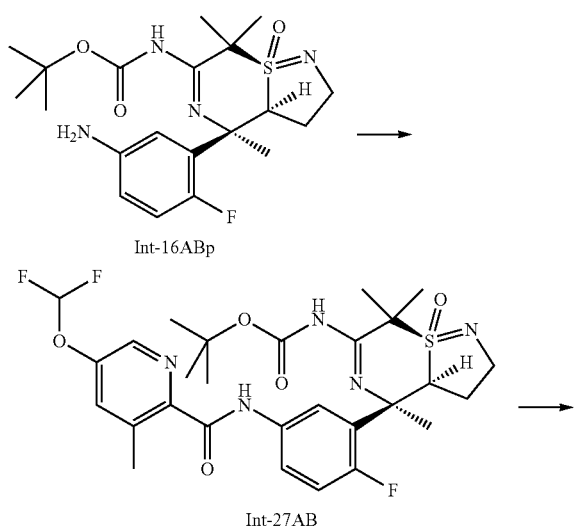

Step 1: tert-Butyl ((3aS,4R,8R)-4-(5-(5-(difluoromethoxy)-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-27AB)

5-(Difluoromethoxy)-3-methylpicolinic acid (65.1 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 1.5 h at room temperature. Then, it was concentrated in vacuo (40° C., 5 mbar) and dried azeotropically by two cycles of addition of toluene (3 mL) followed by concentration in vacuo to afford 5-(difluoromethoxy)-3-methylpicolinoyl chloride as brown oil (70 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-(difluoromethoxy)-3-methylpicolinoyl chloride (vide supra, 56.5 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a colorless viscous oil (98 mg, 88% purity by HPLC, 75% yield). HPLC (method LCMS_fglm) $t_R$=1.38 min. MS (ES+) m/z 610.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)-3-methylpicolinamide (11AB)

tert-Butyl ((3aS,4R,8R)-4-(5-(5-(difluoromethoxy)-3-methylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-27AB, 98 mg, 88% purity, 142 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a white powder (69 mg, 95% yield). HPLC (method LCMS_gradient) $t_R$=1.45 min. $^1$H NMR (CDCl$_3$, 300 MHz): δ 1.48-1.68 (m, 1H), 1.77 (s, 3H), 1.88 (s, 3H), 1.92 (s, 3H), 1.93-2.03 (m, 1H), 2.85 (s, 3H), 3.41 (dd, J=7.3, 10.3 Hz, 1H), 3.64 (ddd, J=5.0, 10.6, 10.6 Hz, 1H), 4.25 (ddd, J=1.2, 7.1, 12.3 Hz, 1H), 4.64 (br s, 2H), 6.64 (t, J=72.1 Hz, 1H), 7.06 (dd, J=8.9, 11.7 Hz, 1H), 7.41-7.44 (m, 1H), 7.95 (ddd, J=3.0, 4.2, 8.9 Hz, 1H), 8.13 (dd, J=2.8, 7.1 Hz, 1H), 8.32 (d, J=2.0 Hz, 1H), 10.05 (s, 1H). MS (ES+) m/z 510.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)-picolinamide (12AB)

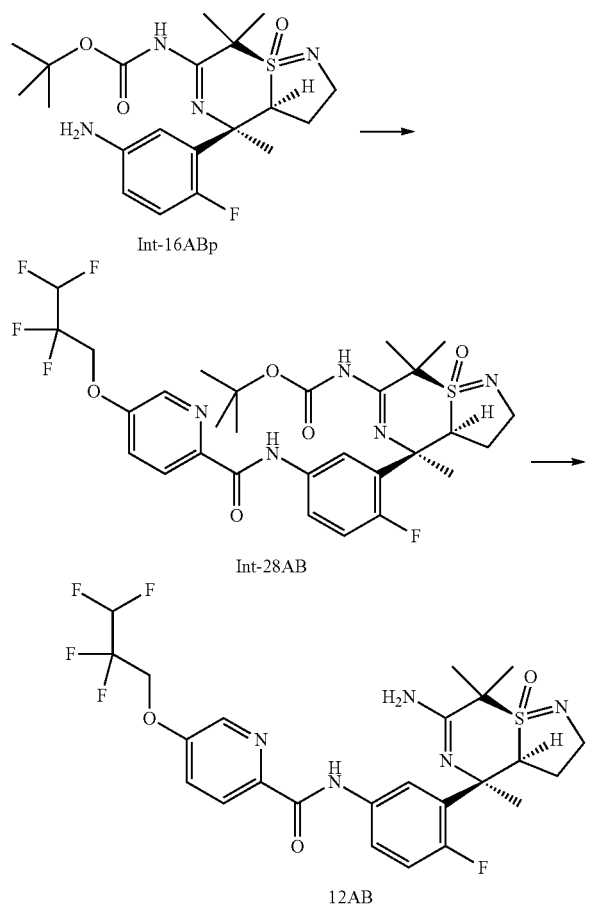

Step 1: tert-Butyl ((3aS,4R,8R)-4-(2-fluoro-5-(5-(2,2,3,3-tetrafluoropropoxy)picolinamido)-phenyl)-4,7,7-trimethyl-8-oxido-3,3a,4,7-tetrahydro-2H-isothiazolo[1,5-a][1,4]thiazin-6-yl)carbamate (Int-28AB)

5-(2,2,3,3-Tetrafluoropropoxy)picolinic acid (81.1 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-(2,2,3,3-tetrafluoropropoxy)picolinoyl chloride as brown oil (86 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-(2,2,3,3-tetrafluoropropoxy)picolinoyl chloride (vide supra, 69 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 40:60 to 100:0) to yield, after drying in vacuo (40° C., 5 mbar), the title compound as a off-white solid (120 mg, 90% purity by HPLC, 87% yield). HPLC (method LCMS_fglm) $t_R$=1.36 min. MS (ES+) m/z 660.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)picolinamide (12AB)

tert-Butyl ((3aS,4R,8R)-4-(2-fluoro-5-(5-(2,2,3,3-tetrafluoropropoxy)picolinamido)-phenyl)-4,7,7-trimethyl-8-oxido-3,3a,4,7-tetrahydro-2H-isothiazolo[1,5-a][1,4]thiazin-6-yl)carbamate (Int-28AB, 120 mg, 90% purity, 164 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a white powder (82 mg, 89% yield). HPLC (method LCMS_gradient) $t_R$=1.58 min. $^1$H NMR (CDCl$_3$, 300 MHz): δ 1.49-1.66 (m, 1H), 1.77 (s, 3H), 1.88 (s, 3H), 1.92-2.03 (m, 1H), 1.93 (s, 3H), 3.41 (dd, J=7.7, 10.3 Hz, 1H), 3.64 (ddd, J=4.8, 10.5, 10.5 Hz, 1H), 4.24 (dd, J=7.2, 12.2 Hz, 1H), 4.51 (t, J=11.8 Hz, 2H), 4.65 (br s, 2H), 6.07 (tt, J=4.0, 53.0 Hz, 1H), 7.07 (dd, J=8.9, 11.5 Hz, 1H), 7.42 (dd, J=2.7, 8.8 Hz, 1H), 7.90-7.98 (m, 1H), 8.22 (dd, J=2.7, 7.0 Hz, 1H), 8.30 (d, J=8.5 Hz, 1H), 8.34 (d, J=2.6 Hz, 1H), 9.83 (s, 1H). MS (ES+) m/z 550.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3-chloro-5-(difluoromethoxy)picolinamide (13AB)

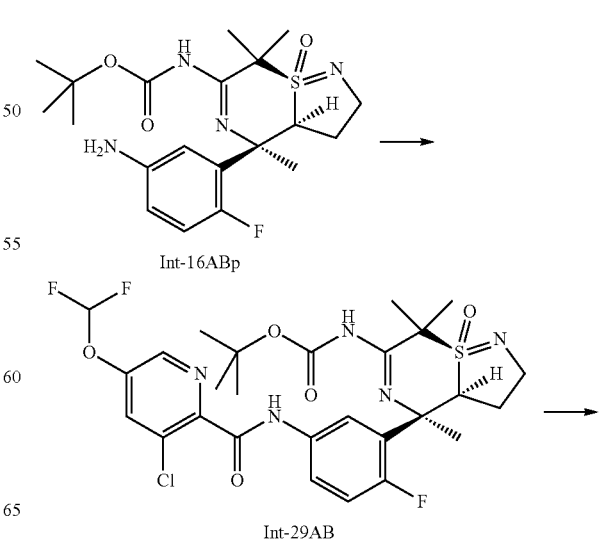

-continued

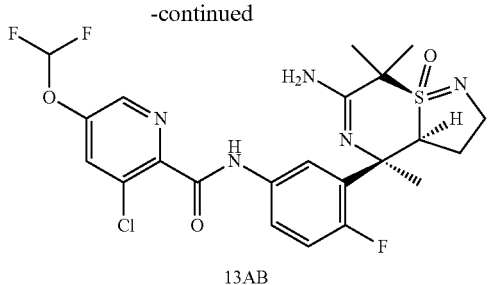

13AB

Step 1: tert-Butyl ((3aS,4R,8R)-4-(5-(3-chloro-5-(difluoromethoxy)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-29AB)

3-Chloro-5-(difluoromethoxy)-picolinic acid (71.6 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 3-chloro-5-(difluoromethoxy)-picolinoyl chloride as yellow oil (77 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 3-chloro-5-(difluoromethoxy)-picolinoyl chloride (vide supra, 62 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 35:65 to 100:0) to yield, after drying in vacuo (40° C., 5 mbar), the title compound as a light yellow foam (110 mg, 73% purity by HPLC, 68% yield). HPLC (method LCMS_fglm) $t_R$=1.31 min. MS (ES+) m/z 630.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3-chloro-5-(difluoromethoxy)picolinamide (13AB)

tert-Butyl ((3aS,4R,8R)-4-(5-(3-chloro-5-(difluoromethoxy)picolinamido)-2-fluorophenyl)-4,7,7-trimethyl-8-oxido-3,3a,4,7-tetrahydro-2H-isothiazolo[1,5-a][1,4]thiazin-6-yl)carbamate (Int-29AB, 110 mg, 73% purity, 128 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a white powder (56 mg, 83% yield). HPLC (method LCMS_gradient) $t_R$=1.29 min. $^1$H NMR (CDCl$_3$, 300 MHz): δ 1.47-1.67 (m, 1H), 1.77 (s, 3H), 1.88 (s, 3H), 1.92 (s, 3H), 1.92-2.03 (m, 1H), 3.41 (dd, J=7.9, 10.3 Hz, 1H), 3.64 (ddd, J=5.0, 10.6, 10.6 Hz, 1H), 4.20-4.29 (m, 1H), 4.64 (br s, 2H), 6.67 (t, J=71.3 Hz, 1H), 7.07 (dd, J=8.9, 11.7 Hz, 1H), 7.70 (d, J=2.2 Hz, 1H), 7.91-7.98 (m, 1H), 8.15 (dd, J=2.8, 7.1 Hz, 1H), 8.42 (d, J=2.2 Hz, 1H), 9.77 (s, 1H). MS (ES+) m/z 530.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methoxypyrazine-2-carboxamide (14AB)

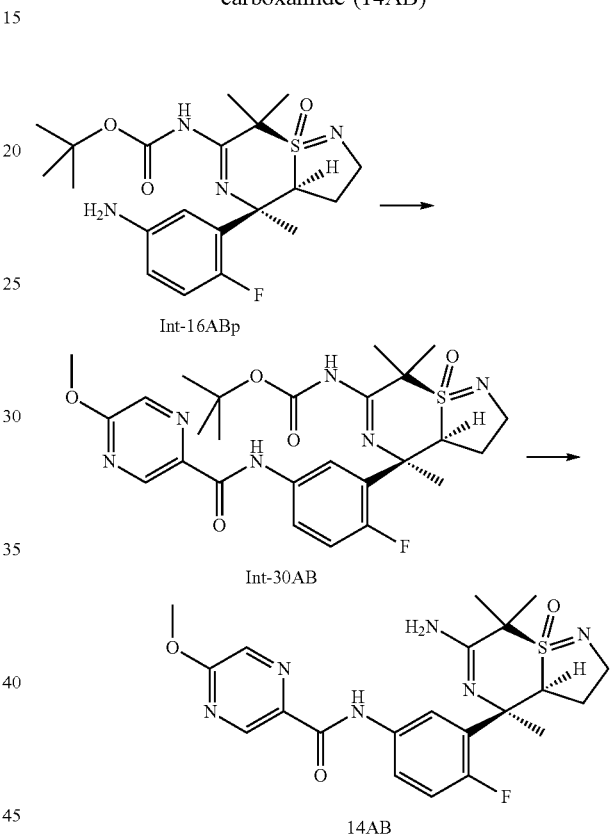

Int-16ABp

Int-30AB

14AB

Step 1: tert-Butyl ((3aS,4R,8R)-4-(2-fluoro-5-(5-methoxypyrazine-2-carboxamido)phenyl)-4,7,7-trimethyl-8-oxido-3,3a,4,7-tetrahydro-2H-isothiazolo[1,5-a][1,4]thiazin-6-yl)carbamate (Int-30AB)

5-Methoxypyrazine-2-carboxylic acid (49.4 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-methoxypyrazine-2-carbonyl chloride as brown oil (55 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (41.4 mg, 56 µL, 320 µmol) was added, followed by a solution of 5-methoxypyrazine-2-carbonyl chloride (vide supra, 44 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 40:60 to 100:0) to yield, after drying in vacuo (40° C., 5 mbar), the title compound as an off-white solid (102 mg, 95% purity by HPLC, 92% yield). HPLC (method LCMS_fglm) $t_R$=1.26 min. MS (ES+) m/z 561.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methoxypyrazine-2-carboxamide (14AB)

tert-Butyl ((3aS,4R,8R)-4-(2-fluoro-5-(5-methoxypyrazine-2-carboxamido)phenyl)-4,7,7-trimethyl-8-oxido-3,3a,4,7-tetrahydro-2H-isothiazolo[1,5-a][1,4]thiazin-6-yl)carbamate (Int-30AB, 102 mg, 95% purity, 173 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as a white powder (62 mg, 78% yield). HPLC (method LCMS_gradient) $t_R$=1.17 min. $^1$H NMR (CDCl$_3$, 300 MHz): δ 1.47-1.67 (m, 1H), 1.77 (s, 3H), 1.88 (s, 3H), 1.92 (s, 3H), 1.93-2.03 (m, 1H), 3.41 (dd, J=7.7, 10.3 Hz, 1H), 3.64 (ddd, J=5.0, 10.5, 10.5 Hz, 1H), 4.08 (s, 3H), 4.18-4.29 (m, 1H), 4.66 (br s, 2H), 7.07 (dd, J=8.8, 11.6 Hz, 1H), 7.87-7.96 (m, 1H), 8.17 (s, 1H), 8.21 (dd, J=2.5, 7.0 Hz, 1H), 9.03 (s, 1H), 9.53 (s, 1H). MS (ES+) m/z 461.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)pyrazine-2-carboxamide (15AB)

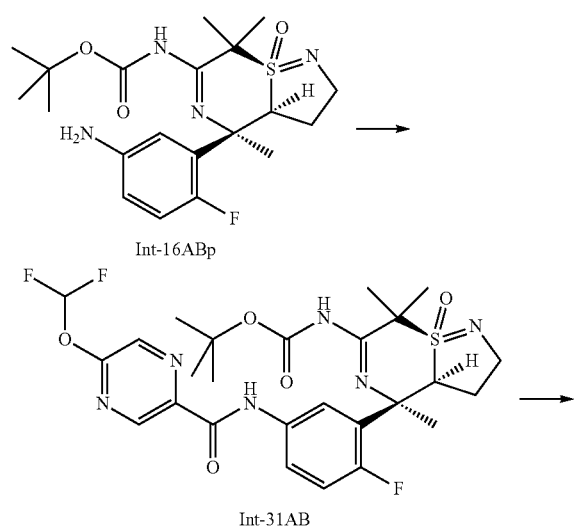

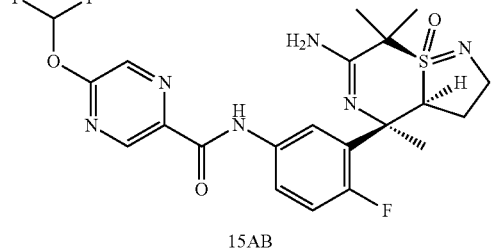

Step 1: tert-Butyl ((3aS,4R,8R)-4-(5-(5-(difluoromethoxy)pyrazine-2-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-31AB)

5-(Difluoromethoxy)pyrazine-2-carboxylic acid (60.8 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-(difluoromethoxy)pyrazine-2-carbonyl chloride as yellow oil (66 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-(difluoromethoxy)pyrazine-2-carbonyl chloride (vide supra, 53 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 24 g, eluting with 2 M ammonia in methanol/dichloromethane, gradient 1:99 to 6:94) to yield, after drying in vacuo (40° C., 5 mbar), the title compound as a light yellow foam (57 mg, 83% purity by HPLC, 42% yield). HPLC (method LCMS_fglm) $t_R$=1.31 min. MS (ES+) m/z 597.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)pyrazine-2-carboxamide (15AB)

tert-Butyl ((3aS,4R,8R)-4-(5-(5-(difluoromethoxy)pyrazine-2-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-31AB, 57 mg, 83% purity, 79 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94), followed by preparative HPLC (Gemini 5 um C18 110A 70×30 mm, eluting with gradient acetonitrile/0.05% triethylamine in water 20/80 to 95/5) to yield, after lyophilization, the title compound as a white lyophilized powder (27 mg, 69% yield). HPLC (method LCMS_gradient) t$_R$=1.27 min. $^1$H NMR (CDCl$_3$, 300 MHz): δ 1.50-1.61 (m, 1H), 1.77 (s, 3H), 1.88 (s, 3H), 1.92 (s, 3H), 1.93-2.01 (m, 1H), 3.41 (dd, J=7.2, 10.6 Hz, 1H), 3.64 (ddd, J=5.0, 10.7, 10.7 Hz, 1H), 4.24 (ddd, J=1.3, 7.1, 12.3 Hz, 1H), 4.64 (br s, 2H), 7.09 (dd, J=8.7, 11.7 Hz, 1H), 7.52 (t, J=71.3 Hz, 1H), 7.89 (ddd, J=2.9, 4.0, 8.8 Hz, 1H), 8.24 (dd, J=2.9, 7.0 Hz, 1H), 8.35 (d, J=1.4 Hz, 1H), 9.09 (d, J=1.2 Hz, 1H), 9.51 (s, 1H). MS (ES+) m/z 497.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-cyanopicolinamide (16AB)

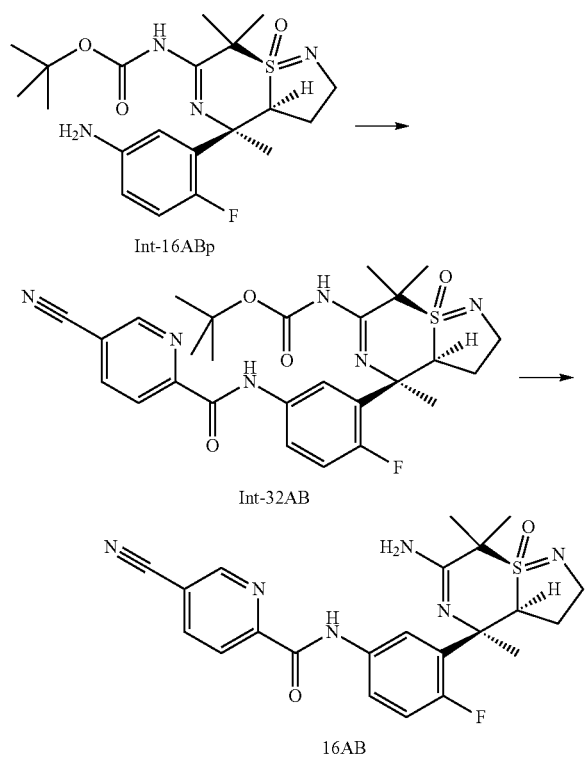

Step 1: tert-Butyl ((3aS,4R,8R)-4-(5-(5-cyanopicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-32AB)

5-Cyanopicolinic acid (47.5 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 5-cyanopicolinoyl chloride as light yellow oil (53 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-cyanopicolinoyl chloride (vide supra, 42 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 40 g, eluting with ethyl acetate/n-heptane, gradient 40:60 to 100:0) to yield, after drying in vacuo (40° C., 5 mbar), the title compound as a light purple solid (68 mg, 86% purity by HPLC, 56% yield). HPLC (method LCMS_fglm) t$_R$=1.23 min. MS (ES+) m/z 555.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-cyanopicolinamide (16AB)

tert-Butyl ((3aS,4R,8R)-4-(5-(5-cyanopicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-32AB, 110 mg, 86% purity, 105 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as an off-white powder (43 mg, 90% yield). HPLC (method LCMS_gradient) t$_R$=1.18 min. $^1$H NMR (CDCl$_3$, 300 MHz): δ 1.47-1.64 (m, 1H), 1.77 (s, 3H), 1.88 (s, 3H), 1.92 (s, 3H), 1.92-2.02 (m, 1H), 3.41 (dd, J=7.4, 10.6 Hz, 1H), 3.64 (ddd, J=5.0, 10.6, 10.6 Hz, 1H), 4.24 (ddd, J=1.3, 7.1, 12.3 Hz, 1H), 4.69 (br s, 2H), 7.10 (dd, J=8.8, 11.6 Hz, 1H), 7.94 (ddd, J=2.9, 4.1, 8.8 Hz, 1H), 8.22 (dd, J=2.0, 8.3 Hz, 1H), 8.25 (dd, J=2.8, 7.1 Hz, 1H), 8.44 (dd, J=0.9, 8.2 Hz, 1H), 8.90-8.92 (m, 1H), 9.88 (s, 1H). MS (ES+) m/z 455.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-fluoropicolinamide (17AB)

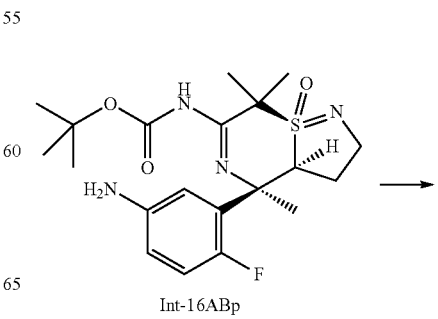

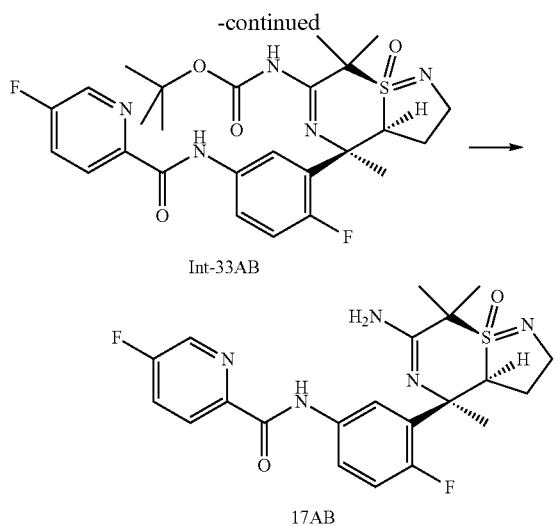

Step 1: tert-Butyl ((3aS,4R,8R)-4-(2-fluoro-5-(5-fluoropicolinamido)phenyl)-4,7,7-trimethyl-8-oxido-3,3a,4,7-tetrahydro-2H-isothiazolo[1,5-a][1,4]thiazin-6-yl)carbamate (Int-33AB)

5-Fluoropicolinic acid (45.2 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-fluoropicolinoyl chloride as yellow oil (51 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-fluoropicolinoyl chloride (vide supra, 40.8 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with 2 M ammonia in methanol/dichloromethane, gradient 1:99 to 3:97) to yield, after drying in vacuo (40° C., 5 mbar), the title compound as an off-white solid (90 mg, 87% yield). HPLC (method LCMS_fglm) $t_R$=1.28 min. MS (ES+) m/z 548.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-fluoropicolinamide (17AB)

tert-Butyl ((3aS,4R,8R)-4-(2-fluoro-5-(5-fluoropicolinamido)phenyl)-4,7,7-trimethyl-8-oxido-3,3a,4,7-tetrahydro-2H-isothiazolo[1,5-a][1,4]thiazin-6-yl)carbamate (Int-33AB, 90 mg, 164 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 5:95) to yield, after drying in vacuo (40° C., 5 mbar), the title compound as a white powder (67 mg, 91% yield). HPLC (method LCMS_gradient) $t_R$=1.13 min. $^1$H NMR (CDCl$_3$, 300 MHz): δ 1.48-1.67 (m, 1H), 1.77 (s, 3H), 1.88 (s, 3H), 1.92-2.03 (m, 1H), 1.93 (s, 3H), 3.41 (dd, J=7.8, 10.4 Hz, 1H), 3.64 (ddd, J=5.0, 10.7, 10.7 Hz, 1H), 4.19-4.29 (m, 1H), 4.65 (br s, 2H), 7.08 (dd, J=8.9, 11.7 Hz, 1H), 7.61 (ddd, J=2.6, 8.3, 8.3 Hz, 1H), 7.91-7.98 (m, 1H), 8.21 (dd, J=2.8, 7.1 Hz, 1H), 8.35 (dd, J=4.6, 8.7 Hz, 1H), 8.47 (d, J=2.6 Hz, 1H), 9.83 (s, 1H). MS (ES+) m/z 448.2 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-chloropicolinamide (18AB)

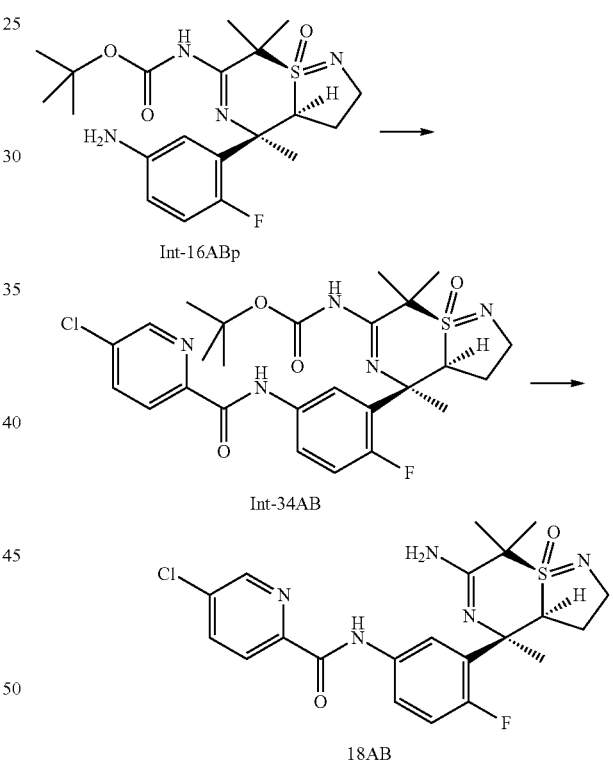

Step 1: tert-butyl ((3aS,4R,8R)-4-(5-(5-chloropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-34AB)

5-Chloropicolinic acid (50.5 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 5-chloropicolinoyl chloride as yellow oil (56 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-chloropicolinoyl chloride (vide supra, 45 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with 2 M ammonia in methanol/dichloromethane, gradient 1:99 to 4:96) to yield, after drying in vacuo (40° C., 5 mbar), the title compound as a brown solid (95 mg, 90% yield). HPLC (method LCMS_fglm) $t_R$=1.36 min. MS (ES+) m/z 564.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-chloropicolinamide (18AB)

tert-Butyl ((3aS,4R,8R)-4-(5-(5-chloropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-34AB, 95 mg, 168 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 5:95) to yield, after drying in vacuo (40° C., 5 mbar), the title compound as an off-white powder (69 mg, 89% yield). HPLC (method LCMS_gradient) $t_R$=1.30 min. $^1$H NMR (CDCl$_3$, 300 MHz): δ 1.48-1.65 (m, 1H), 1.77 (s, 3H), 1.88 (s, 3H), 1.92-2.03 (m, 1H), 1.93 (s, 3H), 3.42 (dd, J=7.7, 10.7 Hz, 1H), 3.64 (ddd, J=5.0, 10.6, 10.6 Hz, 1H), 4.24 (dd, J=6.9, 12.3 Hz, 1H), 4.66 (br s, 2H), 7.08 (dd, J=8.9, 11.7 Hz, 1H), 7.68-7.99 (m, 2H), 8.22 (dd, J=2.4, 6.9 Hz, 1H), 8.26 (d, J=8.5 Hz, 1H), 8.58 (d, J=2.0 Hz, 1H), 9.85 (s, 1H). MS (ES+) m/z 464.2 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-difluoropicolinamide (19AB)

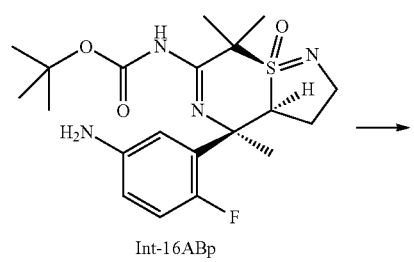

Int-16ABp

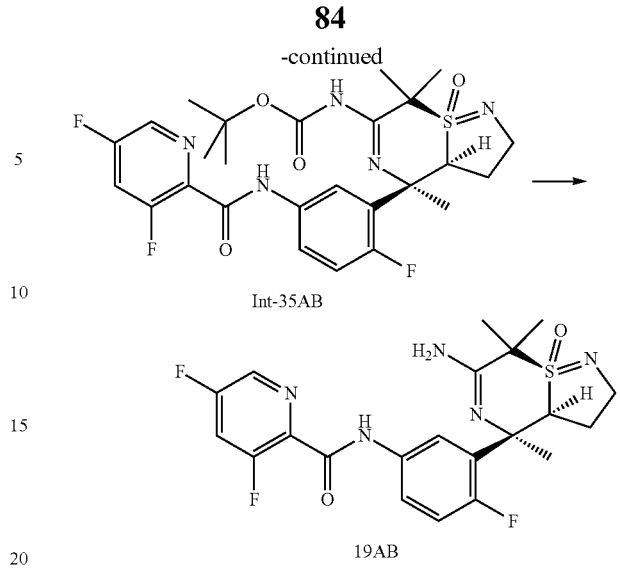

Int-35AB

19AB

Step 1: tert-Butyl ((3aS,4R,8R)-4-(5-(3,5-difluoropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-35AB)

3,5-Difluoropicolinic acid (51 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 3,5-difluoropicolinoyl chloride as colorless oil (57 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 3,5-difluoropicolinoyl chloride (vide supra, 45.4 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 40 g, eluting with 2 M ammonia in methanol/dichloromethane, gradient 1:99 to 4:96) to yield, after drying in vacuo (40° C., 5 mbar), the title compound as a white solid (101 mg, 95% yield). HPLC (method LCMS_fglm) $t_R$=1.23 min. MS (ES+) m/z 566.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-difluoropicolinamide (19AB)

tert-Butyl ((3aS,4R,8R)-4-(5-(3,5-difluoropicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-35AB, 101 mg, 179 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 4:96) to yield, after drying in vacuo (40° C., 5 mbar), the title compound as a white powder (81 mg, 97% yield). HPLC (method LCMS_gradient) $t_R$=1.07 min. $^1$H NMR (CDCl$_3$, 300 MHz): δ 1.48-1.67 (m, 1H), 1.77 (s, 3H), 1.88 (s, 3H), 1.92 (s, 3H), 1.92-2.03 (m, 1H), 3.41 (dd, J=7.3, 10.3 Hz, 1H), 3.64 (ddd, J=5.0, 10.6, 10.6 Hz, 1H), 4.24 (ddd, J=0.8, 6.9, 12.5 Hz, 1H), 4.64 (br s, 2H), 7.07 (dd, J=8.8, 11.6 Hz, 1H), 7.41 (ddd, J=2.3, 8.0, 10.2 Hz, 1H), 7.88-7.95 (m, 1H), 8.20 (dd, J=2.8, 6.9 Hz, 1H), 8.37 (d, J=2.2 Hz, 1H), 9.63 (s, 1H). MS (ES+) m/z 464.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methylpicolinamide (20AB)

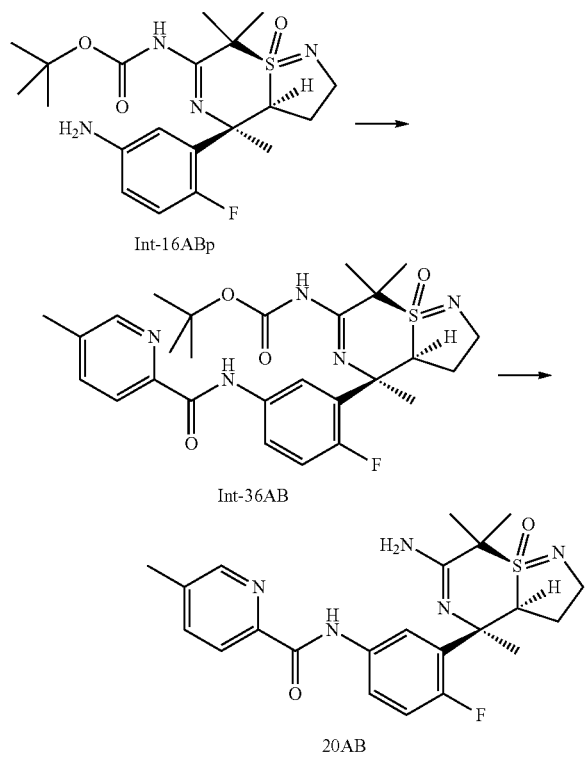

Step 1: tert-Butyl ((3aS,4R,8R)-4-(2-fluoro-5-(5-methylpicolinamido)phenyl)-4,7,7-trimethyl-8-oxido-3,3a,4,7-tetrahydro-2H-isothiazolo[1,5-a][1,4]thiazin-6-yl)carbamate (Int-36AB)

5-Methylpicolinic acid (43.9 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-methylpicolinoyl chloride as green oil (49.7 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (51.3 mg, 69.4 µL, 397 µmol) was added, followed by a solution of 5-methylpicolinoyl chloride (vide supra, 49.7 mg, 320 µmol) in dichloromethane (5 mL). The reaction mixture was stirred for 15 min at 10° C. Then, methanol (2 mL) was added, the mixture was stirred for 5 min at room temperature and concentrated in vacuo. The crude was purified by column chromatography (silica gel, 40 g, eluting with 2 M ammonia in methanol/dichloromethane, gradient 1:99 to 4:96) to yield, after drying in vacuo (40° C., 5 mbar), the title compound as a white solid (72 mg, 70% yield). HPLC (method LCMS_fglm) $t_R$=1.31 min. MS (ES+) m/z 544.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methylpicolinamide (20AB)

tert-Butyl ((3aS,4R,8R)-4-(2-fluoro-5-(5-methylpicolinamido)phenyl)-4,7,7-trimethyl-8-oxido-3,3a,4,7-tetrahydro-2H-isothiazolo[1,5-a][1,4]thiazin-6-yl)carbamate (Int-36AB, 72 mg, 132 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 6:94) to yield, after drying in vacuo (40° C., 5 mbar), the title compound as an off-white powder (57 mg, 97% yield). HPLC (method LCMS_gradient) $t_R$=1.21 min. $^1$H NMR (CDCl$_3$, 300 MHz): δ 1.48-1.66 (m, 1H), 1.77 (s, 3H), 1.88 (s, 3H), 1.92-2.03 (m, 1H), 1.93 (s, 3H), 2.45 (s, 3H), 3.41 (dd, J=7.8, 10.2 Hz, 1H), 3.64 (ddd, J=5.0, 10.5, 10.5 Hz, 1H), 4.24 (dd, J=7.2, 12.0 Hz, 1H), 4.67 (br s, 2H), 7.07 (dd, J=8.8, 11.6 Hz, 1H), 7.71 (d, J=7.9 Hz, 1H), 7.92-8.00 (m, 1H), 8.19 (d, J=8.1 Hz, 1H), 8.23 (dd, J=2.6, 7.1 Hz, 1H), 8.44 (s, 1H), 9.99 (s, 1H). MS (ES+) m/z 444.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-2-methylpyrimidine-5-carboxamide (21AB)

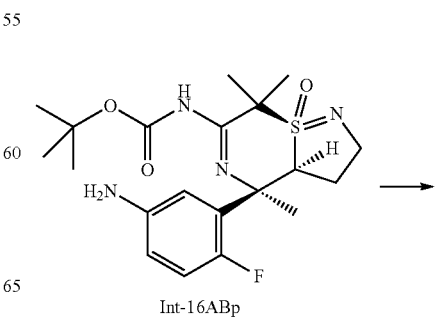

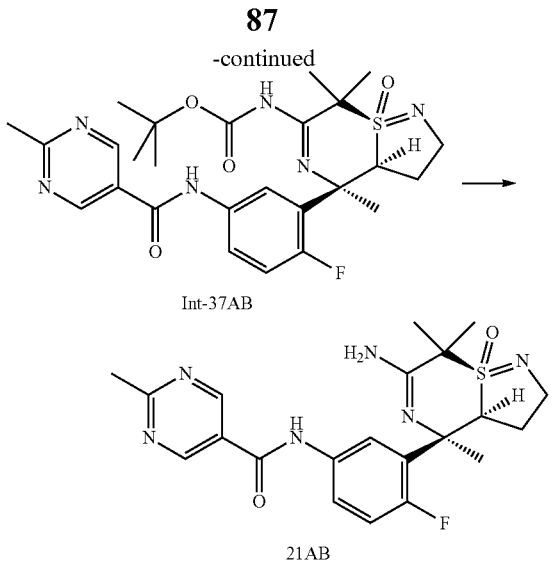

Int-37AB

21AB

Step 1: tert-Butyl ((3aS,4R,8R)-4-(2-fluoro-5-(2-methylpyrimidine-5-carboxamido)phenyl)-4,7,7-trimethyl-8-oxido-3,3a,4,7-tetrahydro-2H-isothiazolo[1,5-a][1,4]thiazin-6-yl)carbamate (Int-37AB)

2-Methylpyrimidine-5-carboxylic acid (44.2 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 2-methylpyrimidine-5-carbonyl chloride as orange oil (50.0 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (41.4 mg, 56 μL, 320 μmol) was added, followed by a solution of 2-methylpyrimidine-5-carbonyl chloride (vide supra, 50.0 mg, 320 μmol) in dichloromethane (5 mL). The reaction mixture was stirred for 45 min at 10° C. Then, methanol (2 mL) was added, the mixture was stirred for 5 min at room temperature and concentrated in vacuo. The crude was purified by column chromatography (silica gel, 40 g, eluting with 2 M ammonia in methanol/dichloromethane, gradient 1:99 to 4:96) to yield, after drying in vacuo (40° C., 5 mbar), the title compound as a light yellow solid (48 mg, purity 67% by HPLC, 31% yield). HPLC (method LCMS_gradient) $t_R$=2.12 min. MS (ES+) m/z 545.5 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-2-methylpyrimidine-5-carboxamide (21AB)

tert-Butyl ((3aS,4R,8R)-4-(2-fluoro-5-(2-methylpyrimidine-5-carboxamido)phenyl)-4,7,7-trimethyl-8-oxido-3,3a,4,7-tetrahydro-2H-isothiazolo[1,5-a][1,4]thiazin-6-yl)carbamate (Int-37AB, 48 mg, 67% purity, 59 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 24 g, eluting with 2 M ammonia in methanol/dichloromethane, gradient 1:99 to 6:94) to yield, after lyophilization from acetonitrile/water, the title compound as an off-white amorphous powder (13 mg, 50% yield). HPLC (method LCMS_gradient) $t_R$=0.94 min. $^1$H NMR (MeOH-d4, 300 MHz): δ 1.61-1.72 (m, 1H), 1.70 (s, 3H), 1.80 (s, 3H), 1.84-2.01 (m, 1H), 1.89 (s, 3H), 2.78 (s, 3H), 3.31-3.42 (m, 1H), 3.54-3.64 (m, 1H), 4.14 (dd, J=7.3, 12.9 Hz, 1H), 7.13 (dd, J=8.7, 11.9 Hz, 1H), 7.73 (ddd, J=3.0, 4.0, 8.7 Hz, 1H), 8.34 (dd, J=2.6, 7.3 Hz, 1H), 9.18 (s, 2H). MS (ES+) m/z 445.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)pyrazine-2-carboxamide (22AB)

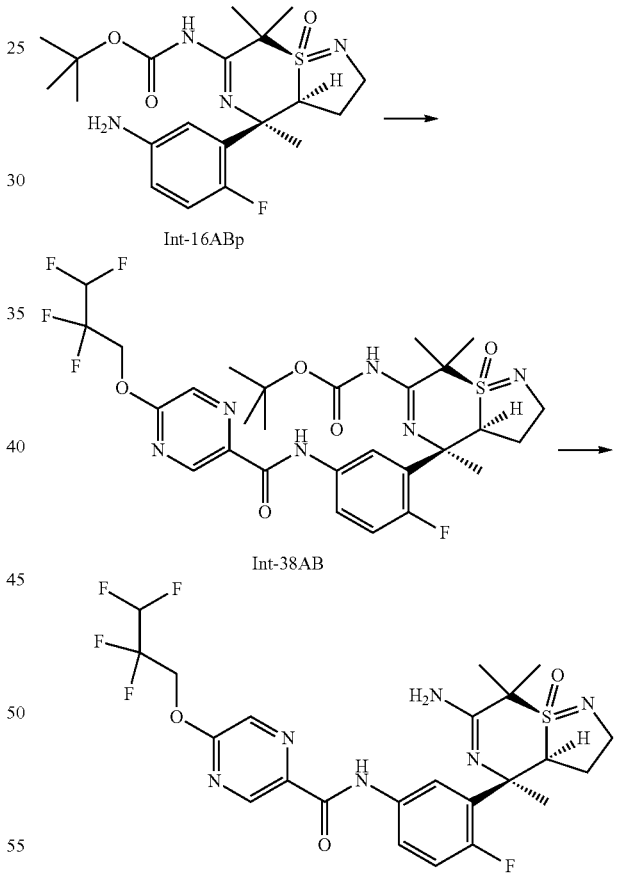

Int-16ABp

Int-38AB

22AB

Step 1: tert-Butyl ((3aS,4R,8R)-4-(2-fluoro-5-(5-(2,2,3,3-tetrafluoropropoxy)pyrazine-2-carboxamido)phenyl)-4,7,7-trimethyl-8-oxido-3,3a,4,7-tetrahydro-2H-isothiazolo[1,5-a][1,4]thiazin-6-yl)carbamate (Int-38AB)

5-(2,2,3,3-Tetrafluoropropoxy)pyrazine-2-carboxylic acid (81.4 mg, 320 μmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 1.5 h at room temperature. Then, it was concentrated in vacuo (40° C., 5 mbar) and dried azeotropically by two cycles of addition of toluene (3 mL) followed by concentration in vacuo to afford 5-(2,2,3,3-tetrafluoropropoxy)pyrazine-2-carbonyl chloride as brown oil (87 mg, quant.). After that, tert-butyl ((3aS, 4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-methylpicolinoyl chloride (vide supra, 70 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with ethyl acetate/n-heptane, gradient 20:80 to 80:20) to yield, after drying in vacuo (40° C., 5 mbar), the title compound as an off-white solid (104 mg, 83% yield). HPLC (method LCMS_fglm) $t_R$=1.37 min. MS (ES+) m/z 661.3 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)pyrazine-2-carboxamide (22AB)

tert-Butyl ((3aS,4R,8R)-4-(2-fluoro-5-(5-(2,2,3,3-tetrafluoropropoxy)pyrazine-2-carboxamido)phenyl)-4,7,7-trimethyl-8-oxido-3,3a,4,7-tetrahydro-2H-isothiazolo[1,5-a][1,4]thiazin-6-yl)carbamate (Int-38AB, 104 mg, 157 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 4:96) to yield, after drying in vacuo (40° C., 5 mbar), the title compound as an off-white powder (84 mg, 94% yield). HPLC (method LCMS_gradient) $t_R$=1.62 min. $^1$H NMR (CDCl$_3$, 300 MHz): δ 1.47-1.66 (m, 1H), 1.77 (s, 3H), 1.88 (s, 3H), 1.90-2.06 (m, 1H), 1.93 (s, 3H), 3.42 (dd, J=7.9, 10.1 Hz, 1H), 3.64 (ddd, J=5.0, 10.6, 10.6 Hz, 1H), 4.24 (dd, J=7.3, 12.3 Hz, 1H), 4.66 (br s, 2H), 4.88 (t, J=12.7 Hz, 2H), 6.02 (tt, J=3.7, 53.0 Hz, 1H), 7.08 (dd, J=8.9, 11.7 Hz, 1H), 7.88-7.97 (m, 1H), 8.21 (dd, J=2.7, 7.0 Hz, 1H), 8.30 (s, 1H), 9.05 (s, 1H), 9.51 (s, 1H). MS (ES+) m/z 561.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-dimethylpicolinamide (23AB)

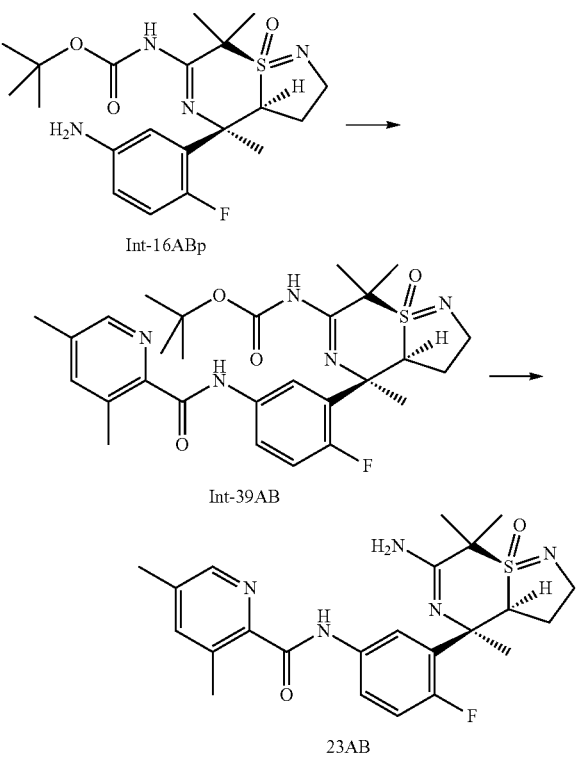

Step 1: tert-Butyl ((3aS,4R,8R)-4-(5-(3,5-dimethylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-39AB)

3,5-Dimethylpicolinic acid (48.4 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 90 min at room temperature. Then, it was concentrated in vacuo (40° C., 5 mbar) and dried azeotropically by two cycles of addition of toluene (3 mL) followed by concentration in vacuo to afford 3,5-dimethylpicolinoyl chloride as brown oil (54 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 3,5-dimethylpicolinoyl chloride (vide supra, 43.2 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 24 g, eluting with 2 M ammonia in methanol/dichloromethane, gradient 1:99 to 5:95) to yield, after drying in vacuo (40° C., 5 mbar), the title compound as a white solid (102 mg, 97% yield). HPLC (method LCMS_fglm) $t_R$=1.40 min. MS (ES+) m/z 558.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-3,5-dimethylpicolinamide (23AB)

tert-Butyl ((3aS,4R,8R)-4-(5-(3,5-dimethylpicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-39AB, 102 mg, 183 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, eluting with 2 M ammonia in methanol/dichloromethane, gradient 1:99 to 5:95) to yield, after drying in vacuo (40° C., 5 mbar), the title compound as an off-white solid (74 mg, 88% yield). HPLC (method LCMS_gradient) $t_R$=1.33 min. $^1$H NMR (CDCl$_3$, 300 MHz): δ 1.47-1.67 (m, 1H), 1.77 (s, 3H), 1.88 (s, 3H), 1.90-2.06 (m, 1H), 1.92 (s, 3H), 2.39 (s, 3H), 2.78 (s, 3H), 3.41 (dd, J=7.9, 10.1 Hz, 1H), 3.63 (ddd, J=5.0, 10.6, 10.6 Hz, 1H), 4.24 (dd, J=7.1, 11.9 Hz, 1H), 4.67 (br s, 2H), 7.05 (dd, J=8.9, 11.7 Hz, 1H), 7.45 (s, 1H), 7.92-8.00 (m, 1H), 8.14 (dd, J=2.6, 7.1 Hz, 1H), 8.27 (s, 1H), 10.23 (s, 1H). MS (ES+) m/z 458.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methoxypicolinamide (24AB)

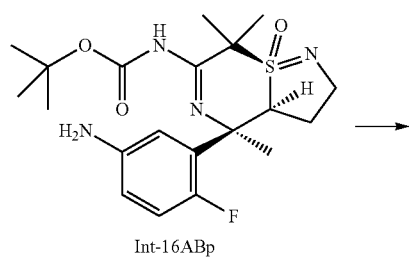

Int-16ABp

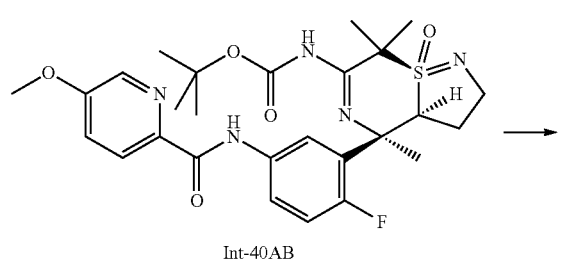

Int-40AB

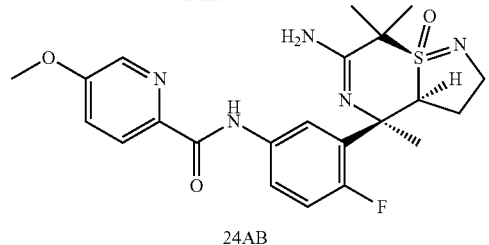

24AB

Step 1: tert-Butyl ((3aS,4R,8R)-4-(2-fluoro-5-(5-methoxypicolinamido)phenyl)-4,7,7-trimethyl-8-oxido-3,3a,4,7-tetrahydro-2H-isothiazolo[1,5-a][1,4]thiazin-6-yl)carbamate (Int-40AB)

5-Methoxypicolinic acid (49.1 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2 h at room temperature. Then, it was concentrated in vacuo (40° C., 5 mbar) and dried azeotropically by two cycles of addition of toluene (3 mL) followed by concentration in vacuo to afford 5-methoxypicolinoyl chloride as dark brown oil (54.8 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-methoxypicolinoyl chloride (vide supra, 43.8 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 24 g, eluting with 2 M ammonia in methanol/dichloromethane, gradient 1:99 to 3:97) to yield, after drying in vacuo (40° C., 5 mbar), the title compound as an off-white solid (92 mg, 87% yield). HPLC (method LCMS_fglm) $t_R$=1.28 min. MS (ES+) m/z 560.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methoxypicolinamide (24AB)

tert-Butyl ((3aS,4R,8R)-4-(2-fluoro-5-(5-methoxypicolinamido)phenyl)-4,7,7-trimethyl-8-oxido-3,3a,4,7-tetrahydro-2H-isothiazolo[1,5-a][1,4]thiazin-6-yl)carbamate (Int-40AB, 92 mg, 164 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature and concentrated in vacuo. The crude was purified by column chromatography (silica gel, 12 g, eluting with 2 M ammonia in methanol/dichloromethane, gradient 1:99 to 5:95) to yield, after lyophilization from acetonitrile/water, the title compound as an off-white amorphous powder (52 mg, 69% yield). HPLC (method LCMS_gradient) $t_R$=1.41 min. $^1$H NMR (CDCl$_3$, 300 MHz): δ

1.49-1.68 (m, 1H), 1.77 (s, 3H), 1.88 (s, 3H), 1.92-2.03 (m, 1H), 1.92 (s, 3H), 3.41 (dd, J=7.6, 10.4 Hz, 1H), 3.64 (ddd, J=5.0, 10.6, 10.6 Hz, 1H), 3.95 (s, 3H), 4.18-4.29 (m, 1H), 4.66 (br s, 2H), 7.06 (dd, J=8.7, 11.7 Hz, 1H), 7.35 (dd, J=2.8, 8.7 Hz, 1H), 7.94 (ddd, J=2.8, 4.0, 8.7 Hz, 1H), 8.21 (dd, J=2.8, 7.1 Hz, 1H), 8.23-8.30 (m, 2H), 9.86 (s, 1H). MS (ES+) m/z 460.3 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-ethoxypicolinamide (25AB)

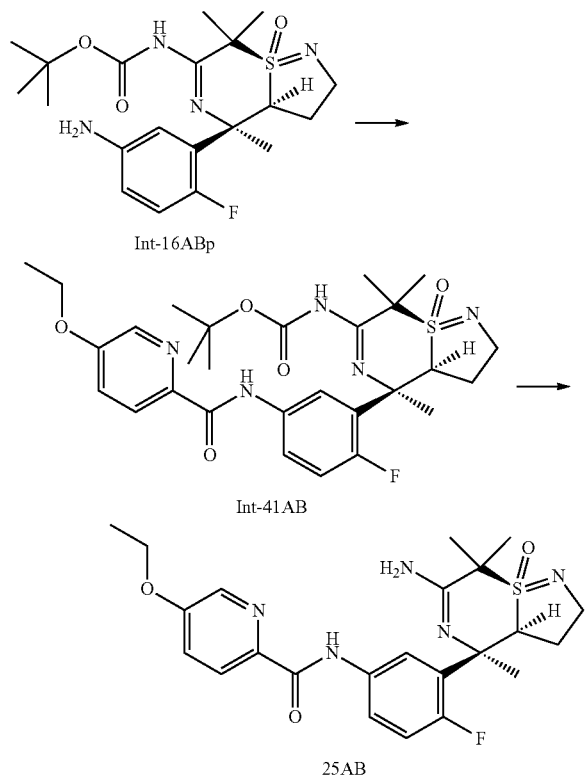

Step 1: tert-Butyl ((3aS,4R,8R)-4-(5-(5-ethoxypicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-41AB)

5-Ethoxypicolinic acid (53.6 mg, 320 μmol) was suspended in dichloromethane (5 mL), the suspension was cooled to 0-5° C. (ice bath) and oxalyl chloride (56.9 mg, 39.3 μL, 448 μmol) as well as dimethylformamide (0.308 M in toluene, 51.9 μL, 16 μmol) were added. The mixture was stirred for 2.5 h at room temperature. Then, it was concentrated in vacuo (40° C., 5 mbar) and dried azeotropically by two cycles of addition of toluene (3 mL) followed by concentration in vacuo to afford 5-ethoxypicolinoyl chloride as purple oil (59 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 μmol) was dissolved in dichloromethane (5 mL), the solution cooled to 10° C. and N,N-diisopropylethylamine (36.5 mg, 49.4 μL, 283 μmol) was added, followed by a solution of 5-ethoxypicolinoyl chloride (vide supra, 47.5 mg, 256 μmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 24 g, eluting with 2 M ammonia in methanol/dichloromethane, gradient 1:99 to 3:97) to yield, after drying in vacuo (40° C., 5 mbar), the title compound as a colorless viscous oil (95 mg, 88% yield). HPLC (method LCMS_f-glm) $t_R$=1.36 min. MS (ES+) m/z 574.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-ethoxypicolinamide (25AB)

tert-Butyl ((3aS,4R,8R)-4-(5-(5-ethoxypicolinamido)-2-fluorophenyl)-4,7,7-trimethyl-8-oxido-3,3a,4,7-tetrahydro-2H-isothiazolo[1,5-a][1,4]thiazin-6-yl)carbamate (Int-41AB, 95 mg, 166 μmol) was dissolved in dichloromethane (5 mL) and trifluoroacetic acid (537 mg, 363 μL, 4.71 mmol) was added. The solution was stirred for 17 h at room temperature. After that, the mixture was concentrated in vacuo, the residue was redissolved in methanol (10 mL), aqueous ammonia (25% m/m, 250 μL) was added, stirred for 10 min at room temperature, and concentrated in vacuo. The crude was purified by column chromatography (silica gel, 12 g, 10 eluting with 2 M ammonia in methanol/dichloromethane, gradient 1:99 to 5:95) to yield, after drying in vacuo (40° C., 5 mbar), the title compound as a white solid (78 mg, 99% yield). HPLC (method LCMS_gradient) $t_R$=1.42 min. $^1$H NMR (CDCl$_3$, 300 MHz): δ 1.50 (t, J=7.0 Hz, 3H), 1.51-1.66 (m, 1H), 1.76 (s, 3H), 1.88 (s, 3H), 1.90-2.03 (m, 1H), 1.92 (s, 3H), 3.41 (dd, J=7.7, 10.5 Hz, 1H), 3.63 (ddd, J=5.0, 10.5, 10.5 Hz, 1H), 4.11-4.29 (m, 3H), 4.65 (br s, 2H), 7.06 (dd, J=8.9, 11.7 Hz, 1H), 7.33 (dd, J=2.7, 8.8 Hz, 1H), 7.90-7.99 (m, 1H), 8.16-8.29 (m, 3H), 9.86 (s, 1H). MS (ES+) m/z 474.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-methoxy-3-methylpicolinamide (26AB)

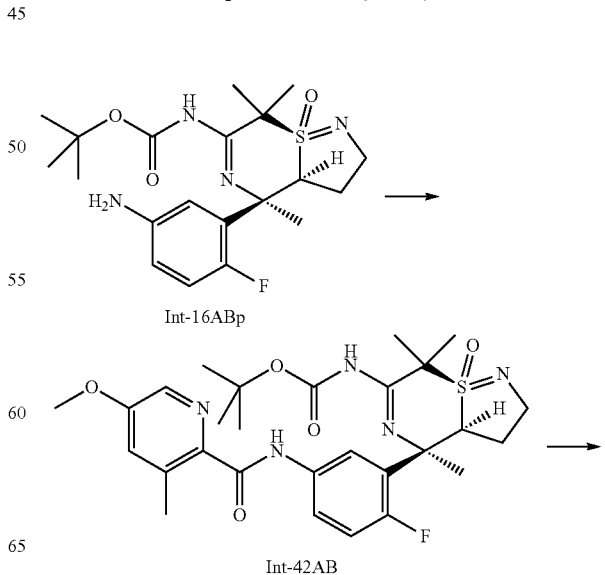

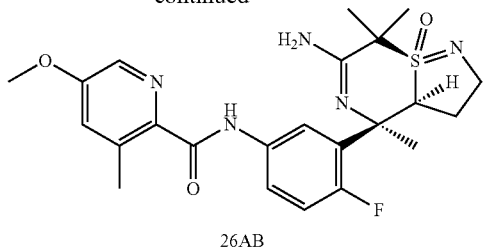

Step 1: tert-Butyl ((3aS,4R,8R)-4-(2-fluoro-5-(5-methoxy-3-methylpicolinamido)phenyl)-4,7,7-trimethyl-8-oxido-3,3a,4,7-tetrahydro-2H-isothiazolo[1,5-a][1,4]thiazin-6-yl)carbamate (Int-42AB)

5-Methoxy-3-methylpicolinic acid (53.6 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 1 h at room temperature. Then, it was concentrated in vacuo (40° C., 5 mbar) and dried azeotropically by two cycles of addition of toluene (3 mL) followed by concentration in vacuo to afford 5-methoxy-3-methylpicolinoyl chloride as brown oil (59 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-methoxy-3-methylpicolinoyl chloride (vide supra, 47.4 mg, 256 µmol) in dichloromethane (4 mL). The reaction mixture was stirred for 15 min at 10° C. Then, methanol (2 mL) was added, the mixture was stirred for 5 min at room temperature and concentrated in vacuo. The crude was purified by column chromatography (silica gel, 12 g, eluting with 2 M ammonia in methanol/dichloromethane, gradient 1:99 to 3:97) to yield, after drying in vacuo (40° C., 5 mbar), the title compound as a yellow solid (102 mg, 95% yield). HPLC (method LCMS_fglm) $t_R$=1.37 min. MS (ES+) m/z 574.4 [M+H].

Step 2: N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxy-3-methylpicolinamide (26AB)

tert-Butyl ((3aS,4R,8R)-4-(2-fluoro-5-(5-methoxy-3-methylpicolinamido)phenyl)-4,7,7-trimethyl-8-oxido-3,3a,4,7-tetrahydro-2H-isothiazolo[1,5-a][1,4]thiazin-6-yl)carbamate (Int-42AB, 102 mg, 178 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 24 g, eluting with 2 M ammonia in methanol/dichloromethane, gradient 1:99 to 4:96) to yield, after drying in vacuo (40° C., 5 mbar), the title compound as a white solid (75 mg, 89% yield). HPLC (method LCMS-_gradient) $t_R$=1.32 min. $^1$H NMR (CDCl$_3$, 300 MHz): δ 1.49-1.67 (m, 1H), 1.77 (s, 3H), 1.88 (s, 3H), 1.93-2.04 (m, 1H), 1.93 (s, 3H), 2.81 (s, 3H), 3.41 (dd, J=7.5, 10.3 Hz, 1H), 3.64 (ddd, J=5.0, 10.6, 10.6 Hz, 1H), 3.93 (s, 3H), 4.23 (ddd, J=0.9, 7.2, 12.3 Hz, 1H), 4.77 (br s, 2H), 7.05 (dd, J=8.8, 11.7 Hz, 1H), 7.09 (s, 1H), 7.95 (ddd, J=2.8, 4.1, 8.7 Hz, 1H), 8.11 (dd, J=2.8, 7.3 Hz, 1H), 8.13 (d, J=2.8 Hz, 1H), 10.10 (s, 1H). MS (ES+) m/z 474.4 [M+H].

N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-ethoxypyrazine-2-carboxamide (27AB)

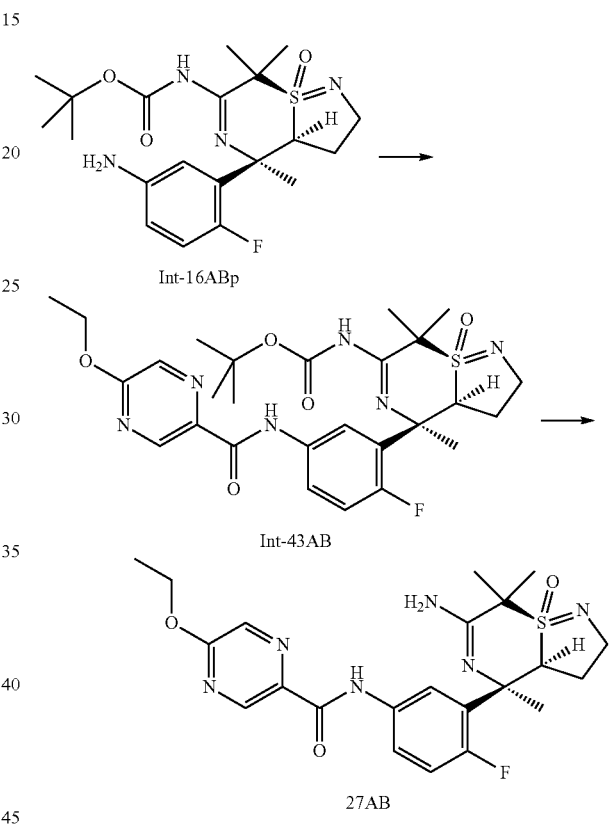

Step 1: tert-Butyl ((3aS,4R,8R)-4-(5-(5-ethoxypyrazine-2-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-43AB)

5-Ethoxypyrazine-2-carboxylic acid (53.9 mg, 320 µmol) was suspended in dichloromethane (5 mL), the suspension was cooled to 0-5° C. (ice bath) and oxalyl chloride (56.9 mg, 39.3 µL, 448 µmol) as well as dimethylformamide (0.308 M in toluene, 51.9 µL, 16 µmol) were added. The mixture was stirred for 1.5 h at room temperature. Then, it was concentrated in vacuo (40° C., 5 mbar) and dried azeotropically by two cycles of addition of toluene (3 mL) followed by concentration in vacuo to afford 5-ethoxypyrazine-2-carbonyl chloride as yellow oil (59.7 mg, quant.). After that, tert-butyl ((3aS,4R,8R)-4-(5-amino-2-fluorophenyl)-4,7,7-trimethyl-8-oxido-3,3a,4,7-tetrahydro-2H-isothiazolo[1,5-a][1,4]thiazin-6-yl)carbamate (Int-16ABp, 80 mg, 188 µmol) was dissolved in dichloromethane (5 mL), the solution cooled to 10° C. and N,N-diisopropylethylamine (36.5 mg, 49.4 µL, 283 µmol) was added, followed by a solution of 5-ethoxypyrazine-2-carbonyl chloride (vide supra, 47.7 mg, 256 µmol) in dichloromethane (4 mL). The reaction mixture was stirred for 15 min at 10° C. Then, methanol (2 mL) was added, the mixture stirred for 5 min at room temperature and concentrated in vacuo. The crude was purified by column chromatography (silica gel, 24 g, eluting with 2 M ammonia in methanol/dichloromethane, gradient 1:99 to 3:97) to yield, after drying in vacuo (40° C., 5 mbar), the title compound as a white solid (92 mg, 85% yield). HPLC (method LCMS_fglm) $t_R$=1.37 min. MS (ES+) m/z 575.4 [M+H].

Step 2: N-(3-((3aS,4R,8R)-6-Amino-4,7,7-trimethyl-8-oxido-3,3a,4,7-tetrahydro-2H-isothiazolo[1,5-a][1,4]thiazin-4-yl)-4-fluorophenyl)-5-ethoxypyrazine-2-carboxamide (27AB)

tert-Butyl ((3aS,4R,8R)-4-(5-(5-ethoxypyrazine-2-carboxamido)-2-fluorophenyl)-4,7,7-trimethyl-8-oxido-3,3a,4,7-tetrahydro-2H-isothiazolo[1,5-a][1,4]thiazin-6-yl)carbamate (Int-43AB, 92 mg, 160 µmol) was dissolved in dichloromethane (5 mL) and trifluoroacetic acid (537 mg, 363 µL, 4.71 mmol) was added. The solution was stirred for 17 h at room temperature. After that, the mixture was concentrated in vacuo, the residue was redissolved in methanol (10 mL), aqueous ammonia (25% m/m, 250 µL) was added, stirred for 10 min at room temperature, and concentrated in vacuo. The crude was purified by column chromatography (silica gel, 12 g, eluting with 2 M ammonia in methanol/dichloromethane, gradient 1:99 to 5:95) to yield, after drying in vacuo (40° C., 5 mbar), the title compound as a white solid (74 mg, 97% yield). HPLC (method LCMS_gradient) $t_R$=1.33 min. $^1$H NMR (CDCl$_3$, 300 MHz): δ 1.46 (t, J=7.1 Hz, 3H), 1.50-1.65 (m, 1H), 1.77 (s, 3H), 1.88 (s, 3H), 1.92-2.03 (m, 1H), 1.92 (s, 3H), 3.41 (dd, J=7.6, 10.4 Hz, 1H), 3.64 (ddd, J=5.0, 10.6, 10.6 Hz, 1H), 4.24 (ddd, J=0.9, 7.1, 12.1 Hz, 1H), 4.51 (q, J=7.2 Hz, 2H), 4.65 (br s, 2H), 7.07 (dd, J=8.7, 11.7 Hz, 1H), 7.92 (ddd, J=3.1, 3.9, 8.7 Hz, 1H), 8.13 (d, J=1.2 Hz, 1H), 8.20 (dd, J=2.8, 7.1 Hz, 1H), 9.01 (d, J=1.2 Hz, 1H), 9.52 (s, 1H). MS (ES+) m/z 475.3 [M+H].

The invention claimed is:

1. A compound of formula I,

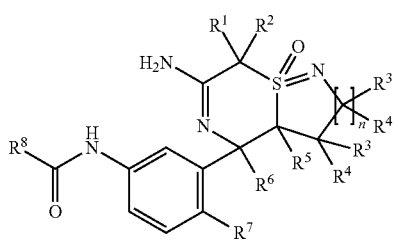

wherein
n is 1, 2 or 3;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is each independently selected from the group consisting of
  i) hydrogen,
  ii) $C_{1-6}$-alkyl, and
  iii) halogen;
$R^4$ is each independently selected from the group consisting of
  i) hydrogen,
  ii) $C_{1-4}$-alkyl, and
  iii) halogen;
or wherein $R^3$ and $R^4$ together are —(CH$_2$)$_m$—, wherein m is 2, 3, 4 or 5,
$R^5$ is hydrogen;
$R^6$ is selected from the group consisting of
  i) $C_{1-6}$-alkyl, and
  ii) halogen-$C_{1-6}$-alkyl;
$R^7$ is selected from the group consisting of
  i) hydrogen, and
  ii) halogen;
$R^8$ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, COOR$^9$, wherein R$^9$ is H or $C_{1-6}$-alkyl, CONR$^{10}$R$^{11}$, wherein R$^{10}$ is H or $C_{1-6}$-alkyl $C_{3-6}$-cycloalkyl and R$^{11}$ is H or $C_{1-6}$-alkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-4}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
  iii) heteroaryl, and
  iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, COOR$^9$, wherein R$^9$ is H or $C_{1-6}$-alkyl, CONR$^{10}$R$^{11}$, wherein R$^{10}$ is H or $C_{1-6}$-alkyl $C_{3-6}$-cycloalkyl and R$^{11}$ is H or $C_{1-6}$-alkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
or a pharmaceutically acceptable salt thereof.

2. The compound according to claim 1, wherein n, $R^1$, $R^2$, $R^3$, $R^4$, $R^5$, $R^6$, $R^7$ and $R^8$ are as described and when n=1, then the 5-ring has cis configuration.

3. The compound according to claim 1, which is of formula Ia, wherein n, $R^1$, $R^2$, $R^3$, $R^4$, $R^5$, $R^6$, $R^7$ and $R^8$ are as described in claim 1

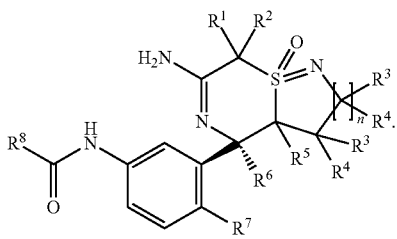

4. The compound according to claim 1, wherein $R^1$ and $R^2$ are methyl.

5. The compound according to claim 1, wherein $R^3$ and $R^4$ are hydrogen.

6. The compound according to claim 1, wherein $R^5$ is hydrogen.

7. The compound according to claim 1, wherein $R^6$ is methyl.

8. The compound according to claim 1, wherein $R^7$ is F.

9. The compound according to claim 1, wherein $R^8$ is heteroaryl, substituted by 1-2 substituents individually selected from cyano, halogen, halogen-$C_{1-6}$-alkoxy, halogen-$C_{1-6}$-alkyl and $C_{1-6}$-alkyl.

10. The compound according to claim 1, wherein $R^8$ is heteroaryl which is selected from pyridinyl, pyrazinyl, pyrimidyl or 1H-pyrazolyl, each substituted by 1-2 substituents individually selected from cyano, halogen, halogen-$C_{1-6}$-alkoxy, halogen-$C_{1-6}$-alkyl and $C_{1-6}$-alkyl.

11. The compound according to claim 1, wherein $R^8$ is heteroaryl, substituted by 1-2 substituents individually selected from cyano and $C_{1-6}$-alkyl.

12. The compound according to claim 1, wherein $R^8$ is phenyl substituted by 1-2 substituents individually selected from cyano, halogen and $C_{1-6}$-alkyl.

13. The compound according to claim 1, wherein n is 1.

14. The compound according to claim 1, selected from the group consisting of:
- N-(3-((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy) picolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)pyrazine-2-carboxamide,
- N-(3-((3aS,4R8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl)picolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-cyano-2-methylbenzamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5 (difluoromethoxy)-3-methylpicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy)picolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(difluoromethoxy)picolinamide,
- N-(3-((3aS,4R,8R)-6-amino-4,7,7-trimethyl-8-oxido-3,3a,4,7-tetra hydro-2H-isothiazolo[1,5-a][1,4]thiazin-4-yl)-4-fluorophenyl)-5-methoxypyrazine-2-carboxamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)pyrazine-2-carboxamide,
- N-(3-((3aS,4R,8R)-6-amino-4,7,7-trim ethyl-8-oxido-3,3a,4,7-tetrahydro-2H-isothiazolo[1,5-a][1,4]thiazin-4-yl)-4-fluorophenyl)-5-cyanopicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-fluoropicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-chloropicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-difluoropicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methylpicolinamide,
- N-(3-((3aS,4R8R)-6-amino-4,7,7-trimethyl-8-oxido-3,3a,4,7-tetrahydro-2H-isothiazolo[1,5-a][1,4]thiazin-4-yl)-4-fluorophenyl)-2-methylpyrimidine-5-carboxamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy) pyrazine-2-carboxamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dimethylpicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxypicolinamide,
- N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-ethoxypicolinamide,
- N-(3-((3aS,4R,8R)-6-amino-4,7,7-trimethyl-8-oxido-3,3a,4,7-tetrahydro-2-isothiazolo[1,5-a][1,4]thiazin-4-yl)-4-fluorophenyl)-5-methoxy-3-methylpicolinamide, and N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-ethoxypyrazine-2-carboxamide, or pharmaceutically acceptable salts thereof.

15. The compound according to claim 1, selected from the group consisting of:

N-(3-((3aS,4R,8R)-6-amino-4,7,7-trim ethyl-8-oxido-3,3a,4,7-tetrahydro-2H-isothiazolo[1,5-a][1,4]thiazin-4-yl)-4-fluorophenyl)-5-cyano-3-methylpicolinamide, N-(3-((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-cyanopicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3,5-dichloropicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-2-chloro-4-cyanobenzamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-chloro-1-(difluoromethyl)-1H-pyrazole-3-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy) pyrazine-2-carboxamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-3-chloro-5-(trifluoromethyl) picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-4-cyano-2-methylbenzamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2-difluoroethoxy)picolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(difluoromethoxy)-3-methylpicolinamide, N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-(2,2,3,3-tetrafluoropropoxy) picolinamide, N-(3-((3aS,4R,8R)-6-amino-4,7,7-trimethyl-8-oxido-3,3a4,7-tetra hydro-2H-isothiazolo[1,5-a][1,4]thiazin-4-yl)-4-fluorophenyl)-3-chloro-5-(difluoromethoxy)picolinamide, and N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-methoxypyrazine-2-carboxamide, or pharmaceutically acceptable salts thereof.

16. The compound according to claim 1, selected from the group consisting of:

N-(3-((3aS,4R,8R)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide and N-(3-((3aR,4R,8S)-6-amino-4,7,7-trimethyl-8-oxido-3,3a,4,7-tetrahydro-2H-isothiazolo[1,5-a][1,4]thiazin-4-yl)-4-fluorophenyl)-5-cyano-3-methylpicolinamide, or pharmaceutically acceptable salts thereof.

17. A method for treating diseases and disorders characterized by elevated β-amyloid levels and/or β-amyloid oligomers and/or β-amyloid plaques and further deposits, comprising the step of administering a therapeutically effective amount of a compound according to claim 1, or a pharmaceutically acceptable salt thereof, to a human being or animal in need thereof.

18. A pharmaceutical composition, comprising a therapeutically effective amount of a compound according to claim 1, or a pharmaceutically acceptable salt thereof, and a pharmaceutically acceptable carrier.

19. A method for treating Alzheimer's Disease, comprising the step of administering a therapeutically effective amount of a compound according to claim 1, or a pharmaceutically acceptable salt thereof, to a human being or animal in need thereof.

* * * * *

UNITED STATES PATENT AND TRADEMARK OFFICE
CERTIFICATE OF CORRECTION

PATENT NO.        : 10,246,468 B2
APPLICATION NO.   : 15/735890
DATED             : April 2, 2019
INVENTOR(S)       : Bjoern Bartels et al.

Page 1 of 1

It is certified that error appears in the above-identified patent and that said Letters Patent is hereby corrected as shown below:

In the Claims

At Column 98, Line 13, "C1-4-alkyl" should be replaced with "C1-6-alkyl."

At Column 98, Line 15, "–(CH2)m–" should be printed as "–(CH2)m-."

At Column 98, Lines 39 and 40, "C3-4-cycloalkyl" should be printed as "C3-6-cycloalkyl."

Signed and Sealed this
Thirteenth Day of August, 2019

Andrei Iancu
*Director of the United States Patent and Trademark Office*